US010265409B2

(12) United States Patent
Owen et al.

(10) Patent No.: US 10,265,409 B2
(45) Date of Patent: *Apr. 23, 2019

(54) MACROMOLECULES

(71) Applicant: STARPHARMA PTY LTD, Melbourne, Victoria (AU)

(72) Inventors: David Owen, Vermont South (AU); Brian Devlin Kelly, Ringwood East (AU); Peter Karellas, Coberg (AU)

(73) Assignee: STARPHARMA PTY LTD, Melbourne (AU)

(*) Notice: Subject to any disclaimer, the term of this patent is extended or adjusted under 35 U.S.C. 154(b) by 45 days.

This patent is subject to a terminal disclaimer.

(21) Appl. No.: 15/688,780

(22) Filed: Aug. 28, 2017

(65) Prior Publication Data
US 2017/0354739 A1 Dec. 14, 2017

Related U.S. Application Data

(63) Continuation of application No. 14/124,651, filed as application No. PCT/AU2012/000647 on Jun. 6, 2012, now Pat. No. 9,744,246.

(60) Provisional application No. 61/493,886, filed on Jun. 6, 2011.

(51) Int. Cl.
| | |
|---|---|
| *A61K 31/74* | (2006.01) |
| *A61K 47/59* | (2017.01) |
| *C08G 69/10* | (2006.01) |
| *C08G 69/40* | (2006.01) |
| *C08G 83/00* | (2006.01) |
| *A61K 47/65* | (2017.01) |
| *A61K 47/60* | (2017.01) |
| *A61K 47/68* | (2017.01) |

(52) U.S. Cl.
CPC ............. *A61K 47/59* (2017.08); *A61K 47/60* (2017.08); *A61K 47/65* (2017.08); *A61K 47/68* (2017.08); *C08G 69/10* (2013.01); *C08G 69/40* (2013.01); *C08G 83/003* (2013.01)

(58) Field of Classification Search
CPC .. A61K 2800/522; A61K 8/365; A61K 8/892; A61K 47/65; A61K 8/362; A61K 8/368; A61K 31/19; A61K 31/215; C10M 105/36; C10N 2230/10; C08G 83/003; C08G 63/916
See application file for complete search history.

(56) References Cited

U.S. PATENT DOCUMENTS

| | | | | |
|---|---|---|---|---|
| 5,840,900 | A | * 11/1998 | Greenwald | .......... A61K 31/335 546/48 |
| 8,703,907 | B2 | 4/2014 | Ashley | |
| 8,754,190 | B2 | 6/2014 | Ashley | |
| 8,946,405 | B2 | 2/2015 | Ashley | |
| 9,387,254 | B2 | 7/2016 | Santi | |
| 2009/0324535 | A1 | 12/2009 | Boyd | |

FOREIGN PATENT DOCUMENTS

| | | | |
|---|---|---|---|
| CN | 101420962 | 4/2009 | |
| WO | WO 2007/082331 | 7/2007 | |
| WO | WO2007082331 A1 * | 7/2007 | ............. A61K 31/74 |
| WO | WO 2008/017125 | 2/2008 | |

OTHER PUBLICATIONS

Ansell et al., "Modulating the Therapeutic Activity of Nanoparticle Delivered Paclitaxel by Manipulating the Hydrophobicity of Prodrug Conjugates," J. Med. Chem. 2008, 51, 3288-3296.
Bi, et al., "Multifunctional Poly(amidoamine) Dendrimer-Taxol Conjugates: Synthesis, Characterization and Stability", Journal of Computational and Theoretical Nanoscience (2007), vol. 4, pp. 1179-1187.
Fox, et al. "Synthesis and in vivo antitumor efficacy of PEGylated poly (l-lysine) dendrimer-camptothecin conjugates." Molecular pharmaceutics 6(5) (2009): 1562-1572.
Lim, et al., "Design, Synthesis, Characterization and Biological Evaluation of Triazine Dendrimers Bearing Paclitaxel Using Ester and Ester/Disulfide Linkages", Bioconjugate Chemistry (2009), vol. 20, pp. 2154-2161.
Matsumoto et al., "Controlled Drug Release: New Water-Soluble Prodrugs of an HIV Protease Inhibitor," Bioorganic & Medicinal Chemistry Letters, 2001, 11, 605-609.
Ojima et al., "Tumor-Specific novel Taxoid-Monoclonal Antibody Conjugates," J. Med. Chem. 2002, 45, 5620-5623.
Sugahara et al., "Paclitaxel Delivery Systems: The Use of Amino Acid Linkers in the Conjugation of Paclitaxel with Carboxymethyldextran to Create Prodrugs," Biol. Pharm. Bull., 2002, 25(5) 632-641.

(Continued)

*Primary Examiner* — Marcela M Cordero Garcia
*Assistant Examiner* — Jia-Hai Lee
(74) *Attorney, Agent, or Firm* — Knobbe, Martens, Olson & Bear, LLP

(57) ABSTRACT

A macromolecule includes i) a dendrimer with a core and at least one generation of lysine residue building units, the outermost generation of building units having surface amino groups, ii) a first terminal group covalently attached to a first surface amino group of a building unit, which includes a residue of docetaxel (DTX), and iii) a second terminal group covalently attached to a second surface amino group of a building unit, which includes a pharmacokinetic modifying agent. The pharmacokinetic modifying agent can be a polyethylene glycol (PEG). The first terminal group can be covalently attached to the surface amino group of the dendrimer through a diacid linker. The diacid linker can include a 2,2'-thiodiacetic acid residue. The diacid linker can form an ester bond with a hydroxyl group of the DTX and an amide bond with the surface amino group. A pharmaceutically acceptable salt of the macromolecule can be prepared.

21 Claims, No Drawings
Specification includes a Sequence Listing.

(56) References Cited

OTHER PUBLICATIONS

Venditto, et al., "Cancer therapies utilizing the camptothecins: a review of the in vivo literature." Molecular pharmaceutics 7(2) (2010): 307-349.
Zhu, et al., "PEGylated PAMAM Dendrimer-Doxorubicin Conjugates: In Vitro Evaluation and In Vivo Tumor Accumulation", Pharmaceutical Research (2010), vol. 27, No. 1, pp. 161-174.
International Search Report dated Aug. 2, 2012 for International Application No. PCT/AU2012/000647.
International Preliminary Report on Patentability dated Apr. 26, 2013 for International Application No. PCT/AU2012/000647.

* cited by examiner

SEQUENCE LISTING

<160> NUMBER OF SEQ ID NOS: 2

<210> SEQ ID NO 1

```
<211> LENGTH: 4
<212> TYPE: PRT
<213> ORGANISM: Artificial Sequence
<220> FEATURE:
<223> OTHER INFORMATION: Synthetic

<400> SEQUENCE: 1

Gly Phe Leu Gly
1

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Gly Ile Leu Gly Val Pro
1               5
```

MACROMOLECULES

CROSS REFERENCE TO RELATED APPLICATIONS

Any and all applications for which a foreign or domestic priority claim is identified in the Application Data Sheet as filed with the present application are hereby incorporated by reference under 37 CFR 1.57.

REFERENCE TO SEQUENCE LISTING

The present application incorporates by reference the sequence listing submitted as an ASCII text filed via EFS-Web on Aug. 28, 2017. The Sequence Listing is provided as a file entitled 16796845_1.txt, created on Dec. 5, 2013, which is 0.6 Kb in size.

FIELD OF THE INVENTION

The present invention relates to a macromolecule comprising a dendrimer having surface amine groups to which at least two different, terminal groups are attached including a pharmaceutically active agent and a pharmacokinetic modifying agent, the pharmaceutically active agent being attached covalently through a diacid linker. Pharmaceutical compositions and methods of treatment are also described.

BACKGROUND OF THE INVENTION

There are a number of difficulties associated with the formulation and delivery of pharmaceutically active agents including poor aqueous solubility, toxicity, low bioavailability, instability under biological conditions, lack of targeting to the site of action and rapid in vivo degradation.

To combat some of these difficulties, pharmaceutically active agents may be formulated with solubilizing agents which themselves may cause side effects such as hypersensitivity and may require premedication to reduce these side effects. Alternative approaches include encapsulation of the pharmaceutically active agent in liposomes, micelles or polymer matrices or attachment of the pharmaceutically active agent to liposomes, micelles and polymer matrices.

Although these approaches may improve some of the problems associated with the formulation and delivery of pharmaceutically active agents, many still have drawbacks. Oncology drugs can be particularly difficult to formulate and have side effects that may limit the dosage amount and regimen that can be used for treatment. This can result in reduced efficacy of the treatment. For example, taxane drugs such as paclitaxel, docetaxel and cabazitaxel have low aqueous solubility and are often formulated with solubilisation 30. excipients such as polyethoxylated caster oils (Cremophor EL) or polysorbate 80. Although these solubilization excipients allow increased amounts of drug in the formulation, they are known to result in significant side effects themselves including hypersensitivity. To reduce hypersensitivity, premedication with steroids such as dexamethasone is sometimes used in the dosage regimen. However, this also has drawbacks as corticosteroids have side effects and are not able to be used in diabetic patients, which form a significant subset of patients over 50 with breast cancer.

The use of liposomes, micelles and polymer matrices as carriers either encapsulating or having the pharmaceutical agent attached, while allowing solubilisation of the pharmaceutically active agent and in some cases improved bioavailability and targeting, present difficulties in relation to release of the pharmaceutically active agent. In some cases, the carrier degrades rapidly releasing the pharmaceutically active agent before it has reached the target organ. In other cases, the release of the pharmaceutically active agent from the carrier is variable and therefore may not reach a therapeutic dose of drug in the body or in the target organ.

Another difficulty with liposome, micelle and polymer matrices as carriers is that drug loading can be variable. This can result in some batches of a particular composition being effective while others are not and/or difficulties in registration of a product for clinical use because of variability in the product.

In addition these molecules may be unstable or poorly characterised materials, may suffer from polydispersity, and due to their nature be difficult to analyse and characterise. They may also have difficult routes of manufacture. These difficulties, especially with regard to analysis and batch to batch inconsistency, significantly impede the path to regulatory submission and approval.

With pharmaceutically active agents that have poor aqueous solubility, often the delivery method is limited, for example, to parenteral administration. This may limit the dosage regimen available and the dosage that may be delivered.

There is a need for alternative formulations and delivery means for delivering drugs to reduce side effects, improve dosage regimens and improve the therapeutic window which may lead to improvements in compliance and efficacy of the drug in patients.

SUMMARY OF THE INVENTION

The invention is predicated in part on the discovery that macromolecules comprising a dendrimer with surface amino groups having at least two different terminal groups attached to the surface amino groups of the dendrimer and wherein the first terminal group is a pharmaceutically active agent covalently attached to the surface amino group through a diacid linker and the second terminal group is a pharmacokinetic modifying agent may allow high drug loading, improved solubility and controlled release of the pharmaceutically active agent.

In a first aspect of the invention there is provided a macromolecule comprising:
  i) a dendrimer comprising a core and at least one generation of building units, the outermost generation of building units having surface amino groups, wherein at least two different terminal groups are covalently attached to the surface amino groups of the dendrimer;
  ii) a first terminal group which is a residue of a pharmaceutically active agent comprising a hydroxyl group;
  iii) a second terminal group which is a pharmacokinetic modifying agent;
wherein the first terminal group is covalently attached to the surface amino group of the dendrimer through a diacid linker, or a pharmaceutically acceptable salt thereof.

In some embodiments the pharmaceutically active agent is an oncology drug, especially docetaxel, paclitaxel, cabazitaxel, camptothecin, topotecan, irinotecan or gemcitabine. In other embodiments the pharmaceutically active agent is a steroid, especially testosterone. In some embodiments, the pharmaceutically active agent is a sparingly soluble or insoluble in aqueous solution.

In some embodiments the pharmacokinetic modifying agent is polyethylene glycol, especially polyethylene glycol having a molecular weight in the range of 220 to 2500 Da, more especially 570 to 2500 Da. In some embodiments, the polyethylene glycol has a molecular weight between 220 and 1100 Da, especially 570 and 1100 Da. In other embodiments, the polyethylene glycol has a molecular weight between 1000 and 5500 Da or 1000 and 2500 Da, especially 1000 and 2300 Da.

In some embodiments the diacid linker has the formula:

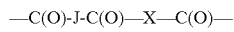

wherein X is selected from —$C_1$-$C_{10}$alkylene-, —$(CH_2)_s$-A-$(CH_2)_t$— and Q;
—C(O)-J- is absent, an amino acid residue or a peptide of 2 to 10 amino acid residues, wherein the —C(O)— is derived from the carboxy terminal of the amino acid or peptide;
A is selected from —O—, —S—, —$NR_1$—, —$N^+(R_1)_2$—, —S—S—, —$[OCH_2CH_2]_r$—O—, —Y—, and —O—Y—O—;
Q is selected from Y or —Z=N—NH—$S(O)_w$—Y—;
Y is selected from cycloalkyl, heterocycloalkyl, aryl and heteroaryl;
Z is selected from —$(CH_2)_x$—C($CH_3$)=, —$(CH_2)_x$CH=, cycloalkyl and heterocycloalkyl;
$R_1$ is selected from hydrogen and $C_1$-$C_4$ alkyl;
s and t are independently selected from 1 and 2;
r is selected from 1, 2 and 3;
w is selected from 0, 1 and 2; and
x is selected from 1, 2, 3 and 4.

In some embodiments the dendrimer has 1 to 8 generations of building units, especially 3 to 6 generations of building units. In some embodiments the dendrimer is a dendrimer comprising building units of lysine or lysine analogues. In other embodiments the dendrimer comprises building units of polyetherhydroxylamine.

In some embodiments the first terminal group and the second terminal group are present in a 1:1 ratio. In some embodiments the macromolecule comprises a third terminal group which is a blocking group, especially an acyl group such as acetate. In some embodiments the ratio of the first terminal group, second terminal group and third terminal group is 1:2:1.

In some embodiments, at least 50% of the terminal groups comprise a first or second terminal group.

In some embodiments the dendrimer comprises a targeting agent attached to a functional group on the core optionally through a spacer group, especially where the targeting agent is selected from luteinising hormone releasing hormone, a luteinising hormone releasing hormone analog such as deslorelin, LYP-1 and an antibody or fragment thereof.

In some embodiments the macromolecule has a particulate size of less than 1000 nm, especially between 5 and 1000 nm, more especially between 5 and 400 nm, most especially between 5 and 50 nm. In some embodiments, the macromolecule has a molecular weight of at least 30 kDa, especially 40 to 300 kDa, more especially 40 to 150 kDa.

In another aspect of the invention there is provided a pharmaceutical composition comprising the macromolecule of the invention and a pharmaceutically acceptable carrier. In some embodiments, the composition is substantially free of solubilisation excipients such as polyethoxylated caster oils (eg: Cremphor EL) and polysorbate 80. By removing the solubilisation excipient the composition of dendrimer is less likely to cause side effects such as acute or delayed hypersensitivity including life-threatening anaphylaxis and/or severe fluid retention.

In some embodiments the macromolecule is formulated as a slow-release formulation. In some embodiments the linker selected to allow controlled-release of pharmaceutically active agent. In some embodiments, the macromolecule is formulated to release greater than 50% of the pharmaceutically active agent in between 5 minutes to 60 minutes. In other embodiments, the macromolecule is formulated to release greater than 50% of the pharmaceutically active agent in between 2 hours and 48 hours. In yet other embodiments, the macromolecule is formulated to release greater than 50% of the pharmaceutically active agent in between 5 days and 30 days.

In another aspect of the invention there is provided a method of treating or suppressing the growth of a cancer comprising administering an effective amount of a macromolecule or pharmaceutical composition of the invention in which the pharmaceutically active agent of the first terminal group is an oncology drug.

In some embodiments, the tumors are primary or metastatic tumors of the prostate, testes, lung, colon, pancreas, kidney, bone, spleen, brain, head and/or neck, breast, gastrointestinal tract, skin or ovary.

In some embodiments, the method comprises administration of a composition of a macromolecule that is substantially free of polyethoxylated caster oils such as Cremophor EL, or polysorbate 80.

In another aspect of the invention there is provided a method of reducing hypersensitivity upon treatment with an oncology drug comprising administering a pharmaceutical composition of the present invention, wherein the composition is substantially free from solubilisation excipients such as Cremophor EL and polysorbate 80.

In a further aspect of the invention there is provided a method of reducing the toxicity of an oncology drug or formulation of an oncology drug, comprising administering a macromolecule of the invention in which the oncology drug is the pharmaceutically active agent of the first terminal group.

In some embodiments, the toxicity that is reduced is hematologic toxicity, neurological toxicity, gastrointestinal toxicity, cardiotoxicity, hepatotoxicity, nephrotoxicity, ototoxicity or encephalotoxicity.

In yet a further aspect of the invention there is provided a method of reducing side effects associated with an oncology drug or formulation of an oncology drug, comprising administering a macromolecule of the invention in which the oncology drug is the pharmaceutically active agent of the first terminal group.

In some embodiments, the side effects which are reduced are selected from neutropenia, leukopenia, thrombocytopenia, myelotoxicity, myelosuppression, neuropathy, fatigue, non-specific neurocognitive problems, vertigo, encephalopathy, anemia, dysgeusia, dyspnea, constipation, anorexia, nail disorders, fluid retention, asthenia, pain, nausea, vomiting mucositis, alopecia, skin reactions, myalgia, hypersensitivity and anaphylaxis.

In some embodiments, the need for premedication with agents such as corticosteroids and anti-histamines is reduced or eliminated.

In yet another aspect of the invention there is provided a method of treating or preventing a disease or disorder related to low testosterone levels comprising administering a macromolecule or pharmaceutical composition of the invention in which the pharmaceutically active agent is testosterone.

In some embodiments, the composition is formulated for transdermal delivery, especially by transdermal patch optionally having microneedles.

DESCRIPTION OF THE INVENTION

A singular forms "a", "an" and "the" include plural aspects unless the context clearly indicates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "alkyl" refers to a straight chain or branched saturated hydrocarbon group having 1 to 10 carbon atoms. Where appropriate, the alkyl group may have a specified number of carbon atoms, for example, $C_{1-4}$alkyl which includes alkyl groups having 1, 2, 3 or 4 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, 4-methylbutyl, n-hexyl, 2-methylpentyl, 3-methylpentyl, 4-methylpentyl, 5-methylpentyl, 2-ethylbutyl, 3-ethylbutyl, heptyl, octyl, nonyl and decyl.

The term "alkylene" as used herein refers to a straight-chain divalent alkyl group having 1 to 10 carbon atoms. Where appropriate, the alkylene group may have a specified number of carbon atoms, for example $C_1$-$C_6$ alkylene includes —$CH_2$—, —$(CH_2)_2$—, —$(CH_2)_3$—, —$(CH_2)_4$—, —$(CH_2)_5$ and —$(CH_2)_6$—.

As used herein, the term "cycloalkyl" refers to a saturated or unsaturated cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentanyl, cyclopentenyl, cyclohexanyl, cyclohexenyl, 1,4-cyclohexadienyl, cycloheptanyl and cyclooctanyl.

As used herein, the term "aryl" is intended to mean any stable, monocyclic or bicyclic carbon ring of up to 7 atoms in each ring, wherein at least one ring is aromatic. Examples of such aryl groups include, but are not limited to, phenyl, naphthyl, tetrahydronaphthyl, indanyl, biphenyl and binaphthyl.

The term "heterocycloalkyl" or "heterocyclyl" as used herein, refers to a cyclic hydrocarbon in which one to four carbon atoms have been replaced by heteroatoms independently selected from the group consisting of N, N(R), S, S(O), S(O)$_2$ and O. A heterocyclic ring may be saturated or unsaturated. Examples of suitable heterocyclyl groups include tetrahydrofuranyl, tetrahydrothiophenyl, pyrrolidinyl, pyrrolinyl, pyranyl, piperidinyl, pyrazolinyl, dithiolyl, oxathiolyl, dioxanyl, dioxinyl, morpholino and oxazinyl.

The term "heteroaryl" as used herein, represents a stable monocyclic or bityclic ring of up to 7 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, quinoxalinyl, quinazolinyl, pyrazolyl, indolyl, benzotriazolyl, furanyl, thienyl, thiophenyl, 3,4-propylenedioxythiophenyl, benzothienyl, benzofuranyl, benzodioxane, benzodioxin, quinolinyl, isoquinolinyl, oxazolyl, isoxazolyl, imidazolyl, pyrazinyl, pyridazinyl, pyridinyl, pyrimidinyl, pyrrolyl, tetrahydroquinoline, thiazolyl, isothiazolyl, 1,2,4-triazolyl, 1,2,3-triazolyl, 1,2,4-oxadiazolyl, 1,2,4-thiadiazolyl, 1,3,5-triazinyl, 1,2,4-triazinyl, 1,2,4,5-tetrazinyl and tetrazolyl.

The term "dendrimer" refers to a molecule containing a core and at least one dendron attached to the core. Each dendron is made up of at least one layer or generation of branched building units resulting in a branched structure with increasing number of branches with each generation of building units. The maximum number of dendrons attached to the core is limited by number of functional groups on the core. The core may have one or more functional groups suitable to bear a dendron and optionally an additional functional group for attachment of an agent suitable for targeting a specific organ or tissue, signalling or imaging.

The term "building unit" used herein refers to a branched molecule having at least three functional groups, one for attachment to the core or a previous generation of building units and at least two functional groups for attachment to the next generation of building units or forming the surface of the dendrimer molecule.

The term "generation" refers to the number of layers of building units that make up a dendron or dendrimer. For example, a one generation dendrimer will have one layer of branched building units attached to the core, for example, Core-[[building unit]]$_u$, where u is the number of dendrons attached to the core. A two generation dendrimer has two layers of building units in each dendron attached to the core, for example, when the building unit has one branch point, the dendrimer may be: Core[[building unit][building unit]$_2$]$_u$, a three generation dendrimer has three layers of building units in each dendron attached to the core, for example Core-[[building unit][building unit]$_2$[building unit]$_4$]$_u$, a 6 generation dendrimer has six layers of building units attached to the core, for example, Core-[[building unit][building unit]$_2$[building unit]$_4$[building unit]$_8$[building unit]$_{16}$[building unit]$_{32}$]$_u$, and the like. The last generation of building units (the outermost generation) provides the surface functionalisation of the dendrimer and the number of functional groups available for binding terminal groups. For example, in a dendrimer having a core with two dendrons attached (u=2), if each building unit has one branch point and there are 6 generations, the outermost generation has 64 building units and 128 functional groups available to bind terminal groups.

The term "sparingly soluble" as used herein refers to a drug or pharmaceutically active agent that has a solubility between 1 mg/mL and 10 mg/mL in water. Drugs that have a solubility in water of less than 1 mg/mL are considered insoluble.

The term "pharmaceutically active agent" as used herein refers to a compound that is used to exert a therapeutic effect in vivo. This term is used interchangeably with the term "drug". The term "residue of a pharmaceutically active agent" refers to the portion of the macromolecule that is a pharmaceutically active agent when the pharmaceutically active agent has been modified by attachment to the macromolecule.

The term "oncology drug" used herein refers to a pharmaceutically active agent used to treat cancer, such as a chemotherapy drug.

As used herein, the term "solubilisation excipient" refers to a formulation additive that is used to solubilize insoluble or sparingly soluble drugs into an aqueous formulation. Examples include surfactants such as polyethoxylated caster oils including Cremophor EL, Cremophor RH 40 and Cremophor RH 60, D-α-tocopherol-polyethylene-glycol 1000 succinate, polysorbate 20, polysorbate 80, solutol HS 15, sorbitan monoleate, poloxamer 407, Labrasol and the like.

The macromolecules of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quarternized with such agents as lower alkyl halide, such as methyl, ethyl, propyl, and butyl chlorides, bromides and iodides; dialkyl sulfates like dimethyl and diethyl sulfate; and others.

Macromolecules of the Invention

The macromolecules of the invention comprise:
i) a dendrimer comprising a core and at least one generation of building units, the outermost generation of building units having surface amino groups, wherein at least two different terminal groups are covalently attached to the surface amino groups of the dendrimer,
ii) a first terminal group which is a residue of a pharmaceutically active agent comprising a hydroxyl group;
iii) a second terminal group which is a pharmacokinetic modifying agent;
wherein the first terminal group is covalently attached to the surface amino group of the dendrimer through a diacid linker, or a pharmaceutically acceptable salt thereof.

The dendrimers having surface amino groups have at least two different terminal groups covalently attached to the surface amino groups.

The first terminal group is a residue of a pharmaceutically active agent comprising a free hydroxyl group. The pharmaceutically active agent is attached to the surface amino group of the dendrimer through a diacid linker. The diacid linker forms an ester bond with the hydroxyl group of the pharmaceutically active agent and an amide bond with the surface amino group.

The pharmaceutically active agent may be any pharmaceutically active agent that has a hydroxyl group available for ester formation with the diacid linker and is administered to a subject to produce a therapeutic effect.

In some embodiments the pharmaceutically active agent is an oncology drug such as a taxane, a nucleoside or a kinase inhibitor, a steroid, an opioid analgesic, a respiratory drug, a central nervous system (CNS) drug, a hypercholesterolemic drug, an antihypertensive drug, an immunosuppressive drug, an antibiotic, a luteinising hormone releasing hormone (LHRH) agonist, a LHRH antagonist, an antiviral drug, an antiretroviral drug, an estrogen receptor modulator, a somatostatin mimic, an anti-inflammatory drug, a vitamin $D_2$ analogue, a synthetic thyroxine, an antihistamine, an antifungal agent or a nonsteroidal anti-inflammatory drug (NSAID).

Suitable oncology drugs include taxanes such as paclitaxel, cabazitaxel and docetaxel, camptothecin and its analogues such as irinotecan and topotecan, other antimicrotubule agents such as vinflunine, nucleosides such as gemcitabine, cladribine, fludarabine capecitabine, decitabine, azacitidine, clofarabine and nelarabine, kinase inhibitors such as sprycel, temisirolimus, dasatinib, AZD6244, AZD1152, PI-103, R-roscovitine, olomoucine and purvalanol A, and epothilone B analogues such as Ixabepilone, anthrocyclines such as amrubicin, doxorubicin, epirubicin and valrubicin, super oxide inducers such as trabectecin, proteosome inhibitors such as bortezomib and other topoisomerase inhibitors, intercalating agents and alkylating agents.

Suitable steroids include anabolic steroids such as testosterone, dihydrotestosterone and ethynylestradiol, and corticosteroids such as cortisone, prednisilone, budesonide, triamcinolone, fluticasone, mometasone, amcinonide, flucinolone, fluocinanide, desonide, halcinonide, prednicarbate, fluocortolone, dexamethasone, betamethasone and fluprednidine.

Suitable opioid analgesics include morphine, oxymorphone, naloxone, codeine, oxycodone, methylnaltrexone, hydromorphone, buprenorphine and etorphine.

Suitable respiratory drugs include bronchodilators, inhaled steroids, and decongestants and more particularly salbutamol, ipratropium bromide, montelukast and formoterol.

Suitable CNS drugs include antipsychotic such as quetiapine and antidepressants such as venlafaxine.

Suitable drugs to control hypercholesterolemia include ezetimibe and statins such as simvastatin, lovastatin, atorvastatin, fluvastatin, pitavastatin, provastatin and rosuvastatin.

Suitable antihypertensive drugs include losartan, olmesartan, medoxomil, metrolol, travoprost and bosentan.

Suitable immunosuppressive drugs include glucocorticoids, cytostatics, antibody fragments, anti-immunophilins, interferons, TNF binding proteins and more particularly, cacineurin inhibitors such as tacrolimus, mycophenolic acid and its derivatives such as mycophenolate mofetil, and cyclosporine.

Suitable antibacterial agents include antibiotics such as amoxicillin, meropenem and clavulanic acid.

Suitable LHRH agonists include goserelin acetate, deslorelin and leuprorelin.

Suitable LHRH antagonists include cetrorelix, ganirelix, abarelix and degarelix.

Suitable antiviral agents include nucleoside analogs such as lamivudine, zidovudine, abacavir and entecavir and suitable antiretroviral drugs include protease inhibitors such as atazanavir, lapinavir and ritonavir.

Suitable selective estrogen receptor modulators include raloxifene and fulvestrant.

Suitable somastatin mimics include octreotide.

Suitable anti-inflammatory drugs include mesalazine and suitable NSAIDs include acetaminophen (paracetamol).

Suitable vitamin $D_2$ analogues include paricalcitol.

Suitable synthetic thyroxines include levothyroxine.

Suitable anti-histamines include fexofenadine.

Suitable antifungal agents include azoles such as viriconazole.

In some embodiments the pharmaceutically active agent is sparingly soluble or insoluble in aqueous solution.

In particular embodiments the pharmaceutically active agent is selected from docetaxel, paclitaxel, testosterone, gemcitabine, camptothecin, irinotecan and topotecan, especially docetaxel, paclitaxel and testosterone.

The diacid linker that links the pharmaceutically active agent to the surface amino groups of the dendrimer have the formula:

—C(O)-J-C(O)—X—C(O)— wherein X is selected from —$C_1$-$C_{10}$alkylene-, —$(CH_2)_s$-A-$(CH_2)_t$— and Q;

—C(O)-J- is absent, an amino acid residue or a peptide of 2 to 10 amino acid residues, wherein the —C(O)— is derived from the carboxy terminal of the amino acid or peptide;
A is selected from —O—, —S—, —NR$_1$—, —N$^+$(R$_1$)$_2$—, —S—S—, —[OCH$_2$CH$_2$]$_r$—O—, —Y—, and —O—Y—O—;
Q is selected from Y or —Z=N—NH—S(O)$_w$—Y—;
Y is selected from cycloalkyl, heterocycloalkyl, aryl and heteroaryl;
Z is selected from —(CH$_2$)$_x$—C(CH$_3$)=, —(CH$_2$)$_x$CH=, cycloalkyl and heterocycloalkyl;
R$_1$ is selected from hydrogen and C$_1$-C$_4$ alkyl;
s and t are independently selected from 1 and 2;
r is selected from 1, 2 and 3;
w is selected from 0, 1 and 2; and
x is selected from 1, 2, 3 and 4.

In some embodiments one or more of the following applies:
X is —C$_1$-C$_6$-alkylene, —CH$_2$-A-CH$_2$—, —CH$_2$CH$_2$-A-CH$_2$CH$_2$— or heteroaryl;
—C(O)-J is absent, an amino acid residue or a peptide of 2 to 6 amino acid residues, wherein the —C(O)— is derived from the carboxy terminal of the amino acid or peptide;
A is selected from —O—, —S—, —S—S—, —NH—, —N(CH$_3$)—, —N$^+$(CH$_3$)$_2$—, —O-1,2-phenyl-O—, —O-1,3-phenyl-O—, —O-1,4-phenyl-O—, —OCH$_2$CH$_2$O—, —[OCH$_2$CH$_2$]$_2$—O— and —[OCH$_2$CH$_2$]$_3$—O—;
Y is heteroaryl or aryl, especially thiophenyl, 3,4-propylenedioxythiophenyl or benzene;
Z is —(CH$_2$)$_x$C(CH$_3$)=, —(CH$_2$)$_x$CH= and cycloalkyl, especially —CH$_2$CH$_2$C(CH$_3$)=, —CH$_2$CH$_2$CH$_2$C(CH$_3$)=, —CH$_2$CH$_2$CH$_2$CH=, cyclopentyl and cyclohexyl;
R$_1$ is hydrogen, methyl or ethyl, especially hydrogen or methyl, more especially methyl;
one of s and t is 1 and the other is 1 or 2, especially were both s and t are 1;
r is 1 or 2, especially 2;
w is 1 or 2, especially 2; and
x is 2 or 1, especially 3.

In some embodiments, —C(O)-J- is absent. In other embodiments, —C(O)-J- is an amino acid residue or a peptide having 2 to 6 amino acid residues. In these embodiments, the N-terminus of the amino acid or peptide forms an amide bond with the —C(O)—X—C(O)— group. In some embodiments, the peptide is a peptide that comprises an amino acid sequence that is recognised and cleaved by an endogenous enzyme, such as a protease. In some embodiments, the enzyme is an intracellular enzyme. In other embodiments, the enzyme is an extracellular enzyme. In particular embodiments, the enzyme is one that is present in or around neoplastic tissue, such as tumor tissue. In some embodiments, the peptide is recognised by capthesin B or a metalloprotease such as a neutral metalloproteinase (NMP), MMP-2 and MMP-9. Exemplary peptides include GGG, GFLG and GILGVP.

In particular embodiments the diacid linker is selected from:

—C(O)—CH$_2$CH$_2$—C(O)—,

—C(O)—CH$_2$CH$_2$CH$_2$—C(O)—,

—C(O)—CH$_2$OCH$_2$—C(O)—,

—C(O)—CH$_2$SCH$_2$—C(O)—,

—C(O)CH$_2$NHCH$_2$—C(O)—,

—C(O)—CH$_2$N(CH$_3$)CH$_2$—C(O)—,

—C(O)—CH$_2$N$^+$(CH$_3$)$_2$CH$_2$—C(O)—,

—C(O)—CH$_2$—S—S—CH$_2$—C(O)—,

—C(O)—OCH$_2$CH$_2$OCH$_2$CH$_2$OC(O)—,

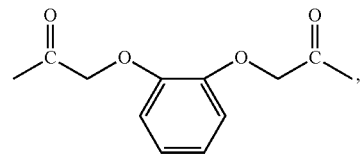

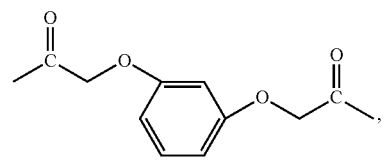

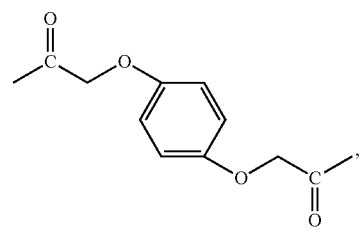

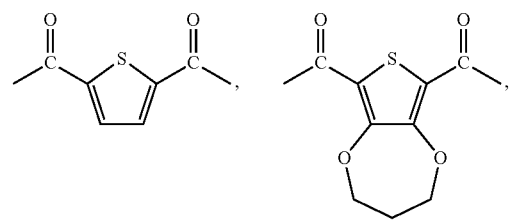

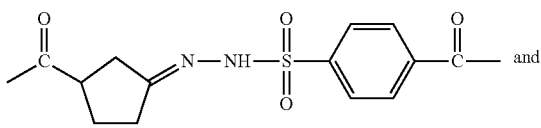 and

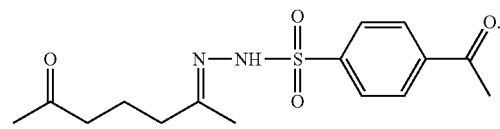

In other embodiments, the diacid linker also comprises a peptide. Exemplary diacid linkers include:
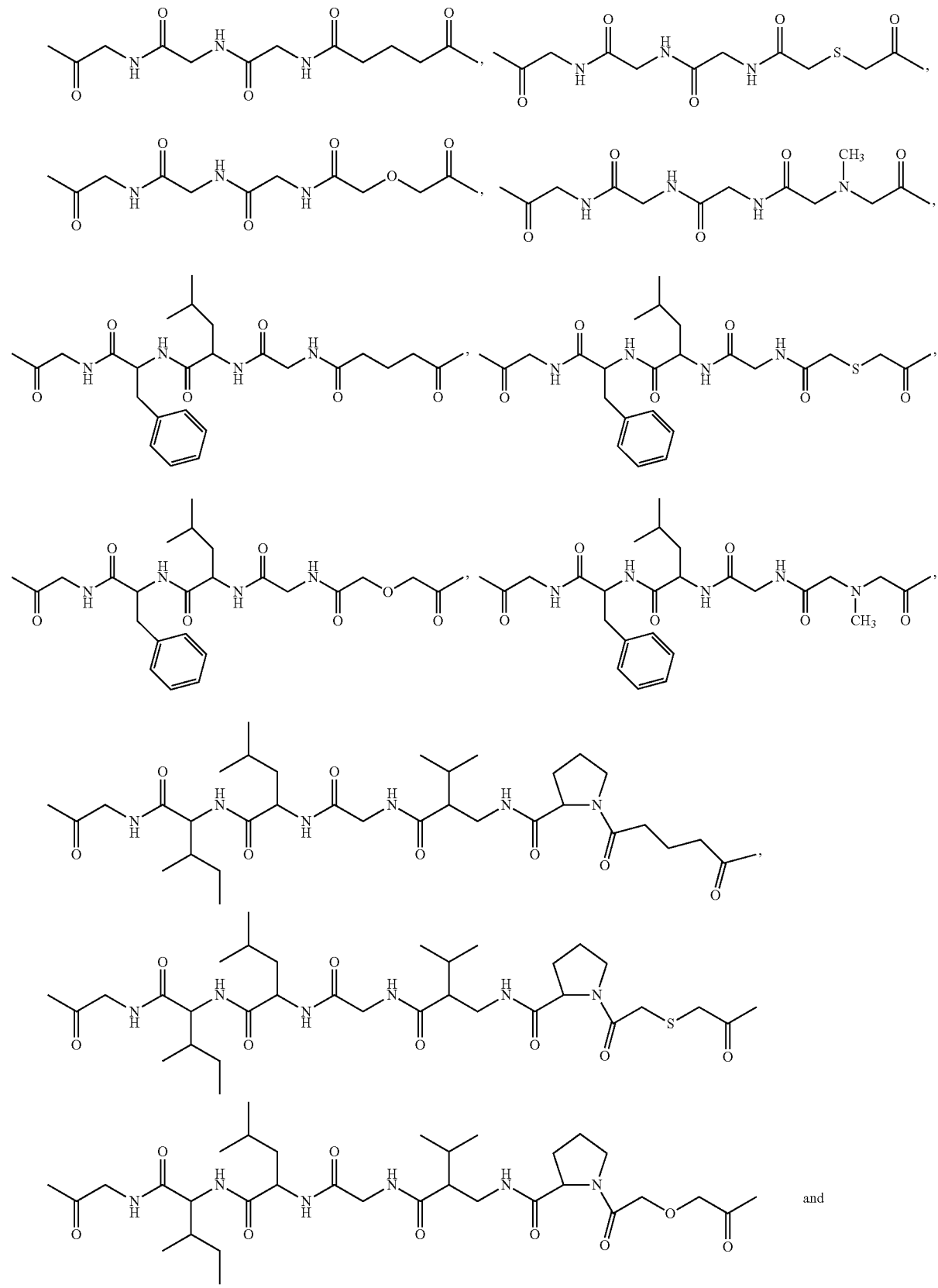
and

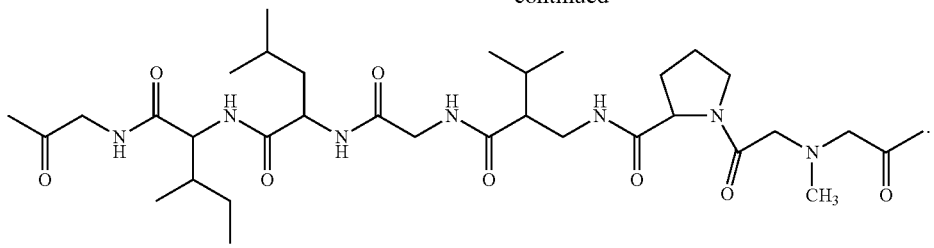

In some embodiments, the diacid linker is selected to provide a desired rate of release of the drug. For example, a rapid release may be required where the entire load of pharmaceutical agent is required in a short space of time whereas a slow release may be more suitable when a low constant therapeutic dose of pharmaceutically active agent is required.

In some embodiments, the rate of release is faster than the drug delivered independent of the macromolecule, especially at least twice as fast. In some embodiments, the drug is released more slowly than the drug independent of the macromolecule, especially where the drug is released at least two times slower, more especially the drug is released at least 10 times slower. In some embodiments, the drug is released at least 30 times slower as described in Example 39. Low rates of release may be particularly suitable where the macromolecule includes a targeting group, to enable release of the drug at the active site, but not in plasma. Low rates of release may also be suitable for drugs formulated to enable slow controlled release delivery over long periods of time, such as between 1 week and 6 months. The drug may be released from the macromolecule over a prolonged period of time, such as days, weeks or months. Fast release is preferably release greater than 50% within 0 to 480 minutes, especially within 0 to 120 minutes, and more especially within 5 to 60 minutes. Medium release preferably is release greater than 50% within 1 to 72 hours, especially within 2 to 48 hours. Slow release is preferably release of greater than 50% in greater than 2 days, especially 2 days to 6 months, and more especially within 5 days to 30 days.

The rate of release of the drug can be controlled by the selection of the diacid linker. Diacid linkers containing one or more oxygen atoms in their backbones, such as diglycolic acid, phenylenedioxydiacetic acid, and polyethylene glycol, or with a cationic nitrogen atom, tend to release drug at a rapid rate, diacid linkers having one sulfur atom in their backbone, such as thiodiacetic acid, have a medium rate of release and diacid linkers having one or more nitrogen atoms, two or more sulfur atoms, alkyl chains or heterocyclic or heteroaryl groups release the drug at a slow rate. The rate of release may be summarized by one or more —O—>—N$^+$(R$_1$)$_2$—>one    —S—>one    —NR—>—N—NH—SO$_2$—>—S—S—>-alkyl->-heterocyclyl-.

It can be seen from Table 2, studies of macromolecules in plasma samples that the diglycolic acid (Experiment 3 (b)) released docetaxel at fast rate, with a half life of less than 22 hours, thiodiacetic acid linker (Experiment 8 (c)) released docetaxel at a medium rate, with a half life of a little more than 22 hours, extrapolated to around 24 to 30 hours and the glutaric acid linker (Experiment 5 (b)) released docetaxel at a slow rate with a half life of much greater than 22 hours, and predicted to be more than 2 days. Experiment 16 and 17 do not substantially release docetaxel in plasma but allow the macromolecule to be targeted to a tumor in which proteases can cleave the peptide sequence to provide the docetaxel at the site of action.

The rate of release may also be dependent on the identity of the pharmaceutically active agent.

In some embodiments, each pharmaceutically active agent is attached to the dendrimer with the same diacid linker. In other embodiments, two or more different diacid linkers are used allowing the pharmaceutically active agent to be released from the macromolecule at different rates.

The second terminal group is a pharmacokinetic modifying agent, which may be any molecule or residue thereof that modifies or modulates the pharmacokinetic profile of the pharmaceutically active agent or the macromolecule including absorption, distribution, metabolism and/or excretion. In a particular embodiment, the pharmacokinetic modifying agent is an agent selected to prolong the plasma half-life of the pharmaceutically active agent, such that the macromolecule has a half life that is greater than the half-life of the native pharmaceutically active agent, or the marketed pharmaceutically active agent in a non-dendrimer formulation. Preferably the half life of the macromolecule or composition is at least 2 times and more preferably 10 times greater than the native pharmaceutically active agent, or the marketed pharmaceutically active agent in a non-dendrimer formulation.

In some embodiments, the second terminal group is polyethylene glycol (PEG), a polyalkyloxazoline such as polyethyloxazoline (PEOX), polyvinylpyrolidone and polypropylene glycol, especially PEG. In other embodiments, the second terminal group is a polyether dendrimer.

In some embodiments, the PEG has a molecular weight of between 220 and 5500 Da. In some embodiments, the PEG has a molecular weight of 220 to 1100 Da, especially 570 and 1100 Da. In other embodiments, the PEG has a molecular weight of 1000 to 5500 Da, especially 1000 to 2500 Da or 1000 to 2300.

In some embodiments, the macromolecule comprises a third terminal group. The third terminal group is a blocking group that serves to block the reactivity of a surface amino group of the dendrimer. In particular embodiments, the blocking group is an acyl group such as a C$_2$-C$_{10}$ acyl group, especially acetyl. In other embodiments, the third terminal group is a second pharmaceutically active agent or a targeting agent.

In some embodiments where there is a first terminal group and a second terminal group, the ratio of first terminal group and second terminal group is between 1:2 and 2:1, especially 1:1.

In some embodiments where there is a first terminal group, a second terminal group and a third terminal group, the ratio is 1:1:1 to 1:2:2, especially 1:2:1.

In some embodiments, not all of the surface amino groups of the dendrimer are bound to a first terminal group, a second terminal group, or a third terminal group. In some embodiments, some of the surface amino groups remain free amino groups. In some embodiments at least 50% of the total terminal groups comprise one of a pharmacokinetic modifying agent or a pharmaceutically active agent, especially at least 75% or at least 80% of the terminal groups comprise one of a pharmacokinetic modifying agent or a pharmaceutically active agent. In particular embodiments, a pharmaceutically active agent is bound to greater than 14%, 25%, 27%, 30% 39%, 44% or 48% of the total number of surface amino groups. Where dendrimer is a G5 polylysine dendrimer, the total number of the pharmaceutically active agent is preferably greater than 15, and especially greater than 23 and more especially greater than 27. In some embodiments, the pharmacokinetic modifying agent is bound to greater than 15%, 25%, 30%, 33% or 46% of the total number of surface amino groups. Where dendrimer is a G5 polylysine dendrimer, the total number of pharmacokinetic modifying agents is preferably greater than 25, and especially greater than 30.

The macromolecule of the invention comprises a dendrimer in which the outermost generation of building units has surface amino groups. The identity of the dendrimer of the macromolecule is not particularly important, provided it has surface amino groups. For example, the dendrimer may be a polylysine, polylysine analogue, polyamidoamine (PAMAM), polyethyleneimine (PEI) dendrimer or polyether hydroxylamine (PEHAM) dendrimer.

The dendrimer comprises a core and one or more dendrons made of one or more building units. The building units are built up in layers referred to as generations.

In some embodiments, the building unit is a polyamine, more preferably a di or tri-amino with a single carboxylic acid. Preferably the molecular weight of the building unit is from 110 Da to 1 KDa. In some embodiments, the building unit is lysine or lysine analogue selected from:

Lysine 1: having the structure:

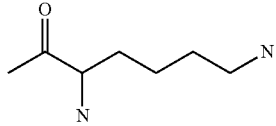

1

Glycyl-Lysine 2 having the structure:

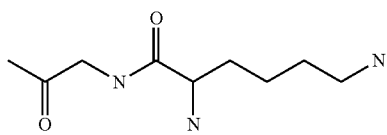

2

Analogue 3, having the structure below, where a is an integer of 1 or 2; b and c are the same or different and are integers of 1 to 4:

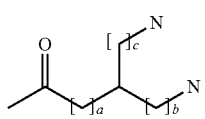

3

Analogue 4, having the structure below, where a is an integer of 0 to 2; b and c are the same or different and are integers of 2 to 6:

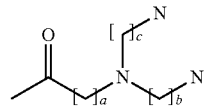

4

Analogue 5, having the structure below, where a is an integer of 0 to 5; b and c are the same or different and are integers of 1 to 5:

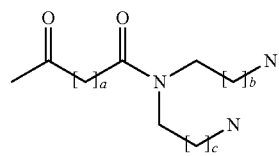

5

Analogue 6, having the structure below, where a is an integer of 0 to 5; b and c are the same or different and are integers of 0 to 5:

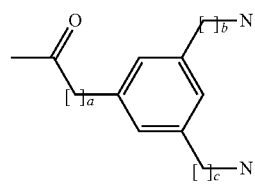

6

Analogue 7, having the structure below, where a is an integer of 0 to 5; b and c are the same or different and are integers of 1 to 5:

7

Analogue 8, having the structure below, where a is an integer of 0 to 5; b, c and d are the same or different and are integers of 1 to 5:

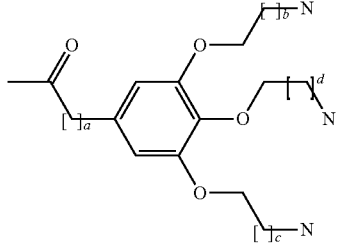

Analogue 9, having the structure below, where a is an integer of 0 to 5; b and c are the same or different and are integers of 1 to 5:

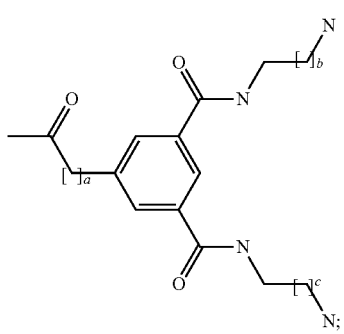

and furthermore, the alkyl chain moieties (eg: —C—C—C—) of the building units may be understood to include alkoxy fragments such as C—O—C or C—C—O—C—C where one or more non-adjacent carbon atom is replaced with an oxygen atom, provided that such a substitution does not form a O—C—X group where X is O or N.

In some embodiments the building unit is an amidoamine building unit with the structure 10:

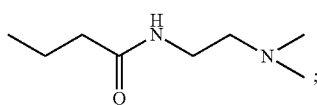

an etherhydroxyamine building unit with the structure 11:

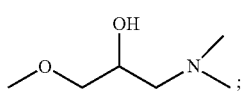

or a propyleneimine building unit with the structure 12:

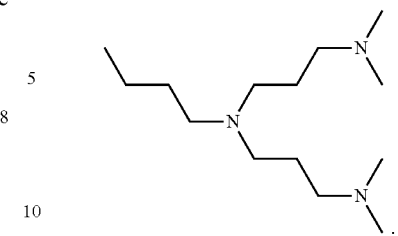

In a preferred aspect of the invention, the building units are selected from Lysine 1, Glycyl-Lysine 2 or Lysine analogue 5:

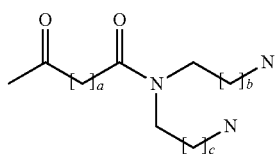

where a is an integer of 0 to 2 or the alkyl link is C—O—C; b and c are the same or different and are integers of 1 to 2; especially where the building units are lysine.

In some embodiments, the core is a monoamine compound, diamine compound, triamine compound, tetraamine compound or pentamine compound, one or more of the amine groups having a dendron comprising building units attached thereto. In particular embodiments, the molecular weight of the building unit is from 110 Da to 1 KDa.

Suitable cores include benzhydrylamine (BHA), a benzhydrylamide of lysine (BHALys) or a lysine analogue, or:

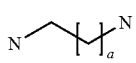

where a is an integer of 1 to 9, preferably 1 to 5;

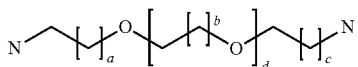

where a, b and c, which may be the same or different, and are integers of 1-5, and d is an integer from 0-100, preferably 1-30;

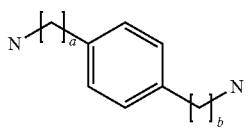

where a and b, may be the same or different, and are integers of 0 to 5;

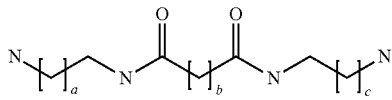

16 where a and c, which may be the same or different, are integers of 1 to 6 and where c is an integer from 0 to 6;

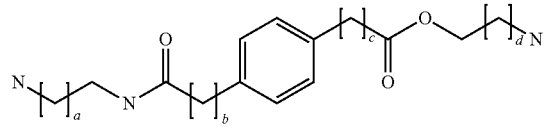

17 where a and d, which may be the same or different, are integers of 1 to 6 and where b and c, which may be the same or different, are integers from 0 to 6;

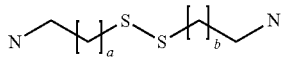

18 where a and b are the same or different and are integers of 1 to 5, especially 1 to 3, more especially 1;

a triamine compound selected from:

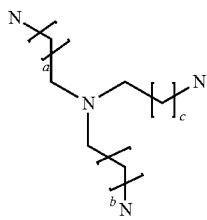

19 where a, b and c, which may be the same or different, are integers of 1 to 6;

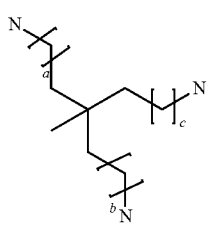

20 where a, b and c, which may be the same or different, are integers of 0 to 6;

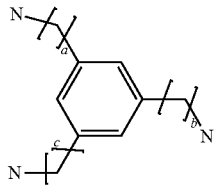

21

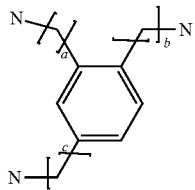

22

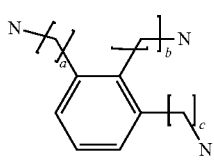

23 where a, b and c, which may be the same or different, are integers of 0 to 6;

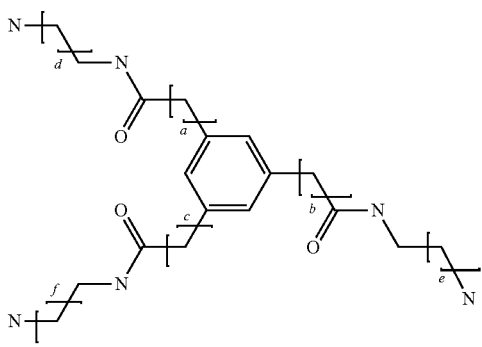

24 where a, b and c, which may be the same or different, are integers of 0 to 6; and d, e and f, which may be the same or different, are integers of 1 to 6;

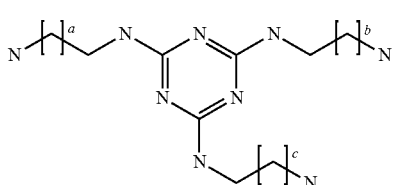

25 where a, b and c, which may be the same or different, are integers of 1 to 6;

26

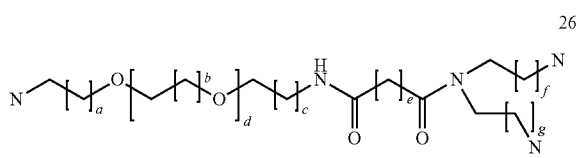

wherein a, b and c, which may be the same or different, are integers of 1 to 5, d is an integer from 1 to 100, preferably 1 to 30, e is an integer from 0 to 5 and f and g are the same or different and are integers from 1 to 5;

or a tetraamine compound selected from

27

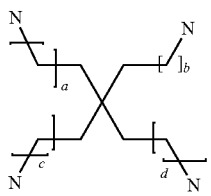

where a, b, c and d, which may be the same or different, are integers of 0 to 6;

28

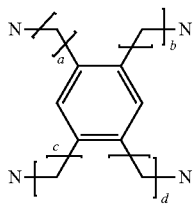

where a, b, c and d, which may be the same or different, are integers of 1 to 6;

29

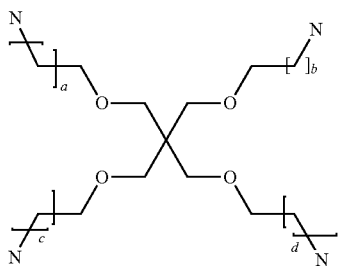

where a, b, c and d, which may be the same or different, are integers of 1 to 6;

30

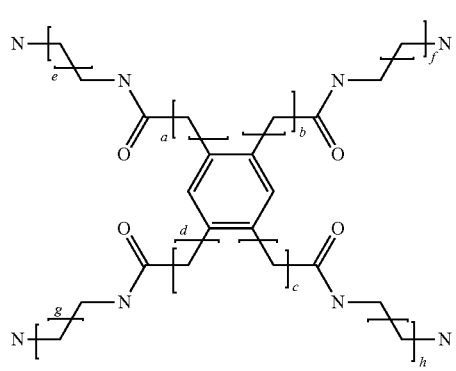

where a, b, c and d, which may be the same or different, are integers of 0 to 6; and e, f, g and h, which may be the same or different, are integers of 1 to 6;

and furthermore, the alkyl chain moieties (eg: —C—C—C—) of the building units may be understood to include alkoxy fragments such as C—O—C or C—C—O—C—C where one or more non-adjacent carbon atom is replaced with an oxygen atom, provided that such a substitution does not form a O—C—X group where X is O or N.

In some embodiments, the core has at least two amino functional groups, one of which has attached a targeting moiety either directly or through a spacer group. At least one of the remaining functional groups of the core having a dendron attached as described in WO 2008/017125.

The targeting agent is an agent that binds to a biological target cell, organ or tissue with some selectivity thereby assisting in directing the macromolecule to a particular target in the body and allowing its accumulation at that target cell, organ or tissue. The targeting group may in addition provide a mechanism for the macromolecule to be actively taken into the cell or tissue by receptor mediated endocytosis.

Particular examples include lectins and antibodies and other ligands (including small molecules) for cell surface receptors. The interaction may occur through any type of bonding or association including covalent, ionic and hydrogen bonding, Van der Waals forces.

Suitable targeting groups include those that bind to cell surface receptors, for example, the folate receptor, adrenergic receptor, growth hormone receptor, luteinizing hormone receptor, estrogen receptor, epidermal growth factor receptor, fibroblast growth factor receptor (eg FGFR2), IL-2 receptor, CFTR and vascular epithelial growth factor (VEGF) receptor.

In some embodiments, the targeting agent is luteinising hormone releasing hormone (LHRH) or a derivative thereof that binds to luteinising hormone releasing hormone receptor. LHRH has the sequence: pyroGlu-His-Trp-Ser-Tyr-Gly-Leu-Arg-Pro-Gly-NH$_2$. Suitable derivatives of LHRH include those in which one of residues 4-7 are replaced by another amino acid, especially residue 6 (Gly). In some embodiments, the replacement amino acid residue is suitably one that has a side chain capable of forming a bond with the core or with the spacer. In some embodiments the derivative is LHRH Gly6Lys, LHRH Gly6Asp or LHRH Gly6Glu, especially LHRH Gly6Lys. In other embodiments, the derivative is LHRH Gly6Trp (deslorelin). This receptor is often found or overexpressed in cancer cells, especially in breast, prostate, ovarian or endometrial cancers.

In some embodiments, the targeting agent is LYP-1, a peptide that targets the lymphatic system of tumors but not the lymphatic system of normal tissue. LYP-1 is a peptide having the sequence H-Cys-Gly-Asn-Lys-Arg-Thr-Arg-Gly-Cys-OH and in which the peptide is in cyclic form due to a disulfide bond between the sulphur atoms of the two cysteine residues.

In some embodiments, the targeting agent may be an RGD peptide. RGD peptides are peptides containing the sequence -Arg-Gly-Asp-. This sequence is the primary integrin recognition site in extracellular matrix proteins.

Antibodies and antibody fragments such as scFvs and diabodies known to interact with receptors or cellular factors include CD20, CD52, MUC1, Tenascin, CD44, TNF-R, especially CD30, HER2, VEGF, EGF, EFGR and TNF-α.

In some embodiments the targeting agent may be folate. Folate is a vitamin that is essential for the biosynthesis of nucleotide bases and is therefore required in high amounts in proliferating cells. In cancer cells, this increased requirement for folic acid is frequently reflected in an overexpression of the folate receptor which is responsible for the transport of folate across the cell membrane. In contrast, the uptake of folate into normal cells is facilitated by the reduced folate carrier, rather than the folate receptor. The folate receptor is upregulated in many human cancers, including malignancies of the ovary, brain, kidney, breast, myeloid cells and the lung and the density of folate receptors on the cell surface appears to increase as the cancer develops.

Estrogens may also be used to target cells expressing estrogen receptor.

The targeting agent may be bound to the dendrimer core directly or preferably through a spacer. The spacer group may be any divalent group capable of binding to both the functional group of the core and the functional group on the targeting agent. The size of the spacer group is preferably sufficient to prevent any steric crowding. Examples of suitable spacer groups include alkylene chains and alkylene chains in which one or more carbon atoms is replaced by a heteroatom selected from —O—, —S—, or NH. The alkylene chain terminates with functional groups suitable for attachment to both the core functional group and the targeting agent. Exemplary spacer groups include X—$(CH_2)_p$—Y, X—$(CH_2O)_p$—$CH_2$—Y, X—$(CH_2CH_2O)_p$—$CH_2CH_2$—Y and X—$(CH_2CH_2CH_2O)_p CH_2CH_2CH_2$—Y, where X and Y are functional groups for binding with or bound to the core and the targeting agent respectively, and p is an integer from 1 to 100, especially 1 to 50 or 1 to 25.

In some embodiments, the targeting group may be bound to the surface amino groups as third functional group. In some embodiments, 1 to 32 targeting groups are bound to the surface, especially, 1 to 10 are bound, more especially 1 to 4 are bound.

In some embodiments, the targeting agent and the spacer group are modified to facilitate reaction. For example, the spacer group may include an azide functional group and the targeting agent may include an alkyne group or the spacer group is modified with an alkyne and the targeting agent modified with an azide and the two groups are conjugated using a click reaction.

In some embodiments the functional group of the core that does not bear a dendron may be bound to biotin, optionally through a spacer group described above, and the macromolecule reacted with an avidin-antibody or avidin-biotin-antibody complex. Each avidin complex may bind up to 4 macromolecule-biotin conjugates or a combination of macromolecule-biotin conjugates and antibody-biotin conjugates.

In particular embodiments, the core is BHA or BHALys or NEOEOEN[SuN(PN)$_2$].

In some embodiments, the dendrimer has 1 to 5 dendrons attached to the core, especially 2 to 4 dendrons, more especially 2 or 3 dendrons.

In some embodiments, the dendrimer has 1 to 8 generations of building units, especially 2 to 7 generations, 3 to 6 generations, more especially 4 to 6 generations.

The macromolecule of the invention may be nanoparticulate having a particulate diameter of below 1000 nm, for example, between 5 and 1000 nm, especially 5 and 500 nm, more especially 5 to 400 nm, such as 5 to 50 nm, especially between 5 and 20 nm. In particular embodiments, the composition contains macromolecules with a mean size of between 5 and 20 nm. In some embodiments, the macromolecule has a molecular weight of at least 30 kDa, for example, 40 to 150 kDa or 40 to 300 kDa.

In some embodiments, the macromolecules of the invention have a particle size that is suitable for taking advantage of the Enhanced Permeability and Retention Effect (EPR effect) in tumors and inflammatory tissue. Blood vessels formed in tumors are formed quickly and are abnormal because of poorly-aligned defective endothelial cells, a lack of smooth muscle layer and/or innervation with a wider lumen. This makes the tumor vessels permeable to particles of a size that would not normally exit the vasculature and allow the macromolecules to collect in tumor tissue. Furthermore, tumor tissues lack effective lymphatic drainage therefore once the macromolecules have entered the tumor tissue, they are retained there. Similar accumulation and retention is found in sites of inflammation.

The macromolecule of the invention may have a loading of pharmaceutically active agent of 2, 4, 8, 16, 32, 64 or 120 residues, especially 16, 32 or 64 residues per macromolecule.

Methods of making dendrimers are known in the art. For example, the dendrimers of the macromolecule may be made by a divergent method or a convergent method or a mixture thereof.

In the divergent method each generation of building units is sequentially added to the core or an earlier generation. The surface generation having one or both of the surface amino groups protected. If one of the amino groups is protected, the free amino group is reacted with one of the linker, the linker-pharmaceutically active agent or the pharmacokinetic modifying agent. If both amino groups are protected, they are protected with different protecting groups, one of which may be removed without removal of the other. One of the amino protecting groups is removed and reacted with one of the linker, the linker-pharmaceutically active agent or the pharmacokinetic modifying agent. Once the initial terminal group has been attached to the dendrimer, the other amino protecting group is removed and the other of the first and second terminal group is added. These groups are attached to the surface amino groups by amide formation as known in the art.

In the convergent method, each generation of building units is built up on the previous generation to form a dendron. The first and second terminal groups may be attached to the surface amino groups as described above before or after attachment of the dendron to the core.

In a mixed approach, each generation of building units is added to the core or a previous generation of building units. However, before the last generation is added to the dendrimer, the surface amino groups are functionalised with terminal groups, for example, a first and second terminal group, a first and third terminal group or a second and third terminal group. The functionalised final generation is then added to the subsurface layer of building units and the dendron is attached to the core.

The pharmaceutically active agent is reacted with one of the carboxylic acids of the linker by ester formation as known in the art. For example, an activated carboxylic acid is formed, such as an acid chloride or an anhydride is used and reacted with the hydroxy group of the pharmaceutically active agent. If the pharmaceutically active agent has more than one hydroxy group, further hydroxy groups may be protected.

In the case where a targeting agent is attached to the core, a functional group on the core may be protected during formation of the dendrimer then deprotected and reacted with the targeting agent, the spacer group or the targeting agent-spacer group. Alternatively, the core may be reacted with the spacer group or targeting agent-spacer group before the formation of the dendrimer.

Suitable protecting groups, methods for their introduction and removal are described in Greene & Wuts, Protecting Groups in Organic Synthesis, Third Edition, 1999.

Compositions Comprising the Macromolecule

While it is possible that the macromolecules of the invention may be administered as a neat chemical, in particular embodiments, the macromolecule is presented as a pharmaceutical composition.

The invention provides pharmaceutical formulations or compositions, both for veterinary and for human medical use, which comprise one or more macromolecules of the invention or a pharmaceutically acceptable salt thereof, with one or more pharmaceutically acceptable carriers, and optionally any other therapeutic ingredients, stabilisers, or the like. The carrier(s) must be pharmaceutically acceptable in the sense of being compatible with the other ingredients of the formulation and not unduly deleterious to the recipient thereof. The compositions of the invention may also include polymeric excipients/additives or carriers, e.g., polyvinylpyrrolidones, derivatised celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998), and in "Handbook of Pharmaceutical Excipients", Third Ed., Ed. A. H. Kibbe, Pharmaceutical Press, 2000.

The macromolecule may also be formulated in the presence of an appropriate albumin protein such as human serum albumin. Albumin carries nutrients around the body and may bind to the macromolecule and carry it to its site of action.

The macromolecules of the invention may be formulated in compositions including those suitable for oral, rectal, topical, nasal, inhalation to the lung, by aerosol, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the macromolecule into association with a carrier that constitutes one or more accessory ingredients. In general, the compositions are prepared by bringing the macromolecule into association with a liquid carrier to form a solution or a suspension, or alternatively, bring the macromolecule into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter. The composition may contain macromolecule of the invention that are nanoparticulate having a particulate diameter of below 1000 nm, for example, between 5 and 1000 nm, especially 5 and 500 nm, more especially 5 to 400 nm, such as 5 to 50 nm and especially between 5 and 20 nm. In particular embodiments, the composition contains macromolecules with a mean size of between 5 and 20 nm. In some embodiments, the macromolecule is polydispersed in the composition, with PDI of between 1.01 and 1.8, especially between 1.01 and 1.5, and more especially between 1.01 and 1.2. In particular embodiments, the macromolecule is monodispersed in the composition. Particularly preferred are sterile, lyophilized compositions that are reconstituted in an aqueous vehicle prior to injection.

Compositions of the present invention suitable for oral administration may be presented as discrete units such as capsules, cachets, tablets, lozenges, and the like, each containing a predetermined amount of the active agent as a powder or granules; or a suspension in an aqueous liquor or non-aqueous liquid such as a syrup, an elixir, an emulsion, a draught, and the like.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised with a suitable carrier may be made by molding in a suitable machine.

A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

Formulations suitable for parenteral administration conveniently comprise a sterile aqueous preparation of the macromolecule, which can be formulated to be isotonic with the blood of the recipient.

Nasal spray formulations comprise purified aqueous solutions of the active agent with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media such as mineral oil, petroleum, polyhydroxy alcohols or other bases used for topical formulations. The addition of other accessory ingredients as noted above may be desirable.

Pharmaceutical formulations are also provided which are suitable for administration as an aerosol, by inhalation. These formulations comprise a solution or suspension of the desired macromolecule or a salt thereof. The desired formulation may be placed in a small chamber and nebulized. Nebulization may be accomplished by compressed air or by ultrasonic energy to form a plurality of liquid droplets or solid particles comprising the macromolecules or salts thereof.

Often drugs are co-administered with other drugs in combination therapy, especially during chemotherapy. The macromolecules of the invention may therefore be administered as combination therapies. For example, when the pharmaceutically active agent is docetaxel, the macromolecule may be administered with doxorubicin, cyclophosphamide or capecitabine. Not only can the macromolecules be administered with other chemotherapy drugs but may also be administered in combination with other medications such as corticosteroids, anti-histamines, analgesics and drugs that aid in recovery or protect from hematotoxicity, for example, cytokines.

In some embodiments, particularly with oncology drugs, the composition is formulated for parenteral infusion as part of a chemotherapy regimen. In these embodiments, the compositions are substantially free or entirely free of solubilisation excipients, especially solubilisation excipients such as Cremophor and polysorbate 80. In particular embodiments, the pharmaceutically active agent is selected from docetaxel or paclitaxel and the formulation is substantially free or entirely free of solubilisation excipients such as Cremophor and polysorbate 80. By removing the solubilisation excipient the composition of dendrimer is less likely to cause side effects such as acute or delayed hypersensitivity including life-threatening anaphylaxis and/or severe fluid retention.

In some embodiments, the macromolecule is formulated for transdermal delivery such as an ointment, a lotion or in a transdermal patch or use of microneedle technology. High drug loading and aqueous solubility allows small volumes to carry sufficient drug for patch and microneedle technologies to provide a therapeutically effective amount. Such formulations are particularly suitable for delivery of testosterone.

The macromolecules of the invention may also be used to provide controlled-release of the pharmaceutically active agents and/or slow-release formulations.

In slow-release formulations, the formulation ingredients are selected to release the macromolecule from the formulation over a prolonged period of time, such as days, weeks or months. This type of formulation includes transdermal patches or in implantable devices that may be deposited subcutaneously or by injection intravenously, subcutaneously, intramuscularly, intraepidurally or intracranially.

In controlled-release formulations, the diacid linker is selected to release a majority of its pharmaceutically active agent in a given time window. For example, when the time taken for a majority of the macromolecule to accumulate in a target organ, tissue or tumor is known, the linker may be selected to release a majority of its pharmaceutically active agent after the time to accumulate has elapsed. This can allow a high drug load to be delivered at a given time point at the site where its action is required. Alternatively, the linker is selected to release the pharmaceutically active agent at a therapeutic level over a prolonged period of time.

In some embodiments, the formulation may have multiple controlled-release characteristics. For example, the formulation comprises macromolecules in which the drug is attached through different linkers allowing an initial burst of fast-released drug followed by slower release at low but constant therapeutic levels over a prolonged period of time.

In some embodiments, the formulation may have both slow-release and controlled-release characteristics. For example, the formulation ingredients may be selected to release the macromolecule over a prolonged period of time and the linker is selected to deliver a constant low therapeutic level of pharmaceutically active agent.

In some embodiments, the pharmaceutically active agent is attached to the same molecule through different linkers. In other embodiments, each drug-linker combination is attached to different macromolecules in the same formulation.

Methods of Use

The macromolecule of the invention may be used to treat or prevent any disease, disorder or symptom that the unmodified pharmaceutically active agent can be used to treat or prevent.

In some embodiments, where the pharmaceutically active agent is an oncology drug, the macromolecule is used in a method of treating or preventing cancer, or suppressing the growth of a tumor. In particular embodiments, the drug is selected from docetaxel, camptothecin, topotecan, irinotecan and gemcitabine, especially docetaxel.

In some embodiments, the cancer is a blood borne cancer such as leukaemia or lymphoma. In other embodiments, the cancer is a solid tumor. The solid tumor may be a primary or a metastatic tumor. Exemplary solid tumors include tumors of the breast, lung especially non-small cell lung cancer, colon, stomach, kidney, brain, head and neck especially squamous cell carcinoma of the head and neck, thyroid, ovary, testes, liver, melanoma, prostate especially androgen-independent (hormone refractory) prostate cancer, neuroblastoma and gastric adenocarcinoma including adenocarcinoma of the gastroesophageal junction.

Oncology drugs often have significant side effects that are due to off-target toxicity such as hematologic toxicity, neurological toxicity, cardiotoxicity, hepatotoxicity, nephrotoxicity, ototoxicity and encephalotoxicity. For example, taxanes such as docetaxel may cause the following adverse effects: infections, neutropenia, anemia, febrile neutropenia, hypersensitivity, thrombocytopenia, myelotoxicity, myelosuppression, neuropathy, dysgeusia, dyspnea, constipation, anorexia, nail disorders, fluid retention, asthenia, pain, nausea, diarrhea, vomiting, fatigue, non-specific neuro cognitive problems, vertigo, encephalopathy, mucositis, alopecia, skin reactions and myalgia.

Furthermore, solubilisation excipients required to formulate the oncology drugs may cause anaphylaxis, fluid retention and hypersensitivity. Premedication with corticosteroids, anti-histamines, cytokines and/or analgesics may also be required, each having their own side effects. The macromolecules of the present invention have high drug loading, controlled-release, may passively target a particular tissue and improve solubility allowing a reduction of side effects associated with the oncology drug, the formulation of the drug without solubilisation excipients and administration without or with reduced premedication.

In another aspect of the invention, there is provided a method of reducing the side effects of an oncology drug or the side-effects relating to the formulation of an oncology drug comprising administering an effective amount of the macromolecule of the present invention to a subject, wherein the oncology drug is the pharmaceutically active agent of the first terminal group.

In yet another aspect of the invention, there is provided a method of reducing hypersensitivity during chemotherapy comprising administering an effective amount of the macromolecule of the invention to a subject.

Therapeutic regimens for cancer treatment often involve a cyclic therapy where an oncology drug is administered once every two to four weeks. Often the drug is administered by infusion over 3 to 24 hours. In some cases to reduce the side effects of the drugs, or the risk of hypersensitivity, especially anaphylaxis from the formulation of the drug; premedication is required and its administration may be required up to 6 hours prior to treatment with the oncology drug. Such complex therapeutic regimens are time consuming and require the patient to remain in hospital from several hours to 2 days. The severe side effects may also limit the dose of oncology drug used and/or the number of cycles of therapy that can be administered and therefore in some cases efficacy of the therapy is diminished.

In the present invention, the macromolecule comprising the oncology drug reduces side effects associated with the drug as it passively accumulates at the tumor site or is directed to the tumor site by an appropriate targeting agent and release of the drug from the dendrimer is controlled.

The solubility of the macromolecules in aqueous solution allows them to be formulated without harmful solubilisation excipients thereby reducing side effects of the formulation and in some cases eliminating the need for premedication.

Furthermore, the macromolecules of the present invention need not be administered by prolonged infusion. In some embodiments, they may be administered by fast-infusion, for example, in less than 3 hours, including 2.5 hours, 2 hours, 1.5 hours, 1 hour or 30 minutes. In some embodiments, the macromolecule or formulation of macromolecule may be administered as a bolus, for example, in 5 seconds to 5 minutes.

The macromolecules of the present invention may also allow the dose of the pharmaceutically active agent to be increased compared to the pharmaceutically active agent being administered alone. In another aspect of the invention there is provided a method of increasing the dose of a pharmaceutically active agent comprising administering the macromolecule of the present invention wherein the first terminal group is the pharmaceutically active agent. In particular embodiments, the maximum tolerated dose is increased at least two fold compared to the pharmaceutically active agent when administered alone.

In particular embodiments of these aspects, the formulation of the macromolecule used in administration is substantially free of solubilisation excipients such as polyethoxylated caster oil (Cremophor EL) and polysorbate 80.

In some embodiments where the pharmaceutically active agent is testosterone or dihydrotestosterone and the macromolecule is used in a method of treating or preventing a disease or disorder associated with low testosterone levels.

Low testosterone levels may result from a number of conditions. For example, the organs that produce testosterone (testis, ovaries) do not produce enough testosterone (primary hypogonadism), the pituitary gland and its ability to regulate testosterone production is not working properly (secondary hypogonadism) or the hypothalamus may not be regulating hormone production correctly (tertiary hypogonadism).

Common causes of primary hypogonadism include undescended testicles, injury to the scrotum, cancer therapy, aging, mumps orchitis, chromosomal abnormalities, ovary conditions such as premature ovary failure or removal of both ovaries. Causes of secondary and tertiary hypogonadism include damage to the pituitary gland from tumors or treatment of nearby tumors, hypothalamus malformations such as in Kellman's syndrome, compromised blood flow to the pituitary gland or hypothalamus, inflammation caused by HIV/AIDS, inflammation from tuberculosis or sarcoides and the illegal use of anabolic steroids in body building.

It should also be noted that obesity can also be a cause of low testosterone levels as obesity significantly enhances the conversion of testosterone to oestrogen, a process that occurs predominantly in fat cells.

Symptoms of low testosterone include changes in mood (depression, fatigue, anger), decreased body hair, decreased mineral bone density (increased risk of osteoporosis), decreased lean body mass and muscle strength, decreased libido and erectile dysfunction, increased abdominal fat, rudimentary breast development in men and low or no sperm in semen.

An "effective amount" means an amount necessary at least partly to attain the desired response, or to delay the onset or inhibit progression or halt altogether, the onset or progression of a particular condition being treated. The amount varies depending upon the disease being treated, the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. In a particular embodiment the dosage is in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

In some embodiments the macromolecule is administered intravenously, intraarterially, intrapulmonarily, orally, by inhalation, intravesicularly, intramuscularly, intratracheally, subcutaneously, intraocularly, intrathecally or transdermally.

In some embodiments the macromolecule is administered as a bolus or by fast infusion, especially as a bolus.

In another aspect of the invention there is provided the use of a macromolecule of the invention in the manufacture of a medicament for treating or suppressing the growth of cancer, reducing the toxicity of an oncology drug or a formulation of an oncology drug, reducing side effects associated with an oncology drug or a formulation of an oncology drug or reducing hypersensitivity upon treatment with an oncology drug; wherein the pharmaceutically active agent of the first terminal group is an oncology drug.

In yet another aspect of the invention there is provided a use of a macromolecule of the invention in the manufacture of a medicament for treating or preventing a disease or disorder related to low testosterone levels; wherein the pharmaceutically active agent of the first terminal group is testosterone.

The invention will now be described with reference to the following Examples which illustrate some particular aspects of the present invention. However, it is to be understood that the particularity of the following description of the invention is not to supersede the generality of the preceding description of the invention.

Abbreviations

| | |
|---|---|
| Aba | Acetylbutyric acid |
| Ab | Antibody |
| Ac | Acetyl |
| ACN | Acetonitrile |
| Av | Streptavadin |
| BHAlysine | Benzhydrylamide lysine |
| Boc | benzyloxycarbonyl |
| Cp | Oxo-cyclopentane carboxylic acid |
| DBCO | Dibenzenecyclooctyne |
| DCC | Dicyclohexylcarbodiimide |
| DCM | Dichloromethane |
| DGA | Diglycolic acid |
| DIPEA | diisopropylethylamine |
| DMAP | dimethylaminopyridine |
| DMF | Dimethylformamide |
| EtOAc | Ethyl acetate |
| DTX | Docetaxel |
| EDC | 1-ethyl-3-(3-dimethylaminopropyl)carbodiimide |
| ESI | Electrospray ionisation |
| Gem | Gemcitabine |
| Glu | Glutaric acid |
| HPLC | High Performance Liquid Chromatography |
| HSBA | Hydrazinosulfonyl benzoic acid |
| LCMS | Liquid chromatography mass spectrometry |
| MeOH | Methanol |
| MIDA | Methyliminodiacetic acid |
| PBS | Phosphate buffered saline |
| o-PDA | Ortho-phenylenedioxydiacetic acid |
| PDT | 3,4-propylenedioxythiophene-2,5-dicarboxylic acid |
| PEG | Polyethylene glycol |
| PSSP | Dithiopropanoic acid |
| PTX | Paclitaxel |
| PyBop | Benzotriazol-1-yl-oxytripyrrolidino-phosphonium hexafluorophosphate |
| SB | Salbutamol |
| SEC | Size exclusion chromatography |
| SRB | Sulforhodamine B |
| TDA | 2,2'-thiodiacetic acid |
| TFA | Trifluoroacetic acid |

EXAMPLES

The dendrimers represented in the examples below include reference to the core and the building units in the outermost generation of the dendrimer. The 1$^{st}$ to subsurface generations are not depicted. The dendrimer BHALys[Lys]$_{32}$ is representative of a 5 generation dendrimer having the formula BHALys[Lys]$_{32}$[Lys]$_4$[Lys]s[Lys]$_{16}$[Lys]$_{32}$, the 64 surface amino groups being available to bind to terminal groups.

Preparation of the dendrimer scaffolds BHALys[Lys]$_{32}$ [α-NH$_2$.TFA]$_{32}$[ε-PEG$_{570}$]$_{32}$, BHALys[Lys]$_{32}$[α-NH$_2$.TFA]$_{32}$[(ε-PEG$_{1100}$]$_{32}$, BHALys[Lys]$_{32}$[α-NH$_2$.TFA]$_{32}$[ε-t-PEG$_{2300}$]$_{32}$ BHALys[Lys]$_{32}$[α-4-HSBA]$_{32}$[ε-PEG$_{1100}$]$_{32}$, BHALys[Lys]$_{32}$[α-GILGVP-NH$_2$.TFA]$_{32}$[ε-PEG$_{1100}$]$_{32}$, and BHALys[Lys]$_{32}$[α-GILGVP-NH$_2$.TFA]$_{32}$[ε-t-PEG$_{2300}$]$_{32}$ can be found in Kaminskas et al., J Control. Release (2011) doi 10.1016/j.jconrel.2011.02.005. Preparation of the dendrimer scaffolds 4-azidobenzamide-PEG$_{12}$NEOEOEN[Su(NPN)$_2$][Lys]$_{16}$ [NH$_2$.TFA]$_{32}$ can be found WO08/017122.

General Procedures

General Procedure A. Installation of Linkers to Drugs A

To a magnetically stirred solution of carboxylic acid linker (0.2-0.5 mmol) in solvent DMF or acetonitrile (1-5 mL) at 0° C. was added coupling agent either EDC or DCC (1.2 equivalents). The mixture was left to stir for 5 min., then a solution of solvent (1 mL) containing a mixture of drug (0.4-1 equivalents) and DMAP (0.4-1 equivalents) was added dropwise. The mixture was kept at 0° C. for 1 hour then allowed to warm to ambient temperature. The volatiles were then removed in vacuo and the residue purified by preparative HPLC (BEH 300 Waters XBridge C18, 5 µM, 30×150 mm, 40-80% ACN/water (5-40 min), no buffer) to yield the desired product.

General Procedure B. Installation of Linkers to Drugs B.

To a magnetically stirred solution of drug (0.3-1.0 mmol) and anhydride (2 equivalents) in DMF (3-5 mL) was added DIPEA (3 equivalents). The mixture was stirred at ambient temperature overnight. The volatiles were then removed in vacuo and the residue purified by preparative HPLC (BEH 300 Waters XBridge C18, 5 µM, 30×150 mm, 40-70% ACN/water (5-40 min), no buffer, RT=34 min). The appropriate fractions were concentrated in vacuo providing the desired target.

General Procedure C. Loading Dendrimer with Drug-Linker.

To a magnetically stirred mixture of BHALys[Lys]$_{32}$[α-NH$_2$.TFA]$_{32}$[ε-PEG$_{1100}$]$_{32}$ (0.5-1.0 µmol) and DIPEA (1.2 equivalents per amine) in DMF at room temperature was added linker—drug (1.2 equivalents per amine group) and PyBOP (1.2 equivalents per amine group). After 1.5 hours at room temperature the volatiles were removed and the residue purified by SEC (sephadex, LH20, MeOH). The appropriate fractions, as judged by HPLC, were combined and concentrated to provide the desired material.

General Procedure D. Click Reaction

To a magnetically stirred solution dendrimer (0.5-1.0 mmol) in 1:1 H$_2$O/t-BuOH (approximately 0.5 mL) was added alkyne reagent (2 equivalents), sodium ascorbate solution (2 equivalents) and CuSO$_4$ solution (20 mol %). The solution was heated at 80° C. and monitored by HPLC. Additional charges of both sodium ascorbate and CuSO$_4$ were added as required to drive the reaction to completion.

After the reaction was judged complete the reaction was concentrated in vacuo and then purified.

Example 1

(a) Preparation of 4-Aba-DTX:

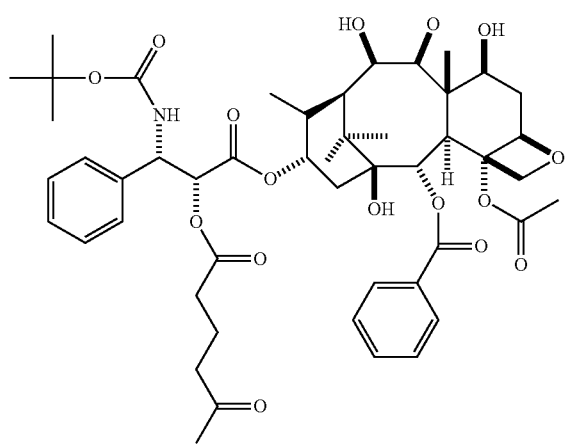

Prepared using Procedure A above, using DTX (200 mg, 0.25 mmol) and 4-acetylbutyric acid (42 mg, 0.32 mmol) as the linker. Preparative HPLC (RT=32 mins) provided 73 mg (32%) of product as a white solid. LCMS (C8, gradient: 40-90% ACN/H$_2$O (1-7 min), 90% ACN (7-9 min), 90-40% ACN (9-11 min), 40% ACN (11-15 min), 0.1% TFA) Rt (min)=7.60. ESI (+ve) observed [M+H]$^+$=920. Calculated for C$_{49}$H$_{61}$NO$_{16}$=919.40 Da. $^1$H NMR (300 MHz, CD$_3$OD) δ (ppm): 1.09 (s, 3H), 1.13 (s, 3H), 1.38 (s, 9H), 1.66 (s, 3H), 1.74-1.97 (m, 7H), 2.10 (s, 3H), 2.12-2.36 (m, 1H), 2.29-2.58 (m, 8H), 3.83 (d, J=6.9 Hz, 1H), 4.14-4.26 (m, 3H), 4.95-5.05 (m, 2H), 5.18-5.35 (m, 3H), 5.61 (d, J=7.2 Hz, 1H), 6.05 (m, 1H), 7.17-720 (m, 1H), 7.23-7.45 (m, 4H), 7.52-7.62 (m, 2H), 7.63-7.72 (m, 1H), 8.10 (d, J=7.2 Hz, 2H).

(b) Preparation of BHALys[Lys]$_{32}$[α-4-HSBA-4Aba-DTX]$_{32}$[ε-PEG$_{1100}$]$_{32}$

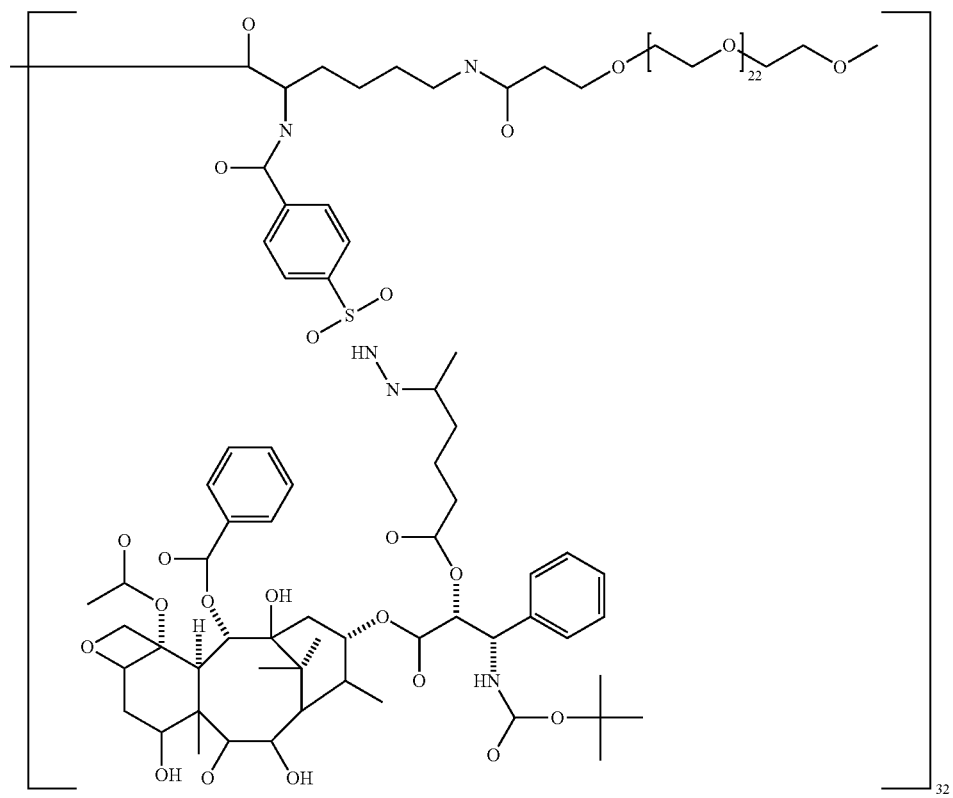

Prepared using Procedure C above. To a magnetically stirred solution of 4-Aba-DTX (15 mg, 16.3 μmol) in dry MeOH (1 mL) was added TFA (50 μL) and BHALys[Lys]$_{32}$[α-4-HSBA]$_{32}$[ε-PEG$_{1100}$]$_{32}$ (20 mg, 0.43 μmol). The mixture was left to stir overnight at ambient temperature then added directly to a sephadex column (LH20, MeOH) for purification. The appropriate fractions, as judged by HPLC, were combined and concentrated to provide 25 mg (78%) of desired material as a white solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rt (min)=6.77. $^1$H NMR (300 MHz, CD$_3$OD) δ (ppm): 0.6-2.2 (m, 812H), 2.2-2.5 (m, 115H), 2.9-3.2 (m, 78H), 3.26 (s, 79H), 3.3-3.8 (m, 2824H), 5.1-5.3 (m, 31H), 5.5-5.6 (m, 10H), 5.9-6.1 (m, 9H), 6.9-8.2 (m, 329H). Theoretical molecular weight of conjugate: 78.6 kDa. $^1$H NMR indicates 9 DTX/dendrimer. Actual molecular weight is approximately 56.4 kDa (13% DTX by weight).

Example 2

(a) Preparation of PSSP-DTX:

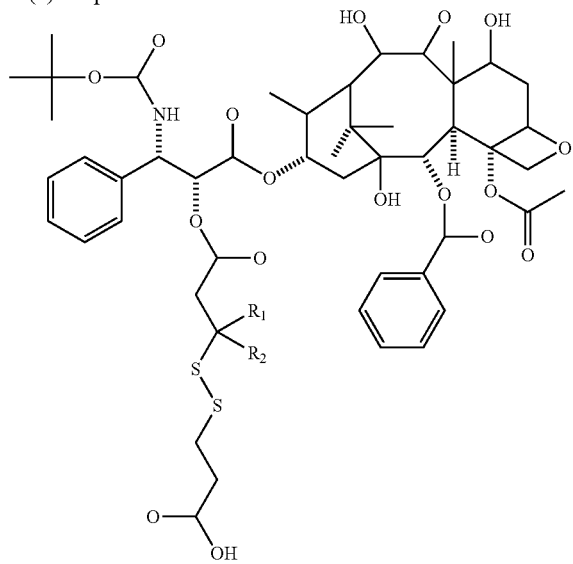

In this example ($R_1$=$R_2$=H) it could be envisioned that the rate of release of docetaxel could be increased or decreased by increasing or decreasing the degree of steric hindrance about the disulphide bond (Worrell N; R., Cumber A. J., Parnell G. D., Mirza A., Forrester J. A., Ross W. C. J.: *Effect of linkage variation on pharmacokinetics of ricin-A-chain antibody conjugates in normal rats*. Anti-Cancer Drug Design 1, 179, 1986). This could be achieved through the addition of substituents, amongst others α and or β to the disulphide bond. This type of tuning strategy is often used in prodrug design strategies and takes advantage of the well known Thorpe-Ingold or gem-dimethyl effect (*The gem-Dimethyl Effect Revisited* Steven M. Bachrach, J. Org. Chem. 2008, 73, 2466-2468).

Prepared using Procedure A above, using DTX (500 mg, 0.62 mmol) and 3,3'-dithiopropanoic acid (130 mg, 0.62 mmol) as the linker. Preparative HPLC (RT=32 min) provided 179 mg (29%) of product as a white solid. LCMS (C8, gradient: 40-90% ACN/H$_2$O (1-7 min), 90% ACN (7-9 min), 90-40% ACN (9-11 min), 40% ACN (11-15 min), 0.1% TFA) Rf (min)=7.57. ESI (+ve) observed [M+H]$^+$=1000. Calculated for C$_{49}$H$_{61}$NO$_{17}$S$_2$=999.34 Da. $^1$H NMR (300 MHz, CD$_3$OD) δ (ppm): 1.13 (s, 3H), 1.17 (s, 3H), 1.43 (s, 9H), 1.70 (s, 3H), 1.72-1.99 (m, 6H), 2.13-2.32 (m, 1H), 2.37-2.55 (m, 4H), 2.66-2.76 (m, 2H), 2.76-3.02 (m, 6H), 3.87 (d, J=6.9 Hz, 1H), 4.18-4.31 (m, 3H), 5.00-5.06 (m, 3H), 5.24-5.42 (m, 3H), 5.64 (d, J=72 Hz, 1H), 6.10 (m, 1H), 7.23-7.33 (m, 1H), 7.36-7.48 (m, 4H), 7.53-7.65 (m, 2H), 7.66-7.76 (m, 1H), 8.13 (d, J=7.2 Hz, 2H).

(b) Preparation of BHALys[Lys]$_{32}$[α-PSSP-DTX]$_{32}$[ε-PEG$_{1100}$]$_{32}$

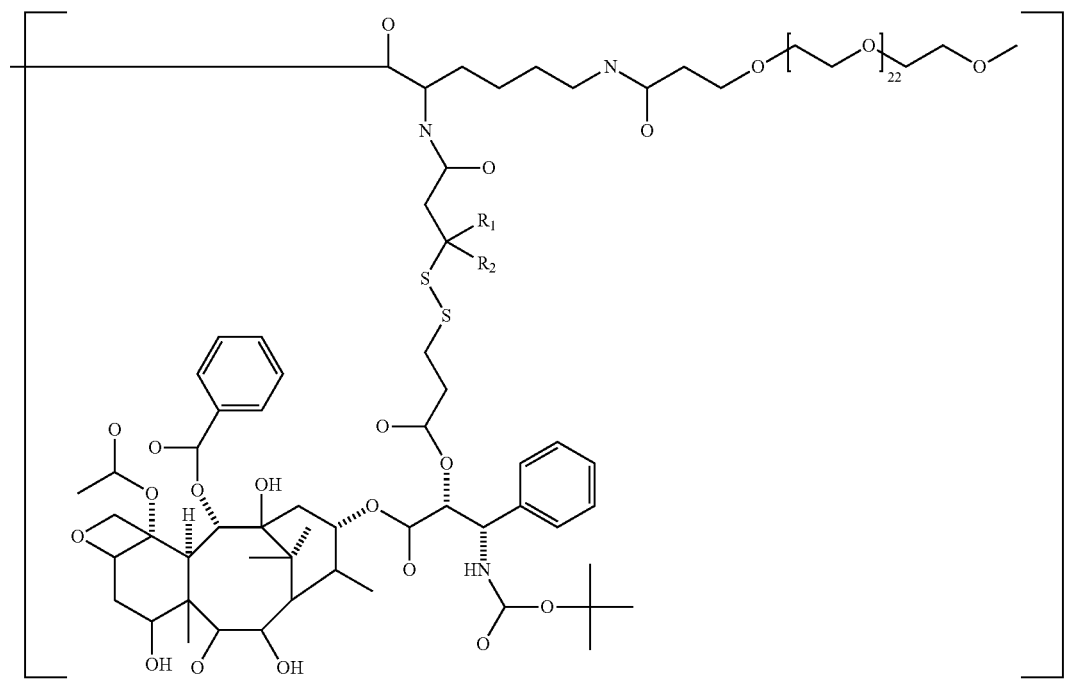

$R_1$ = $R_2$ = H

Prepared using Procedure C above, using BHALys[Lys]$_{32}$[α-NH$_2$.TFA]$_{32}$[ε-PEG$_{1100}$]$_{32}$ (34 mg, 0.78 μmol) and PSSP-DTX (30 mg, 30 μmol). Purification by SEC provided 50 mg (89%) of desired material as a white solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rf (min)=7.96 min. $^1$H NMR (300 MHz, CD$_3$OD) δ (ppm): 0.7-2.0 (m, 1041H), 2.0-2.2 (m, 151H), 2.2-2.5 (m, 119H), 2.5-2.7 (m, 31H), 2.7-3.0 (m, 119H), 3.0-3.2 (m, 68H), 3.26 (s, 132H), 3.3-3.8 (m, 2806H), 3.9-4.3 (m, 76H), 5.1-5.3 (m, 55H), 5.5-5.6 (m, 17H), 5.9-6.1 (m, 17H), 7.1-8.1 (m, 243H). Theoretical molecular weight of conjugate: 74.9 kDa. $^1$H NMR indicates 17 DTX/dendrimer. Actual molecular weight is approximately 56.1 kDa (24% DTX by weight).

Example 3
(a) Preparation of DGA-DTX:

Prepared using Procedure B above, using DTX (300 mg, 371 μmol) and diglycolic anhydride (86 mg, 742 μmol) as the linker. Preparative HPLC (RT=34 min) provided 85 mg (25%) of DGA-DTX as a white solid. LCMS (C8, gradient: 40-90% ACN/H$_2$O (1-7 min), 90% ACN (7-9 min), 90-40% ACN (9-11 min), 40% ACN (11-15 min), 0.1% Formic acid) Rt (min)=5.90. ESI (+ve) observed [M+H]$^+$=924.10. Calculated for C$_{47}$H$_{57}$NO$_{18}$=923.36 Da. $^1$H NMR (300 MHz, CDCl$_3$) δ (ppm): 1.11 (s, 3H), 1.21 (s, 3H), 1.33 (s, 9H), 1.58-2.66 (m, 7H), 1.73 (s, 3H), 1.93 (s, 3H), 2.67-3.67 (br s, 5H), 3.73-3.97 (br s, 1H), 4.02-4.68 (m, 7H), 4.96 (d, J=8.4 Hz, 1H), 5.24 (s, 1H), 5.35-5.55 (m, 1H), 5.50 (s, 1H), 5.66 (d, J=6.7 Hz, 1H), 5.95-6.30 (m, 1H), 7.24-7.68 (m, 7H), 8.08 (d, J=6.9 Hz, 2H).

(b) Preparation of BHALys[Lys]$_{32}$[α-DGA-DTX]$_{32}$[ε-PEG$_{1100}$]$_{32}$

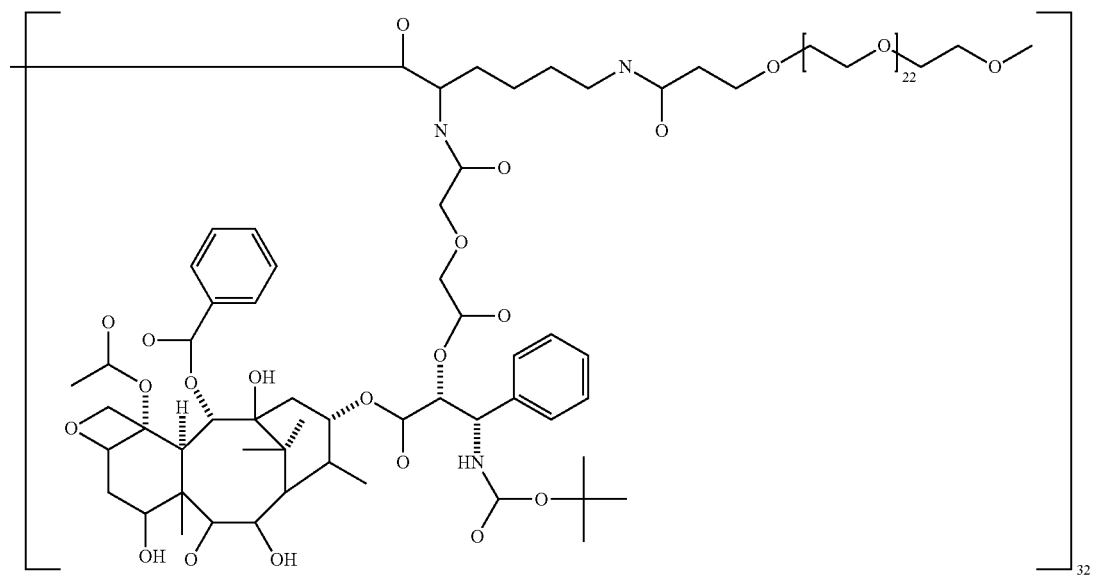

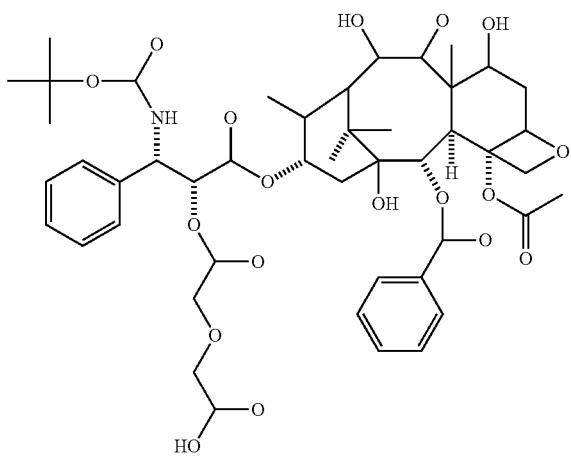

Prepared using Procedure C above, using BHALys[Lys]$_{32}$[α-NH$_2$.TFA]$_{32}$[ε-PEG$_{1100}$]$_{32}$ (36 mg, 0.84 μmol) and DOA-DTX (30 mg, 33 μmol). Purification by SEC provided 45 mg (79%) of desired material as a white solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rt (min)=7.69. $^1$H NMR (300 MHz, CD$_3$OD) δ (ppm): 1.0-2.1 (m, 833H), 2.3-2.6 (m, 125H), 3.0-3.3 (m, 68H), 3.5-4.0 (m, 2803H), 4.0-4.7 (m, 214H), 5.0-5.1 (m, 23H), 5.3-5.5 (m, 54H), 5.6-5.8 (m, 19H), 6.0-6.3 (m, 18H), 7.2-7.8 (m, 203H), 8.1-8.2 (m, 46H). Theoretical molecular weight of conjugate: 72.4 kDa. $^1$H NMR indicates 18 DTX/dendrimer. Actual molecular weight is approximately 55.7 kDa (26% DTX by weight).

Example 4

(a) Preparation of Cp-DTX:

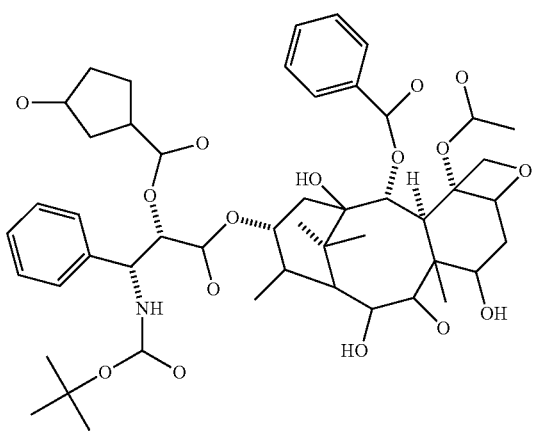

Prepared using Procedure A above, using DTX (500 mg, 619 μmol) and 3-oxo-1-cyclopentanecarboxylic acid (79 mg, 619 μmol) as the linker. Preparative HPLC (RT=33.5 min) provided Cp-DTX (401 mg, 71%) as a white solid. LCMS (C8, gradient: 40-90% ACN/H$_2$O (1-7 min), 90% ACN (7-9 min), 90-40% ACN (9-11 min), 40% ACN (11-15 min), 0.1% Formic acid) Rt(min)=6.61. ESI (+ve) observed [M+H]$^+$=918.54. Calculated for C$_{49}$H$_{59}$NO$_{16}$=917.38 Da. $^1$H NMR (300 MHz, CDCl$_3$) δ (ppm): 1.13 (s, 3H), 1.24 (s, 3H), 1.33 (s, 9H), 1.76 (s, 3H), 1.77-2.01 (m, 3H), 1.95 (s, 3H), 2.11-2.49 (m, 6H), 2.46 (s, 3H), 2.60 (ddd, J=16.2, 9.9 and 6.9 Hz, 1H), 3.10-3.24 (m, 1H), 3.94 (d, J=7.2 Hz, 1H), 4.20 (d, J=8.4 Hz, 1H), 4.27 (dd, J=11.1 and 6.6 Hz, 1H), 4.33 (d, J=8.4 Hz, 1H), 4.97 (d, J=7.8 Hz, 1H), 5.21 (s, 1H), 5.33 (d, J=9.9 Hz, 1H), 5.42 (d, J=2.7 Hz, 1H), 5.48-5.58 (br d, J=9 Hz, 1H), 5.69 (d, J=7.2 Hz, 1H), 6.27 (t, J=8.7 Hz, 1H), 7.25-7.45 (m, 5H), 7.47-7.53 (m, 2H), 7.57-7.64 (m, 1H), 8.09-8.14 (m, 2H).

(b) Preparation of 4-HSBA-Cp-DTX:

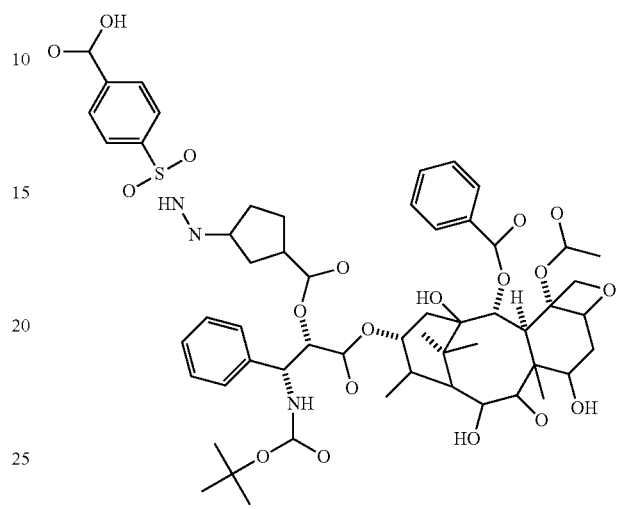

A solution of DTX-Cp (30 mg, 32.7 μmol) in TFA/MeOH (5% v/v, 1 mL) was added to 4-hydrazinosulfonylbenzoic acid (6 mg, 27.8 μmol). The mixture was left to react at 38° C. for 1.5 h after which the solvent was evaporated in vacuo. The white semi-solid obtained was used directly in the next step.

(c) Preparation of BHALys[Lys]$_{32}$[α-4-HSBA-Cp-DTX]$_{32}$[ε-PEG$_{1100}$]$_{32}$

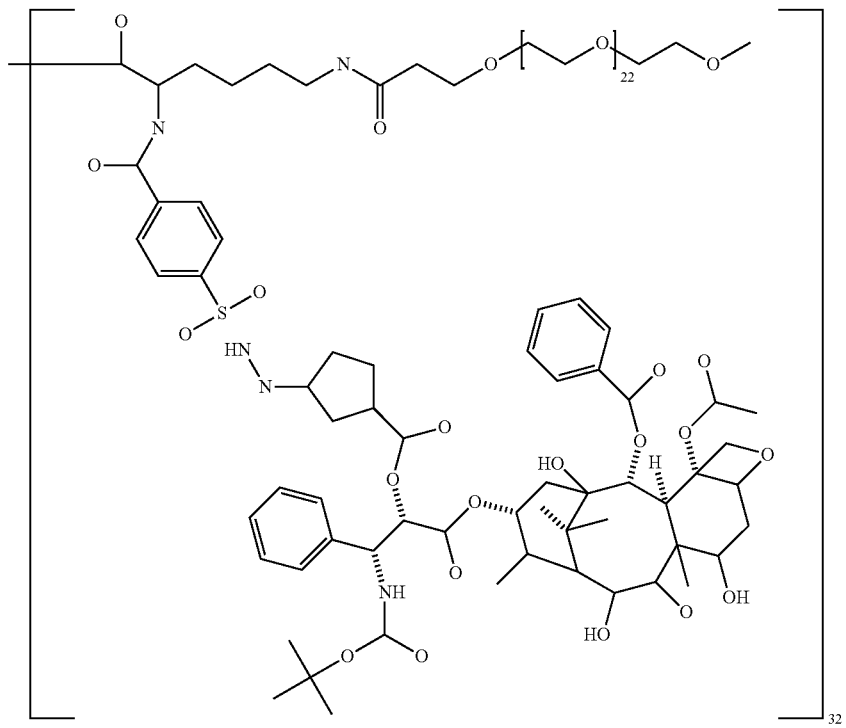

Method A:

To a magnetically stirred solution of Cp-DTX (7.5 mg, 8.15 μmol) in dry MeOH (1 mL) was added TFA (50 μL). This solution was added to BHALys[Lys]$_{32}$ [α-4-HSBA]$_{32}$ [ε-PEG$_{1100}$]$_{32}$ (10 mg, 0.215 μmol). The mixture was left to react overnight at ambient temperature then added directly to a sephadex column (LH20, MeOH) for purification. The appropriate fractions, as judged by HPLC, were combined, concentrated and freeze-dried from water to provide 18 mg (70%) of desired material as a white solid.

Method B:

To 4-HSBA-Cp-DTX (31 mg, 27.8 μmol) and PyBOP (14.5 mg, 27.8 μmol) was added a solution of BHALys[Lys]$_{32}$[α-NH$_2$.TFA]$_{32}$[ε-PEG$_{1100}$]$_{32}$ (31.5 mg, 0.7 μmol) and DIPEA (15 μL, 89.0 μmol) in DMF (1 mL). The resulting mixture was stirred overnight at ambient temperature after which the solvent was evaporated in vacuo. The remaining yellow oil was added to a sephadex column (LH20, MeOH) for purification. The appropriate fractions, as judged by HPLC, were combined, concentrated and freeze-dried from water to provide 34 mg (81% over two steps) of desired material as a white solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rt (min)=7.65. $^1$H NMR (300 MHz, CD$_3$OD) δ (ppm): 1.12 (s, 44H), 1.16 (s, 44H), 1.21-2.29 (m, 688H), 2.32-2.53 (m, 113H), 2.80-3.25 (m, 64H), 3.35 (s, 85H), 3.36-3.90 (m, 2815H), 4.17-4.28 (m, 77H), 4.45-4.65 (m, 50H), 4.97-5.04 (m, 23H), 5.22-5.44 (m, 40H), 5.63 (d, J=6.9 Hz, 16H), 6.00-6.20 (m, 15H), 7.2-8.25 (m, 308H). Theoretical molecular weight of conjugate: 78.8 kDa. $^1$H NMR indicates 15 DTX/dendrimer in each case. Actual molecular weight is approximately 60.0 kDa (20% DTX by weight).

Example 5

(a) Preparation of Glu-DTX:

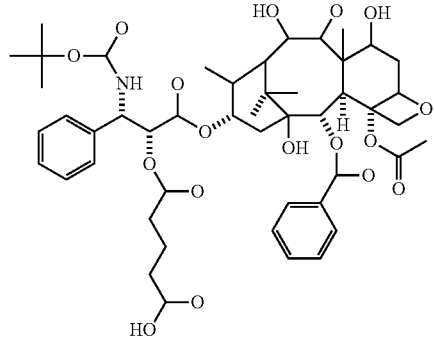

Prepared using Procedure B above, using DTX (300 mg, 371 μmol) and glutaric anhydride (85 mg, 742 μmol) in DMF (3.7 mL) as the linker. Preparative HPLC (Rt=33 min) provided 106 mg (31%) of Glu-DTX as a white solid. LCMS (C8, gradient: 40-90% ACN/H$_2$O (1-7 min), 90% ACN (7-9 min), 90-40% ACN (9-11 min), 40% ACN (11-15 min), 0.1% Formic acid) Rt (min)=6.12. ESI (+ve) observed [M+H]$^+$=922.13. Calculated for C$_{48}$H$_{59}$NO$_{17}$=921.38 Da. $^1$H NMR (300 MHz, CDCl$_3$) δ (ppm): 1.11 (s, 3H), 1.22 (s, 3H), 1.33 (s, 9H), 1.74 (s, 3H), 1.79-2.65 (m, 14H), 1.93 (s, 3H), 3.91 (d, J=6.5 Hz, 1H), 4.19 (d, J=8.4 Hz, 1H), 4.26 (dd, J=11.1 and 6.9 Hz, 1H), 4.31 (d, J=8.4 Hz, 1H), 4.96 (d, J=8.2 Hz, 1H), 5.23 (s, 1H), 5.38 (br s, 1H), 5.35-5.65 (br d, 1H), 5.67 (d, J=6.5 Hz, 1H), 6.10-6.30 (s, 1H), 7.26-7.34 (m, 3H), 7.34-7.43 (m, 2H), 7.46-7.55 (m, 2H), 7.57-7.65 (m, 1H), 8.10 (d, J=7.4 Hz, 2H).

(b) Preparation of BHALys[Lys]$_{32}$[α-Glu-DTX]$_{32}$[ε-PEG$_{1100}$]$_{32}$

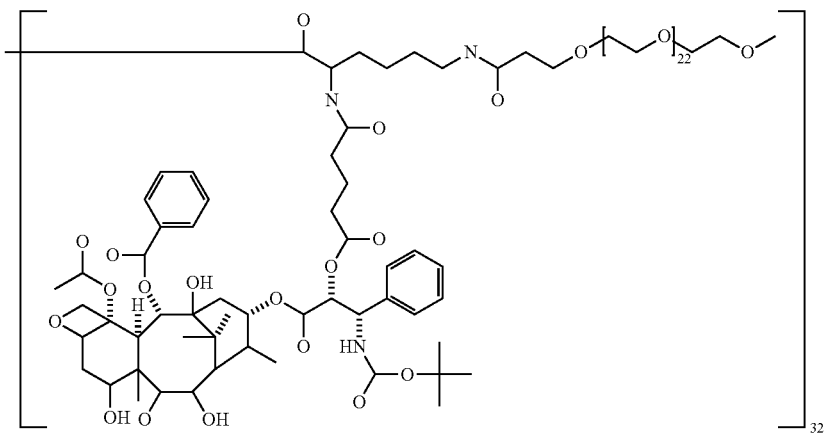

Prepared using Procedure C above, using BHALys[Lys]$_{32}$[α-NH$_2$.TFA]$_{32}$[ε-PEG$_{1100}$]$_{32}$ (50 mg, 1.1 μmol) and Glu-DTX (39 mg, 42.3 μmol). Purification by sephadex column (LH20, MeOH) provided 49.5 mg (78%) of desired material as a white solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rt (min)=7.78. $^1$H NMR (300 MHz, CD$_3$OD) δ (ppm): 1.00-2.10 (m, 1037H), 2.10-2.74 (m, 296H), 3.05-3.27 (br s, 88H), 3.35 (s, 96H), 3.36-3.78 (m, 2800H), 3.80-3.93 (m, 42H), 4.01-4.47 (m, 125H), 4.47-4.60 (br a, 23H), 4.92-5.08 (br s, 30H), 5.18-5.45 (m, 70H), 5.54-5.74 (br s, 22H), 6.00-6.23 (br s, 20H), 7.15-7.75 (m, 414H), 8.05-8.20 (br d, J=6.4 Hz, 49H). Theoretical molecular weight of conjugate: 72.6 kDa. $^1$H NMR indicates 20 DTX/dendrimer. Actual molecular weight is approximately 57.5 kDa (28% DTX by weight).

Example 6

(a) Preparation of MIDA-DTX:

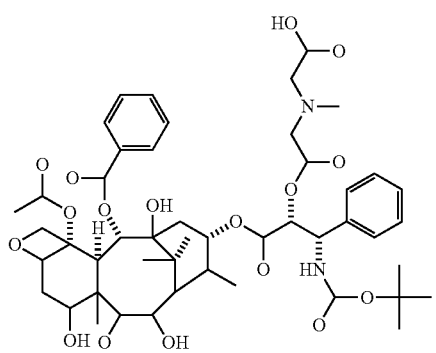

Prepared using Procedure A above, using DTX (100 mg, 124 µmol) and methyliminodiacetic acid (91 mg, 620 µmol) as the linker. Preparative HPLC (RT=22.5 min) provided 29 mg (25%) of product as a white solid. LCMS (C8, gradient: 40-90% ACN/H$_2$O (1-7 min), 90% ACN (7-9 min), 90-40% ACN (9-11 min), 40% ACN (11-15 min), 0.1% Formic acid) Rt (min)=4.62. ESI (+ve) observed [M+H]$^+$=937.34. Calculated for $C_{48}H_{60}N_2O_{17}$=936.39 Da. $^1$H NMR (300 MHz, CD$_3$OD) δ (ppm): 1.13 (s, 3H), 1.17 (s, 3H), 1.40 (s, 9H), 1.70 (s, 3H), 1.84 (ddd, J=14.1, 11.4 and 1.8 Hz, 1H), 1.93 (s, 3H), 2.04 (dd, J=15.0 and 8.7 Hz, 1H), 2.30 (dd, J=15.0 and 8.7 Hz, 1H), 2.43 (s, 3H), 2.46 (ddd, J=14.1, 9.5 and 6.6 Hz, 1H), 2.61 (s, 3H), 3.49 (s, 2H), 3.81-3.94 (m, 3H), 4.21 (s, 2H), 4.24 (dd, J=11.4 and 6.6 Hz, 1H), 5.01 (dd, J=9.5 and 1.8 Hz, 1H), 5.29 (s, 1H), 5.43 (s, 2H), 5.65 (d, J=7.2 Hz, 1H), 6.16 (t, J=8.7 Hz, 1H), 7.21-7.34 (m, 1H), 7.35-7.50 (m, 4H), 7.51-7.79 (m, 3H), 8.13 (d, J=7.2 Hz, 2H).

(b) Preparation of BHALys[Lys]$_{32}$[α-MIDA-DTX]$_{32}$[ε-PEG$_{1100}$]$_{32}$

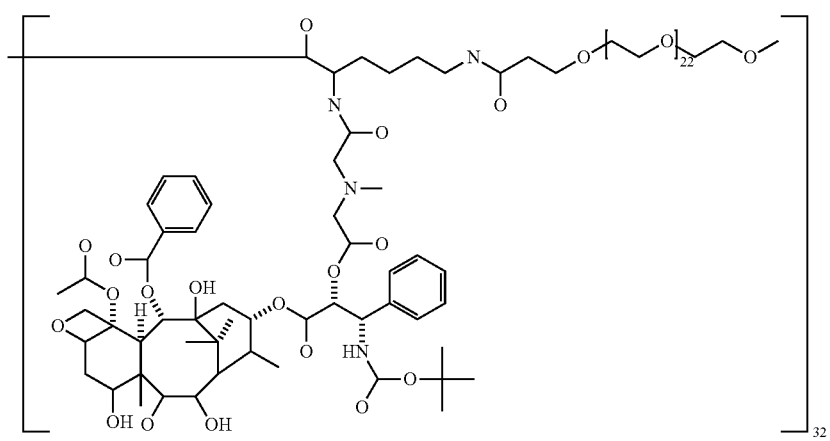

Prepared using Procedure C above, using BHALys[Lys][α-NH$_2$.TFA]$_{32}$[ε-PEG$_{1100}$]$_{32}$ (31.5 mg, 0.7 µmol) and MIDA-DTX (26 mg, 27.8 µmol). Purification by SEC provided 41.6 mg (93%) of the desired product as a white solid. HPLC (C8, gradient: 40-80% ACN/H$_2$O (1-7 min), 80% ACN (7-9 min), 80-40% ACN (9-11 min), 40%6 ACN (11-15 min), 10 mM ammonium formate) Rt (min)=7.78. $^1$H NMR (300 MHz, CD$_3$OD) δ (ppm): 1.00-2.10 (m, 1186H), 2.12-2.68 (m, 283H), 3.06-3.27 (m, 77H), 3.35 (s, 101H), 3.36-3.96 (m, 2842H), 4.07-4.61 (m, 143H), 4.93-5.10 (br s, 31H), 5.19-5.48 (m, 77H), 5.55-5.75 (m, 27H), 5.97-6.29 (m, 27H), 7.10-7.84 (m, 258H), 8.03-8.23 (m, 60H). Theoretical molecular weight of conjugate: 73.1 kDa. $^1$H NMR indicates 27 DTX/dendrimer. Actual molecular weight is approximately 64.2 kDa (34% DTX by weight).

Example 7

(a) Preparation of o-PDA-DTX

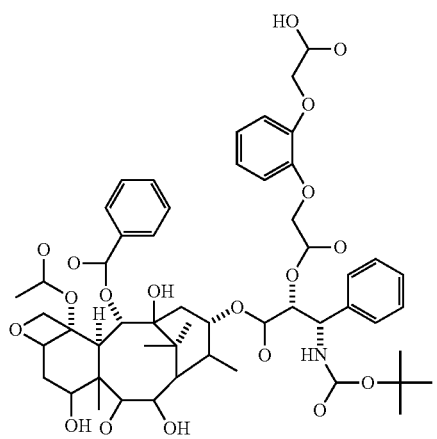

Prepared using Procedure A above, using DTX (300 mg, 0.37 mmol) and o-phenylenedioxydiacetic acid (419 mg, 1.85 mmol) as the linker. Preparative HPLC (RT=26 min) provided 21 mg (11%) of product as a white solid. LCMS (C8, gradient: 40-90%, ACN/H$_2$O (1-7 min), 90% ACN (7-9 min), 90-40% ACN (9-11 min), 40% ACN (11-15 min), 0.1% Formic acid) Rt (min) 7.27. ESI (+ve) observed [M+H]$^+$=1016.29. Calculated for $C_{53}H_{61}NO_{19}$=1015.38 Da. $^1$H NMR (300 MHz, CD$_3$OD) δ (ppm): 1.13 (s, 3H), 1.17 (s, 3H), 1.40 (s, 9H), 1.69 (s, 3H), 1.82 (ddd, J=13.5, 11.4 and 2.1 Hz, 1H), 1.89 (s, 3H), 1.94-2.07 (m, 1H), 2.00-2.33 (m, 1H), 2.40 (s, 3H), 2.45 (ddd, J=15.9, 9.6 and 6.6 Hz, 1H), 3.87 (d, J=6.9 Hz, 1H), 4.18-4.27 (m, 3H), 4.68 (s, 2H), 4.87 (d, J=6.0 Hz, 1H), 5.00 (d, J=9.3 Hz, 1H), 5.27 (s, 1H), 5.36-5.43 (m, 2H), 5.64 (d, J=6.9 Hz, 1H), 6.13 (t, J=9.0 Hz, 1H), 6.86-6.98 (m, 4H), 7.23-7.32 (m, 1H), 7.35-7.43 (m, 4H), 7.52-7.60 (m, 2H), 7.62-7.70 (m, 1H), 8.07-8.15 (m, 2H).

(b) Preparation of BHALys[Lys]$_{32}$[α-o-PDA-DTX]$_{32}$[ε-PEG$_{1100}$]$_{32}$

Example 8
(a) Preparation of TDA-DTX Via Procedure A:

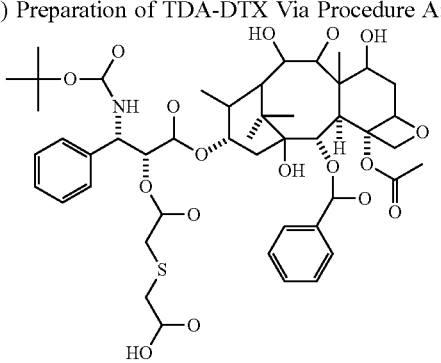

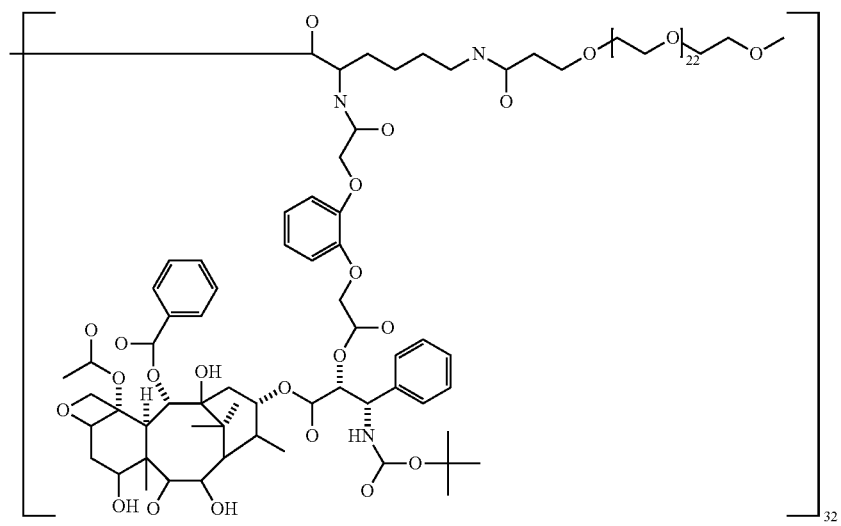

Prepared using Procedure C above, using BHALys[Lys]$_{32}$[α-NH$_2$.TFA]$_{32}$[ε-PEG$_{1100}$]$_{32}$ (22.5 mg, 0.5 μmol) and o-PDA-DTX (21 mg, 20.7 μmol). Purification by SEC (sephadex, LH20, MeOH) provided 30 mg (95%) of the desired product as a slightly beige semi-solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rt (min)=9.80. $^1$H NMR (300 MHz, CD$_3$OD) δ (ppm): 0.95-2.12 (m, 1058H), 2.12-2.66 (m, 205H), 2.89-3.29 (m, 125H), 3.35 (s, 85H), 3.36-3.93 (m, 2822H), 3.98-4.75 (m, 212H), 4.83-5.08 (m, 89H), 5.18-5.34 (m, 17H), 5.34-5.54 (m, 38H), 5.54-5.79 (m, 22H), 6.01-6.26 (m, 22H), 6.68-7.13 (m, 98H), 7.13-7.78 (m, 214H), 8.02-8.22 (m, 50H). Theoretical molecular weight of conjugate: 75.6 kDa. $^1$H NMR indicates 22 DTX/dendrimer. Actual molecular weight is approximately 63.2 kDa (28%4 DTX by weight).

Prepared using Procedure A above, using DTX (500 mg, 0.62 mmol) and 2,2'-thiodiacetic acid (370 mg, 2.5 mmol) as the linker. Preparative HPLC (RT=33 min) provided 240 mg (41%) of product as a white solid. LCMS (C8, gradient: 40-90% ACN/H$_2$O (1-7 min), 90% ACN (7-9 min), 90-40% ACN (9-11 min), 40% ACN (11-15 min), 0.1% TFA) Rt (min)=10.60. ESI (+ve) observed [M+H]$^+$=940. Calculated for C$_{47}$H$_{57}$NO$_{17}$S=939.33 Da. $^1$H NMR (300 MHz, CD$_3$OD) δ (ppm): 1.15 (s, 3H), 1.19 (s, 31H), 1.43 (s, 9H), 1.72 (s, 3H), 1.78-2.05 (m, 2H), 1.93 (s, 3H), 2.16-2.57 (m, 2H), 2.43 (s, 3H), 336-3.63 (m, 2H), 3.89 (d, J=6.9 Hz, 1H), 4.18-4.34 (m, 3H), 5.03 (d, J=9.0 Hz, 2H), 5.28-5.44 (m, 3H), 5.66 (d, J=7.2 Hz, 1H), 6.11 (m, 1H), 7.24-7.35 (m, 1H), 7.38-7.50 (m, 4H), 7.52-7.65 (m, 2H), 7.66-7.76 (m, 1H), 8.14 (d, J=7.2 Hz, 2H).

(b) Preparation of TDA-DTX Via Procedure B:

Prepared using Procedure B above, using DTX (400 mg, 0.50 mmol) and thiodiacetic anhydride (66 mg, 0.50 mmol) as the linker. The mixture was stirred at room temperature overnight then solvent was removed under reduced pressure to give a crude residue. The residue was re-dissolved in EtOAc (250 mL) and was washed with PBS buffer (adjusted to pH 4.0). The separated organic layer was dried over MgSO$_4$ and concentrated under reduced pressure to give 445 mg (95%) of the desired product as a white solid. LCMS (Waters XBridge C8 column (3.0×100 mm), 3.5 micron, 214, 243 nm, 0.4 mL/min, gradient: 40-90% ACN/H$_2$O (1-7 min), 90% ACN (7-9 min), 90-40% ACN (9-11 min), 40% ACN 11-15 min), 0.1% TFA) Rt (min)=10.60. ESI (+ve) observed [M+H]+=940. Calculated for C$_{47}$H$_{57}$NO$_{17}$S=939.33 Da.

(c) Preparation of BHALys[Lys]$_{32}$[α-TDA-DTX]$_{32}$[α-PEG$_{1100}$]$_{32}$

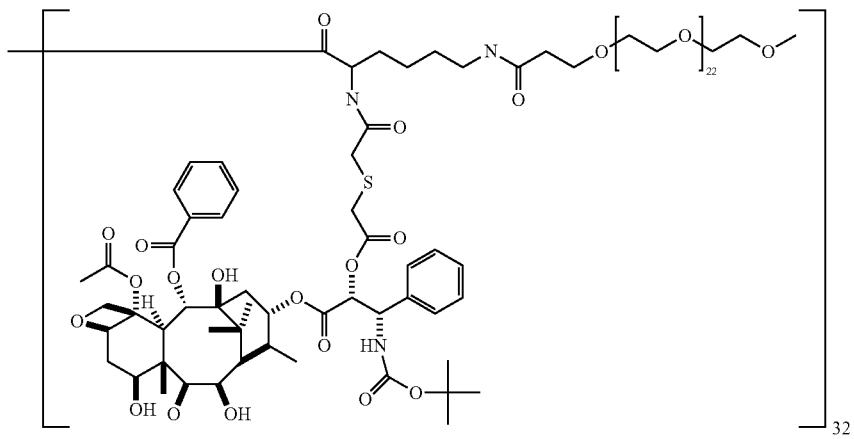

Prepared using Procedure C above, using BHALys[Lys]$_{32}$[α-NH$_2$·TFA][ε-PEG$_{1100}$]$_{32}$ (46 mg, 1.08 μmol) and TDA-DTX (44 mg, 47 μmol). Purification by SEC (sephadex, LH20, MeOH) provided 65 mg (87%) of desired material as a white solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rt (min) =9.68. $^1$H NMR (300 MHz, CD$_3$OD) δ (ppm): 0.78-2.02 (m, 809H), 2.27-2.58 (m, 114H), 3.03-3.24 (m, 43H), 3.34 (s, 73H), 3.37-3.96 (m, 2800H), 4.01-4.39 (m, 27H), 5.20-5.48 (m, 75H), 5.54-5.74 (m, 23H), 5.98-6.25 (m, 20H), 7.12-7.84 (m, 202H), 8.01-8.22 (m, 46H). Theoretical molecular weight of conjugate: 68.9 kDa. $^1$H NMR indicates 23 DTX/dendrimer. Actual molecular weight is approximately 60.6 kDa (31% DTX by weight). Particle sizing using Dynamic Light Scattering shows a range of concentration dependent averages of 8.9-10.1 nm.

Example 9

(a) Preparation of PDT-DTX:

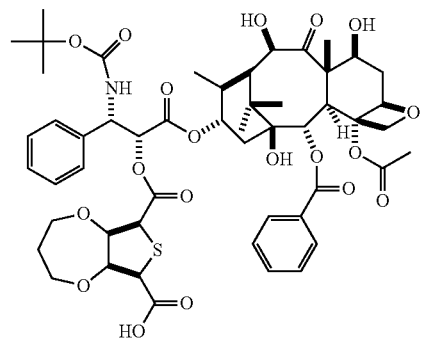

Prepared using Procedure A above, using DTX (250 mg, 0.31 mmol) and 3,4-propylenedioxythiophene-2,5-dicarboxylic acid (PDT, 75 mg, 0.31 mmol) as the linker. Purification by preparative HPLC (RT=28 min) provided 30 mg (9%) of product as a white solid. LCMS (C8, gradient: 40-90% ACN/H$_2$O (1-7 min), 90% ACN (7-9 min), 90-40% ACN (9-11 min), 40% ACN (11-15 min), 0.1% TFA) Rt (min)=7.24. ESI (+ve) observed [M+H]$^+$=1034. Calculated for C$_{52}$H$_{59}$NO$_{19}$S=1033.34 Da. $^1$H NMR (300 MHz, CD$_3$OD) δ (ppm): 1.14 (s, 3H), 1.18 (s, 3H), 1.45 (s, 9H), 1.71 (s, 3H), 1.78-1.91 (m, 2H), 1.94 (s, 3H), 2.09-2.27 (m, 1H), 2.29-2.58 (m, 3H), 2.41 (s, 3H), 3.88 (d, J=6.9 Hz, 1H), 4.20-4.30 (m, 3H), 4.31-4.43 (m, 4H), 4.94-5.16 (m, 1H), 5.30 (s, 1H), 5.36-5.42 (m, 2H), 5.65 (d, J=6.9 Hz, 1H), 6.02-6.22 (m, 1H), 7.23-7.34 (m, 1H), 7.36-7.53 (m, 4H), 7.56-7.65 (m, 2H), 7.66-7.77 (m, 1H), 8.11 (d, J=7.2 Hz, 2H).

(b) Preparation of BHALys[Lys]$_{32}$[α-PDT-DTX]$_{32}$[ε-PEG$_{1100}$]$_{32}$

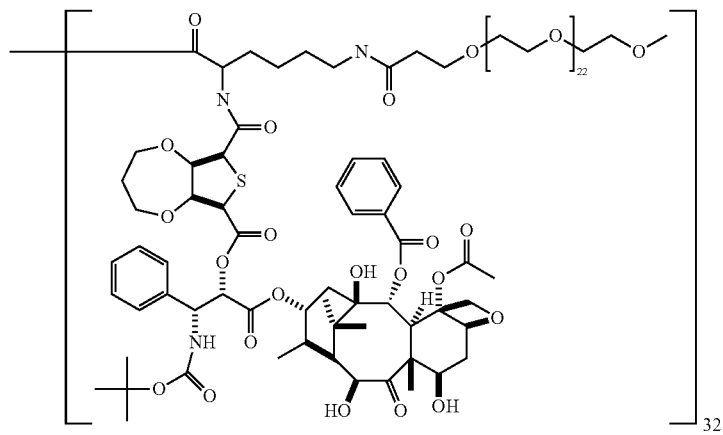

Prepared using Procedure C above, using BHALys[Lys]$_{32}$[α-NH$_2$.TFA][ε-PEG$_{1100}$]$_{32}$ (29 mg, 0.67 μmol) and PDT-DTX (30 mg, 29 μmol). Purification by SEC (sephadex, LH20, MeOH) provided 42 mg (88%) of desired material as a white solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rt (min) =9.03. $^1$H NMR (300 MHz, CD$_3$OD) δ (ppm): 0.76-2.10 (m, 974H), 2.23-2.66 (m, 210H), 3.08-3.30 (m, 74H), 3.40-3.98 (m, 2804H), 4.02-4.76 (m, 249H), 4.96-5.12 (m, 33H), 5.22-5.34 (m, 25H), 5.36-5.52 (m, 47H), 5.56-5.80 (m, 27H), 5.88-6.30 (m, 24H), 7.08-7.94 (m, 213H), 7.99-8.31 (m, 50H). Theoretical molecular weight of conjugate: 71.9 kDa. $^1$H NMR indicates 26 DTX/dendrimer. Actual molecular weight is approximately 66.3 kDa (32% DTX by weight).

Example 10

(a) Preparation of PEG$_2$-DTX:

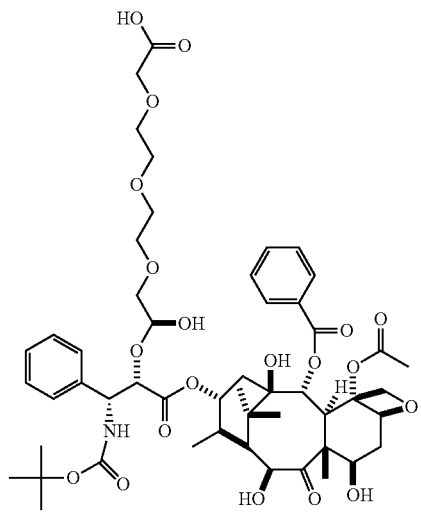

Prepared using Procedure A above, using DTX (200 mg, 0.25 mmol) and 3,6,9-trioxaundecanedioic acid (220 mg, 1.0 mmol). Preparative HPLC (RT=30.5 min) provided 70 mg (28%) of product as a white solid. LCMS (C8, gradient: 40-90% ACN/H$_2$O (1-7 min), 90% ACN (7-9 min), 90-40% ACN (9-11 min), 40% ACN (11-15 min), 0.1% Formic acid)

Rt (min)=6.48. ESI (+ve) observed [M+H]$^+$=1012.15. Calculated for $C_{51}H_{65}NO_{20}$=1011.41 Da. $^1$H NMR (300 MHz, CD$_3$OD) δ (ppm): 1.13 (s, 3H), 1.17 (s, 3H), 1.40 (s, 9H), 1.70 (s, 3H), 1.83 (ddd, J=13.8, 11.1 and 2.1 Hz, 1H), 1.93 (s, 3H), 1.92-2.12 (m, 1H), 2.17-2.38 (m, 1H), 2.42 (s, 3H), 2.46 (ddd, J=14.7, 9.9 and 6.6 Hz, 1H), 3.56-3.82 (m, 8H), 3.88 (d, J=7.0 Hz, 1H), 4.06 (s, 2H), 4.16-4.39 (m, 5H), 5.01 (d, J=9.3 Hz, 1H), 5.29 (s, 1H), 5.38 (s, 2H), 5.65 (d, J=7.0 Hz, 1H), 6.13 (t, J=8.4 Hz, 1H), 7.22-7.33 (m, 1H), 7.35-7.47 (m, 4H), 7.51-7.62 (m, 2H); 7.62-7.72 (m, 1H), 8.13 (d, J=7.2 Hz, 2H).

(b) Preparation of BHALys[Lys]$_{32}$[α-PEG$_2$-DTX]$_{32}$[ε-PEG$_{1100}$]$_{32}$

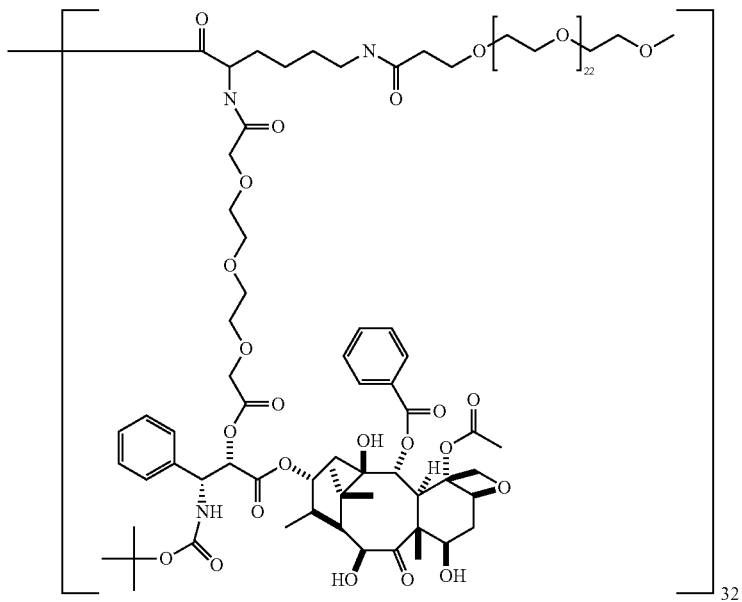

Prepared using Procedure C above, using BHALys[Lys]$_{32}$[α-NH$_2$.TFA][ε-PEG$_{1100}$]$_{32}$ (55.8 mg, 1.24 μmol) and PEG$_2$-DTX (50 mg, 49.5 μmol). Purification by SEC (sephadex, LH20, MeOH) provided 79 mg (>90%) of the desired product as a white solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rf (min)=8.65. $^1$H NMR (300 MHz, CD$_3$OD) δ (ppm): 0.91-2.14 (m, 968H), 2.14-2.64 (m, 185H), 2.88-3.29 (m, 109H), 3.35 (s, 89H), 3.36-3.95 (m, 3016H), 3.95-4.65 (m, 251H), 5.00 (br s, 32H); 5.20-5.49 (m, 72H), 5.55-5.75 (m, 25H), 6.13 (br s, 25H), 7.12-7.81 (m, 213H), 8.13 (d, J=7.2 Hz, 50H). Theoretical molecular weight of conjugate: 75.5 kDa. $^1$H NMR indicates 24 DTX/dendrimer. Actual molecular weight is approximately 63.2 kDa (31% DTX by weight).

Example 11

Preparation of BHALys[Lys]$_{32}$[α-Lys(α-Ac)(ε-DGA-DTX)]$_{32}$[ε-Lys(PEG$_{570}$)$_2$]$_{32}$ (a) Preparation of HO-Lys(NH$_2$.TFA)$_2$

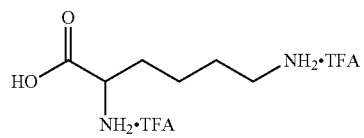

To a magnetically stirred suspension of L-lysine (500 mg, 3.42 mmol) in CH$_2$Cl$_2$ (21 mL) was added a solution of TFA in CH$_2$Cl$_2$ (21 mL, 1:1 v/v). The mixture was stirred at ambient temperature for 4 h, and then concentrated in vacuo. The residue was dissolved in water (30 mL) and concentrated in vacuo. This procedure was repeated once more. The remaining oil was then freeze-dried from water, providing 1.33 g of the desired product as a yellowish oil that was used directly in the next step.

(b) Preparation of HO-Lys(PEG$_{570}$)$_2$

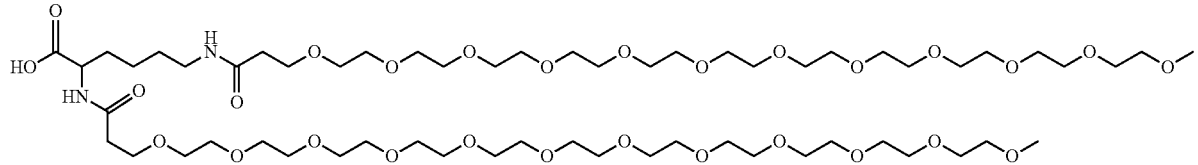 [SMILES: COCCOCCOCCOCCOCCOCCOCCOCCOCCOCCOCCOCCC(=O)NCCCCC(NC(=O)CCOCCOCCOCCOCCOCCOCCOCCOCCOCCOCCOCCOC)C(=O)O]

To a magnetically stirred solution of PEG$_{570}$-NHS (1.06 g, 1.55 mmol) in DMF (5 mL) was added DIPEA (806 μL, 4.64 mmol), followed by a solution of HO-Lys(NH$_2$.TFA)$_2$ (300 mg) in DMF (4 mL). The resulting mixture was stirred at ambient temperature overnight. The volatiles were then removed in vacuo and the residue purified by preparative HPLC (BEH 300 Waters XBridge C18, 5 μM, 30×150 mm, gradient: 5% ACN/H$_2$O (1-5 min), 5-60% ACN (5-35 min), 60-80% ACN (35-40 min), 80% ACN (40-45 min), 80-5% ACN (45-50 min), 5% ACN (50-60 min), no buffer, Rt=29.3 min). The appropriate fractions were concentrated in vacuo and freeze-dried in water, providing 481 mg (48% over two steps) of the desired product as a white semi-solid. HPLC (C18, gradient: 5-60% ACN/H$_2$O (1-10 min), 60% ACN (10-11 min), 60-5% ACN (11-13 min), 5% ACN (13-15 min), 10 mM ammonium formate) Rt (min)=8.68. $^1$H NMR (300 MHz, CD$_3$OD) δ (ppm): 1.33-1.62 (m, 4H), 1.62-1.95 (m, 2H), 2.43 (t, J=6.2 Hz, 2H), 2.52 (dt, J=6.2 and 3.6 Hz, 2H), 3.16-3.24 (m, 2H), 3.36 (s, 6H), 3.36-3.90 (m, 95H), 4.39 (dd, J=8.7 and 5.1 Hz, 1H).

(c) Preparation of BHALys[Lys]$_{16}$[Lys(α-Boc)(ε-NH$_2$]$_{32}$

To a magnetically stirred suspension of BHALys[Lys]$_{16}$[Lys(α-Boc)(ε-Fmoc)]$_{32}$ (500 mg, 26.9 μmol) in DMF (3.4 mL) was added piperidine (849 μL, 20% v/v in DMF). The mixture was stirred at ambient temperature overnight, then poured into diethyl ether (65 mL). The white precipitate that formed was filtered off and washed with diethyl ether (100 mL). The filter cake was transferred to a vial and air dried for 3 days, providing 281 mg (91%) product as a white solid. $^1$H NMR (300 MHz, CD$_3$OD) δ (ppm): 1.00-2.10 (m, 680H), 2.65-2.88 (br s, 48H), 2.91-2.98 (m, 11H), 2.99-3.28 (m, 78H), 3.81-4.21 (m, 33H), 4.21-4.55 (m, 32H), 6.21 (s, 1H), 7.20-7.41 (m, 10H).

(d) Preparation of BHALys[Lys]$_{32}$[α-Boc]$_{32}$[ε-Lys(PEG$_{570}$)$_2$]$_{32}$ To a magnetically stirred solution of BHALys[Lys]$_{16}$[Lys(α-Boc)(ε-NH$_2$)]$_{32}$ (49 mg, 4.33 μmol) in DMF and DMSO (3 mL, 5:1 v/v) was added DIPEA (96 μL, 554.2 μmol). The resulting solution was added to a solution of HO-Lys(PEG$_{570}$)$_2$ (223 mg, 173.3 μmol) and PyBOP (90 mg, 173.3 μmol) in DMF (5.5 mL). The mixture was stirred at ambient temperature overnight. The volatiles were then removed in vacuo and the residue purified by ultrafiltration (Pall Mini-mate™ Tangential Flow Filtration Capsules, Omega™ 10K Membrane, water). The remaining aqueous solution was freeze-dried, providing 120 mg (53%) of the desired product as a yellowish oil. $^1$H NMR (300 MHz, CD$_3$OD) δ (ppm): 1.18-1.98 (m, 863H), 2.38-2.63 (m, 123H), 3.04-3.30 (m, 194H), 3.36 (s, 172H), 3.38-3.91 (m, 2816H), 3.93-4.18 (br s, 35H), 4.18-4.47 (m, 63H), 4.47-4.60 (m, 12H), 6.18 (s, 1H), 7.19-7.43 (m, 10H).

(e) Preparation of BHALys[Lys]$_{32}$[α-NH$_2$.TFA]$_{32}$[ε-Lys(PEG$_{570}$)$_2$]$_{32}$ To a magnetically stirred solution of BHALys[Lys]$_{32}$[α-Boc]$_{32}$[ε-Lys(PEG$_{570}$)$_2$]$_{32}$ (120 mg, 2.3 μmol) in CH$_2$Cl$_2$ (2 mL) was added a solution of TFA in CH$_2$Cl$_2$ (2 mL, 1:1 v/v). The mixture was stirred at ambient temperature for 3.5 h, after which the solvents were evaporated in vacuo. The remaining oil was dissolved in water (5 mL) and the resulting solution concentrated in vacuo. This procedure was repeated one more time and the oil that remained was taken up in water and purified by SEC (PD-10 desalting columns, GE Healthcare, 17-0851-01, sephadex G-25 medium). The collected fractions were combined and freeze-dried from water to provide 93 mg (77%) of desired material as a yellowish oil. $^1$H NMR (300 MHz, CD$_3$OD) δ (ppm): 1.18-2.01 (m, 556H), 2.38-2.65 (m, 118H), 3.02-3.30 (m, 181H), 3.36 (s, 178H), 3.38-3.94 (m, 2816H), 4.09-4.55 (m, 63H), 6.13-6.22 (m, 1H), 7.19-7.45 (m, 10H).

(f) Preparation of BHALys[Lys]$_{32}$[α-NH$_2$.TFA]$_{32}$[ε-Lys(PEG$_{570}$)$_2$]$_{32}$ To a solution of BHALys[Lys]$_{32}$[α-NH$_2$.TFA]$_{32}$[ε-Lys(PEG$_{570}$)$_2$]$_{32}$ (93 mg, 1.8 μmol) in DMF (3.6 mL) was added DIPEA (40 μL, 230.4 μmol). The resulting solution was added to solid HO-Lys(α-Ac)(ε-Boc) (21 mg, 72 μmol) and PyBOP (37 mg, 72 μmol) contained in a second flask. The mixture was stirred at ambient temperature overnight. The volatiles were then removed in vacuo and the residue purified by SEC (sephadex, LH20, MeOH). The appropriate fractions, as judged by HPLC were combined and concentrated. The yellowish oil thus obtained was freeze dried from water to give 97 mg (94%) of the desired product as a slightly yellowish semi-solid. $^1$H NMR (300 MHz, CD$_3$OD)

δ (ppm): 1.10-2.15 (m, 1139H), 2.36-2.63 (m, 120H), 2.93-3.30 (m, 251H), 3.36 (s, 195H), 3.37-3.91 (m, 2816H), 4.16-4.51 (br s, 122H), 6.15-6.21 (m, 1H), 7.18-7.43 (m, 10H).

(g) Preparation of BHALys[Lys]$_{32}$[α-Lys(α-Ac)(ε-NH$_2$.TFA)]$_{32}$[ε-Lys(PEG$_{570}$)$_2$]$_{32}$ To a magnetically stirred solution of BHALys[Lys]$_{32}$[α-Lys(α-Ac)(ε-Boc)]$_{32}$[ε-Lys(PEG$_{570}$)$_2$]$_{32}$ (97 mg, 1.69 μmol) in CH$_2$Cl$_2$ (1 mL) was added a solution of TFA in CH$_2$Cl$_2$ (2 mL, 1:1 v/v). The mixture was stirred at ambient temperature overnight, and then the solvents were evaporated in vacuo. The remaining oil was dissolved in water (4 mL) and the resulting solution concentrated in vacuo. This procedure was repeated one more time and the oil that remained was taken up in water and purified by SEC (PD-10 desalting columns, GE Healthcare, 17-0851-01, sephadex 0-25 medium). The collected fractions were combined and freeze-dried from water to provide 104 mg (>90%) of the desired material as a yellowish oil. $^1$H NMR (300 MHz, CD$_3$OD) δ (ppm): 1.13-2.20 (m, 843H), 2.37-2.65 (m, 122H), 2.89-3.06 (m, 70H), 3.06-3.30 (m, 180H), 3.36 (s, 182H), 3.39-3.92 (m, 2816H), 4.08-4.47 (br s, 126H), 6.13-6.20 (m, 1H), 7.20-7.45 (m, 10H).

(h) Preparation of BHALys[Lys]$_{32}$[α-Lys(α-Ac)(εDGA-DTX)]$_{32}$[ε-Lys(PEG$_{570}$)$_2$]$_{32}$ Prepared using Procedure C above, using BHALys[Lys]$_{32}$[α-Lys(α-Ac)(ε-NH$_2$.TFA)]$_{32}$[ε-Lys(PEG$_{570}$)$_2$]$_{32}$ (49 mg, 0.85 μmol) and DOA-DTX (31 mg, 34 μmol). Purification by SEC (sephadex, LH20, MeOH) provided 57 mg (80%) of the desired product as a white solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rt (min)=8.85. $^1$H NMR (300 MHz, CD$_3$OD) δ (ppm): 0.79-2.73 (m, 1698H), 3.06-3.29 (m, 179H), 3.35 (s, 184H), 3.36-3.92 (m, 2848H), 3.95-4.60 (m, 332H), 5.01 (br s, 32H), 5.20-5.52 (m, 77H), 5.64 (br s, 30H), 6.13 (br s, 27H), 7.14-7.34 (m, 39H), 7.34-7.52 (m, 104H), 7.52-7.76 (m, 87H), 8.02-8.24 (m, 57H). Theoretical molecular weight of conjugate: 83.3 kDa. $^1$H NMR indicates 27 DTX/dendrimer. Actual molecular weight is approximately 78.8 kDa (28% DTX by weight).

Example 12

Preparation of BHALys[Lys]$_{32}$[α-Glu-PTX]$_{32}$[ε-PEG$_{2300}$]$_{32}$ PTX=Paclitaxel

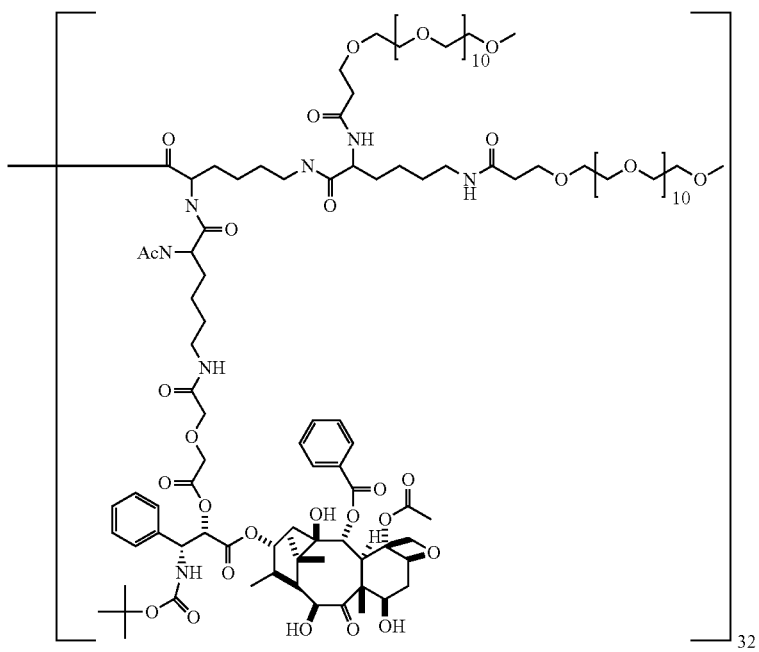

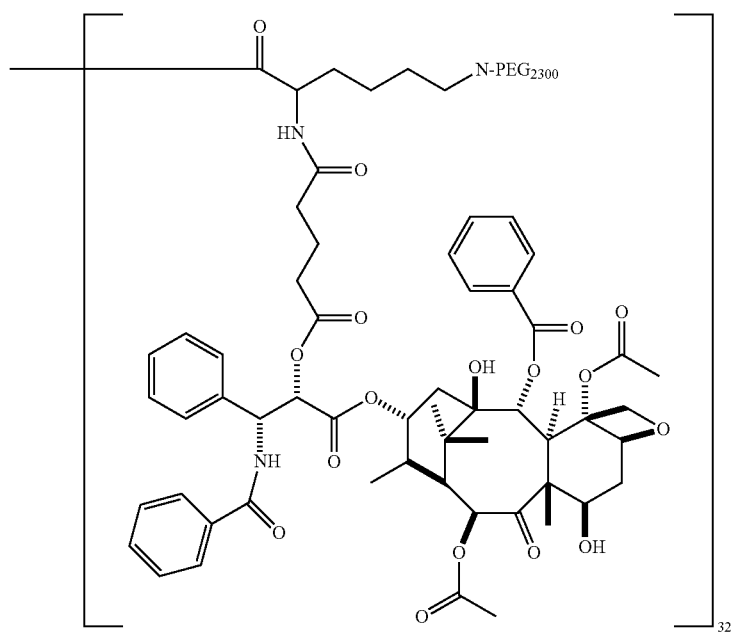

PEG₂₃₀₀ =

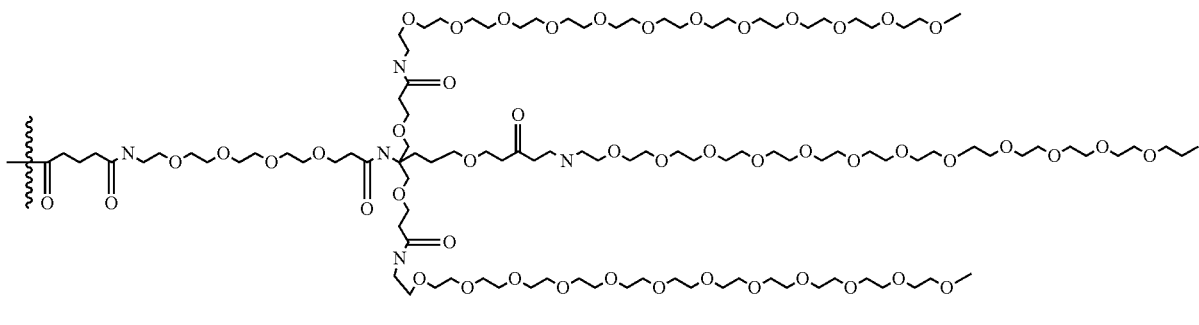

40

Prepared using Procedure C above, using Glu-PTX (300 mg, 371 μmol) and BHALys[Lys]₁₆[Lys(α-NH₂.TFA)(ε-PEG₂₃₀₀)]₃₂ (22.0 mg, 0.26 μmol). Purification by preparative HPLC (Rt=28 min) provided 12 mg (41%) of the desired dendrimer. $^1$H NMR (CD₃OD): δ 0.78-2.80 (m, 1785H), 2.96-3.23 (m, 120H), 3.35-3.45 (m, 567H), 3.46-3.94 (m, 5610H), 4.04-4.47 (m, 167H), 4.48-4.65 (m, 88H), 5.50 (m, 29H), 5.64 (m, 24H), 5.85 (m, 27H), 6.10 (m, 26H), 6.46 (m, 20H), 7.26 (m, 66H), 7.36-8.00 (m, 407H), 8.12 (s, 53H). Theoretical molecular weight of conjugate: 112.4 kDa. $^1$H NMR indicates 25 PTX/dendrimer. Actual molecular weight is approximately 105 kDa (20% PTX by weight).

Example 13

Preparation of BHALys[Lys]₃₂[α-Glu-GEM]₃₂[ε-PEG₁₁₀₀]₃₂ GEM=gemcitabine (a) Preparation of N,O-di-BOC-GEM-Glu

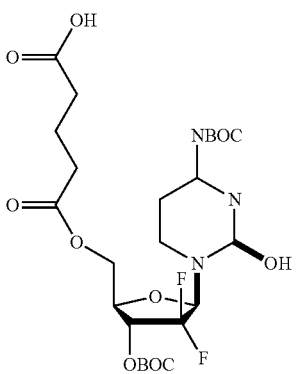

To a stirred mixture of N,O-diBoc gemicitabine (Guo, Z.; Gallo, J. M. Selective Protection of 2',2'Difluorodeoxycytidine *J. Org. Chem*, 1999, 64, 8319-8322) (200 mg, 0.43 mmol) in DMF (2 mL) at 0° C. was added DIPEA (0.4 mL, 2.15 mmol) and glutaric anhydride (100 mg, 0.86 mmol). The reaction was allowed to warm up to ambient temperature over 1 hour, then stirred for a further 3 hours. The DMF was then removed in vacuo and residue was taken up in ethyl acetate (20 mL). This mixture was then washed with NaHCO₃ (10%, 2×10 mL), water (2×20 mL) and brine (20 mL). The organic phase was then dried (Na$_2$SO$_4$), filtered and concentrated under reduced pressure. The crude was then purified by silica gel chromatography (DCM/Methanol) providing 130 mg (54%) of the desired product as a white solid. LCMS (C18, gradient: 20-60% ACN/H$_2$O (1-7 min), 60% ACN (7-9 min), 60-20% ACN (9-11 min), 20% ACN (11-15 min), 0.1% TFA, Rt (min)=10.8 min. ESI (+ve) observed [M+H]$^+$=578. Calculated for C$_{24}$H$_{32}$N$_3$F$_2$O$_{11}$=576.20 Da. $^1$H NMR (CDCl$_3$): δ 1.51 (s, 18H), 2.01-1.88 (m, 2H), 2.55-2.4 (m, 2H), 2.75-2.64 (m, 2H), 4.46-4.38 (m, 3H), 5.15-5.10 (m, 1H), 6.46-6.30 (m, 1H), 736-7.50 (d, J=7.8 Hz, 1H), 7.6-7.79 (d, J=7.8 Hz, 1H).

(b) Preparation of BHALys[Lys]$_{32}$[α-Glu-GEM]$_{32}$[ε-PEG$_{1100}$]$_{32}$

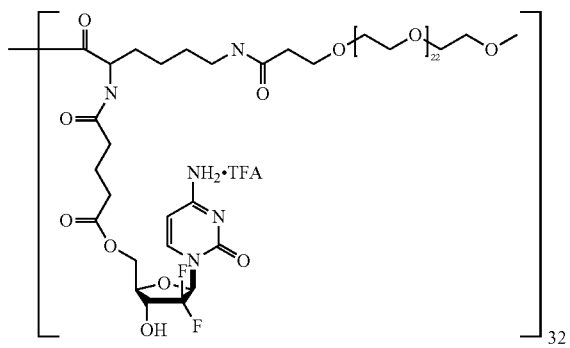

Prepared using Procedure C above, using BHALys[Lys]$_{16}$[Lys(α-NH$_2$.TFA)(ε-PEG)$_{1100}$]$_{32}$ (40 mg, 1.03 mmol) and N,O-di-Boc-GEM-Glu (28 mg, 49 μmol). Purification by SEC (PD-10 desalting column, GE Healthcare, 17-0851-01, sephadex G-25 medium) provided 20 mg of material. The solid was taken up in TFA/DCM (1:1, 2 mLs) and stirred for 3 hours at room temperature. The volatiles were removed in vacuo and the residue taken up in water and freeze dried, providing 18 mg (47%) of white powder. HPLC (C8, gradient: 40-80% ACN/H$_2$O (1-7 min), 80% ACN (7-9 min), 80-40% ACN (9-11 min), 40% ACN (11-15 min), 0.1% TFA), Rt (min)=6.06. $^1$H NMR (CD$_3$OD): δ 0.89-2.1 (m, 456H), 2.1-2.7 (m, 185H), 2.9-3.2 (m, 90H), 3.2-3.3 (m, 191H), 3.44-4.12 (m, 2650H), 4.14-4.70 (m, 160H), 5.8-6.0 (m, 28H), 6.2-6.4 (m, 28H), 7.05-7.15 (s, 11H), 7.5-7.7 (m, 24H). Theoretical molecular weight of conjugate: 59.2 kDa.

$^1$H NMR indicates 26 GEM/dendrimer. Actual molecular weight is approximately 52.3 kDa (15% GEM by weight).

Example 14

(a) Preparation of BHALys[Lys]$_{32}$[αGGG-Boc]$_{32}$[ε-PEG$_{1100}$]$_{32}$

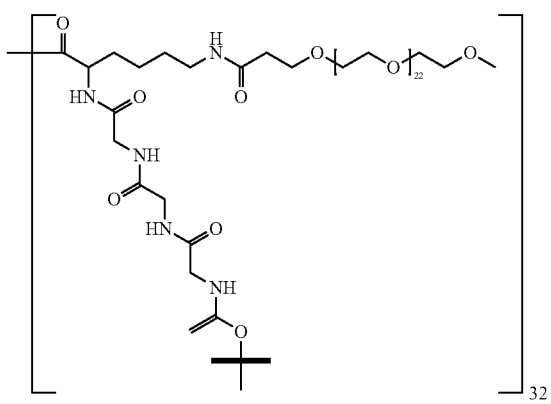

To a magnetically stirred solution of Boc-GGG-OH (28 mg, 93.2 μmol) and PyBOP (48 mg, 93.2 μmol) in DMF (1 mL) at room temperature was added a solution of BHALys[Lys]$_{32}$[α-NH$_2$.TFA]$_{32}$[ε-PEG$_{1100}$]$_{32}$ (100 mg, 2.33 μmol) and DIPEA (51 μL, 298.24 μmol) in DMF (2.6 mL). The mixture was stirred at room temperature for 18 b and then concentrated under reduced pressure. The residue was dissolved in MeOH (1 mL) and purified by SEC (Sephadex, LH-20, MeOH). The appropriate fractions, as judged by HPLC, were combined and concentrated to provide 98 mg of product as a clear, colourless oil. The latter was dissolved in MQ water and lyophilised to give 98 mg (87%) of product as a colourless resin. LCMS (C8, gradient: 5-80% ACN/H$_2$O (1-7 min), 80% ACN (7-12 min), 80-5% ACN (12-13 min), 5% ACN (13-15 min), 0.1% TFA) Rt (min)=8.63. $^1$H NMR (300 MHz, CD$_3$OD) δ (ppm): 1.15-2.01 (m, 693H), 2.46 (br s, 57H), 3.18 (br s, 101H), 3.35 (s, 53H), 3.36 (s, 84H), 3.38-4.04 (m, 2990H), 4.30 (br s, 63H), 6.17 (br s, 1H), 7.29 (br s, 9H). $^1$H NMR indicates ca. 32 Boc-GGG/dendrimer. Molecular weight is approximately 48.5 kDa.

(b) Preparation of BHALys[Lys]$_{32}$[α-GGG-NH$_2$.TFA]$_{32}$[ε-PEG$_{1100}$]$_{32}$

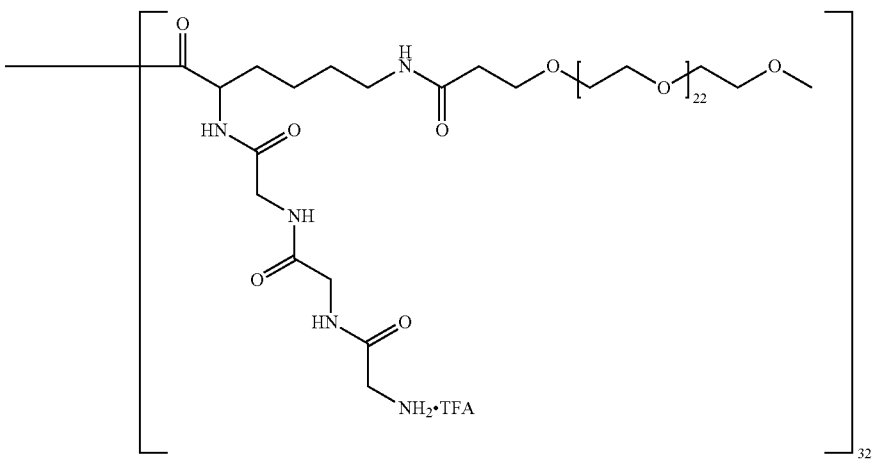

To a magnetically stirred mixture of BHALys[Lys]$_{32}$[α-GGG-Boc]$_{32}$[ε-PEG$_{1100}$]$_{32}$ (98 mg, 2.02 μmol) in CH$_2$Cl$_2$ (1 mL) at room temperature was added a solution of TFA in CH$_2$Cl$_2$ (1:1, 2 mL). After 18 hours at room temperature the volatiles were removed. The resulting residue was dissolved in MQ water (15 mL) and concentrated. This procedure was repeated once more. The residue was then dissolved in MQ water (12.5 mL) and purified by SEC (PD-10, MQ water). The appropriate fractions were combined and lyophilised to provide 92 mg (94%) of desired material as a clear, colourless oil. HPLC (C8, gradient: 5-80% s ACN/H$_2$O (1-7 min), 80% ACN (7-12 min), 80-5% ACN (12-13 min), 5% ACN (13-15 min), 0.1% TFA) Rt (min)=7.94. $^1$H NMR (300 MHz, CD$_3$OD) δ (ppm): 1.19-2.05 (m, 351H), 2.47 (br s, 58H), 3.18 (br s, 105H), 3.36 (s, 89H), 3.38-4.15 (m, 2990H), 4.31 (br s, 72H), 6.17 (br s, 1H), 7.30 (br s, 9H). $^1$H NMR indicates ca. 32 GGG-NH$_2$.TFA/dendrimer. Molecular weight is approximately 48.6 kDa.

(c) Preparation of BHALys[Lys]$_{32}$[α-GGG-Glu-DTX]$_{32}$[ε-PEG$_{1100}$]$_{32}$

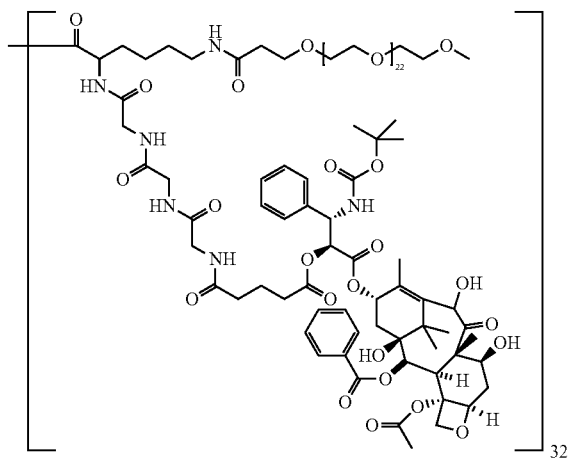

Prepared using Procedure C above, using BHALys[Lys]$_{32}$[(α-GGG-NH$_2$.TFA]$_{32}$[ε-PEG$_{1100}$]$_{32}$ (75 mg, 1.53 μmol) and Glu-DTX (56 mg, 61.2 μmol). Purification by SEC (Sephadex, LH-20, MeOH) provided 96 mg (92%) of product as a white solid. HPLC (C8, gradient: 5-80% ACN/H$_2$O (1-7 min), 80% ACN (7-12 min), 80-5% ACN (12-13 min), 5% ACN (13-15 min), 0.1% TFA) Rt (min)=10.08. $^1$H NMR (300 MHz, CD$_3$OD) δ (ppm): 0.75-2.02 (m, 985H), 2.02-2.64 (m, 309H), 2.92-3.17 (m, 53H), 3.25 (s, 89H), 3.26-4.00 (m, 3070H), 4.00-4.40 (m, 174H), 4.82-5.00 (m, 44H), 5.04-5.39 (m, 87H), 5.54 (br s, 27H), 6.01 (br s, 22H), 7.03-7.67 (m, 227H), 7.92-8.10 (m, 49H). Theoretical molecular weight of conjugate: 73.9 kDa. $^1$H NMR indicates 32 GGG and 26 DTX/dendrimer. Actual molecular weight is approximately 68.5 kDa (31% DTX by weight).

Example 15

(a) Preparation of BHALys[Lys]$_{32}$[α-GFLG-Boc]$_{32}$[ε-PEG$_{1100}$]$_{32}$

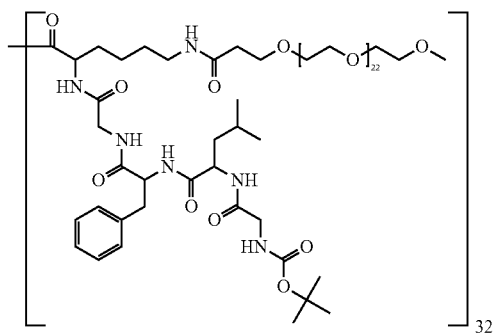

To a magnetically stirred solution of Boc-GLFG-OH (32 mg, 65.2 μmol) and PyBOP (34 mg, 65.2 μmol) in DMF (1 mL) at room temperature was added a solution of BHALys[Lys]$_{32}$[α-NH$_2$.TFA]$_{32}$[ε-PEG$_{1100}$]$_{32}$ (70 mg, 1.63 μmol) and DIPEA (36 μL, 208.64 μmol) in DMF (1.5 mL). The mixture was stirred at room temperature for 18 h and then concentrated under reduced pressure. The residue was dissolved in MeOH (1 mL) and purified by SEC (Sephadex, LH-20, MeOH). The appropriate fractions, as judged by HPLC, were combined and concentrated to provide 77 mg (88%) of product as a clear, colourless oil. HPLC (C8, gradient: 5-80% ACN/H$_2$O (1-7 min), 80% ACN (7-12 min), 80-5% ACN (12-13 min), 5% ACN (13-15 min), 0.1% TFA) Rt (min) 9.14. $^1$H NMR (300 MHz, CD$_3$OD) δ (ppm): 0.63-1.06 (m, 211H), 1.06-2.11 (m, 789H), 2.32-2.62 (m, 61H), 2.88-3.28 (m, 148H), 3.36 (s, 95H), 3.37-4.00 (m, 2920H), 4.17-4.69 (m, 132H), 7.23 (br s, 140H). $^1$H NMR indicates ca. 30 Boc-GLFG/dendrimer. Molecular weight is approximately 53.8 kDa.

(b) Preparation of BHALys[Lys]$_{32}$α-[αGFLG-NH$_2$.TFA]$_{32}$[ε-PEG$_{1100}$]$_{32}$

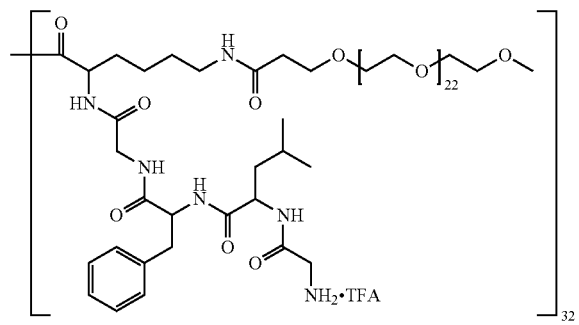

To a magnetically stirred mixture of BHALys[Lys]$_{32}$[α-GFLG-Boc]$_{32}$[ε-PEG$_{1100}$]$_{32}$ (77 mg, 1.43 μmol) in CH$_2$Cl$_2$ (1 mL) at room temperature was added a solution of TFA in CH$_2$Cl$_2$ (1:1, 2 mL). After 3 hours at room temperature the volatiles were removed. The resulting residue was dissolved in MQ water (15 mL) and concentrated. This procedure was repeated once more. The residue was then dissolved in MQ water (15 mL) and lyophilised to provide 76 mg (99%) of desired material as a yellowish resin. HPLC (C8, gradient: 5-80% ACN/H$_2$O (1-7 min), 80% ACN (7-12 min), 80-5% ACN (12-13 min), 5% ACN (13-15 min), 0.1% TFA) Rt (min)=8.08. $^1$H NMR (300 MHz, CD$_3$OD) δ (ppm): 0.75-1.04 (m, 197H), 1.10-2.09 (m, 480H), 2.45 (m, 56H), 2.88-3.29 (m, 146), 3.35 (s, 90H), 3.37-4.05 (m, 2920H), 4.17-4.69 (m, 133H), 7.66 (s, 159H). Theoretical molecular weight of conjugate: 68.9 kDa. $^1$H NMR indicates ca. 30 GFLG-NH$_2$.TFA/dendrimer. Molecular weight is approximately 54.1 kDa.

(c) Preparation of BHALys[Lys]$_{32}$[α-GFLG-Glu-DTX]$_{32}$[ε-PEG$_{1100}$]$_{32}$

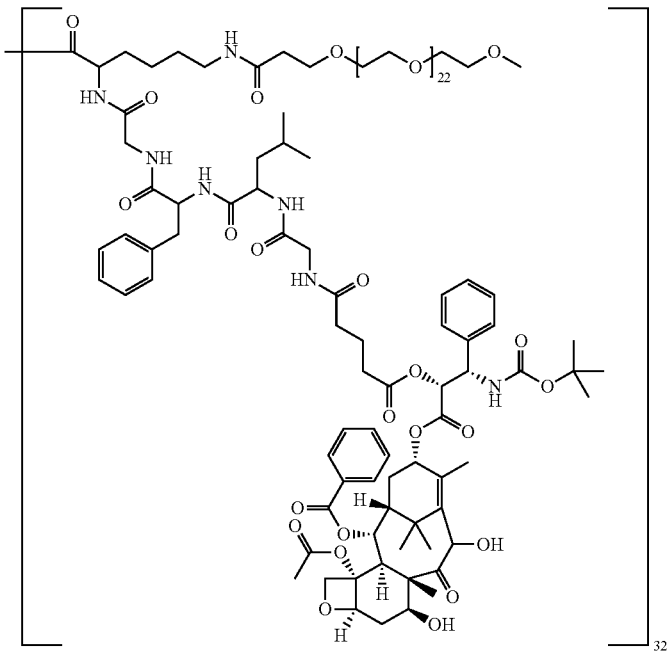

Prepared using Procedure C above, using BHALys[Lys]$_{32}$[α-GFLG-NH$_2$.TFA]$_{32}$[ε-PEG$_{1100}$]$_{32}$ (61 mg, 1.13 μmol) and Glu-DTX (42 mg, 45.60 μmol). Purification by SEC (Sephadex, LH-20, MeOH) provided 68 mg (85%) of product as a white solid. HPLC (C8, gradient: 5-80% ACN/H$_2$O (1-7 min), 80% ACN (7-12 min), 80-5% ACN (12-13 min), 5% (ACN 13-15 min), 0.1% TFA) Rt (min)=10.16. $^1$H NMR (300 MHz, CD$_3$OD) δ (ppm): 0.85 (s, 173H); 0.99-2.13 (m, 1153H), 2.15-2.62 (m, 312H), 2.91-3.27 (m, 128H), 3.35 (s, 93), 3.36-4.00 (m, 2970H), 4.05-4.68 (m, 237H), 4.94-5.07 (m, 32H), 5.15-5.47 (m, 76H), 5.52-5.76 (m, 24H), 5.97-6.26 (s, 21H), 6.99-7.77 (m, 380H), 7.98-8.24 (m, 48H).

Theoretical molecular weight of conjugate: 80.4 kDa. $^1$H NMR indicates 30 GLFG and 22 DTX/dendrimer. Actual molecular weight is approximately 70.6 kDa (25% DTX by weight).

Example 16

Preparation of BHALys[Lys]$_{32}$[α-GILGVP-Glu-DTX]$_{32}$[ε-PEG$_{1100}$]$_{32}$

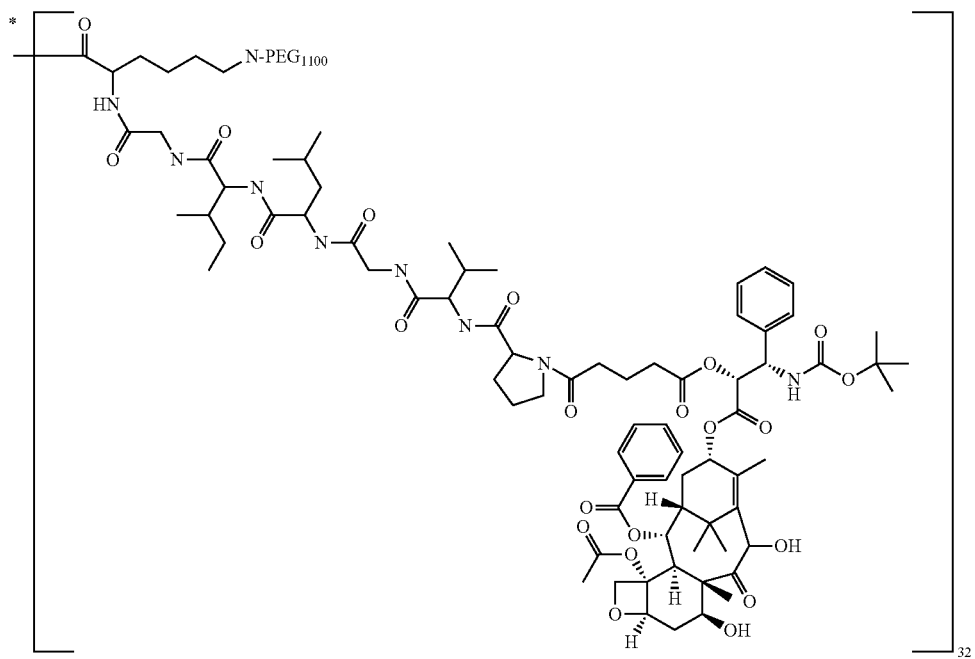

* - BHALys[Lys]$_{16}$

Prepared using Procedure C above, using BHALys[Lys]$_{32}$[ε-GILGVP-NH.TFA]$_{32}$[α-PEG$_{1100}$]$_{32}$ (52 mg, 0.86 μmol) and Glu-DTX (34 mg, 36 μmol). Purification by SEC (sephadex, LH20, MeOH) provided 59 mg (80%) of desired material as a hygroscopic colourless solid. HPLC (C8, gradient: 5-80% ACN/H$_2$O (1-7 min), 80% ACN (7-12 min), 80-5% ACN (12-13 min), 5% ACN (13-15 min), 0.1% TFA buffer) Rt (min)=10.45. $^1$H NMR (300 MHz, CD$_3$OD) δ 7.88 (m, 288H), 8.08-8.16 (m, 86H). Theoretical molecular weight of conjugate: 85.6 kDa. $^1$H NMR indicates 30 DTX/dendrimer. Actual molecular weight is approximately 83.2 kDa (29% DTX by weight).

Example 17

Preparation of BHALys[Lys]$_{32}$[α-GILGVP-Glu-DTX]$_{32}$ [ε-t-PEG$_{2300}$]$_{32}$

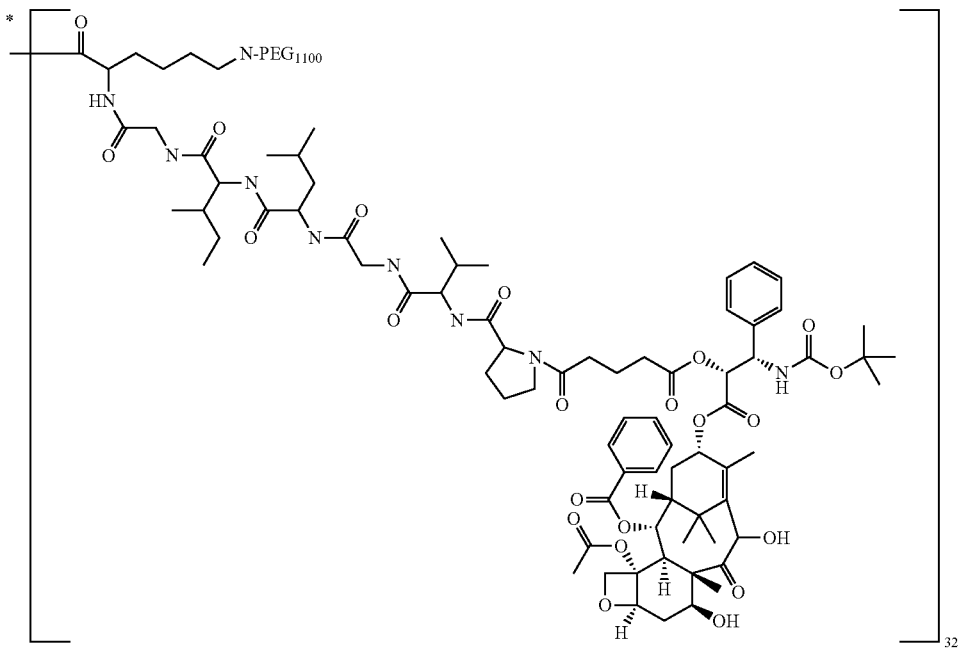

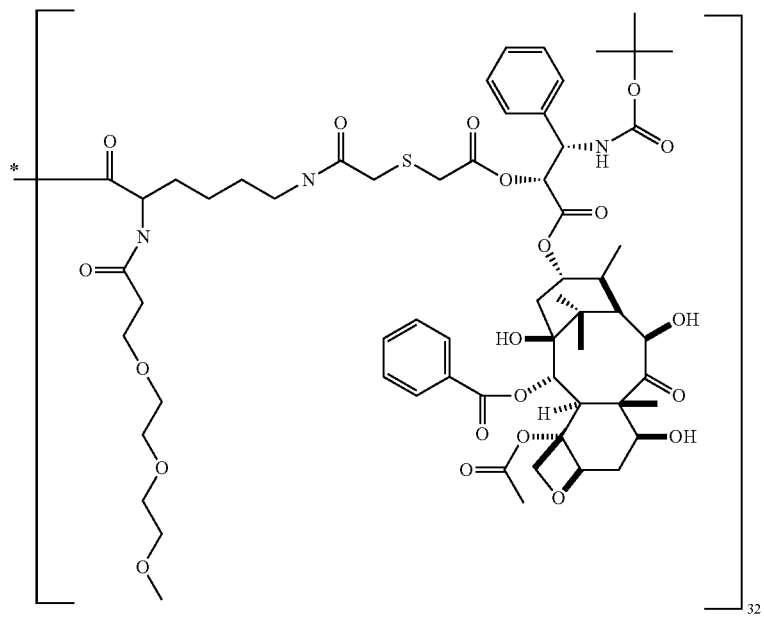

\* = BHALys[Lys]$_{16}$ (ppm): 0.84-1.91 (m, 1808H), 2.41 (s, 287H), 3.12-3.20 (m, 106H), 3.35 (bd, 166H), 3.37-3.90 (m, 2800H), 4.10-4.40 (bm, 194H), 4.53 (s, 88H), 4.98-5.03 (m, 35H), 5.24-5.40 (m, 80H), 5.60-5.68 (m, 26H), 6.08-6.16 (m, 21H), 7.25-

Prepared using Procedure C above, using BHALys[Lys]$_{32}$[α-GILGVP-NH$_2$.TFA]$_{32}$[ε-t-PEG$_{2300}$]$_{32}$ (59 mg, 0.57 μmol) and Glu-DTX (23 mg, 25 μmol) and PyBOP (13 mg, 25 μmol) Purification by SEC (sephadex, LH20, MeOH)

provided 65 mg (89%) of desired material as a hygroscopic colourless solid. HPLC (C8, gradient: 5-80% ACN/H$_2$O (1-7 min), 80% ACN (7-12 min), 80-5% ACN (12-13 min), 5% ACN (13-15 min), 0.1% TFA buffer) Rt (min)=9.22. $^1$H NMR (300 MHz, CD$_3$OD) δ (ppm): 0.86-2.50 (m, 2622H), 3.12-3.20 (m, 80H), 3.35-3.88 (m, 5540H), 4.18-4.30 (bm, 263H), 4.50-4.58 (m, 149H), 4.96-5.04 (m, 42H), 5.24-5.38 (m, 77H), 5.62-5.68 (m, 29H), 6.08-6.14 (m, 28H), 7.25-7.70 (m, 234H), 8.10-8.15 (m, 63H). Theoretical molecular weight of conjugate: 127.3 kDa. $^1$H NMR indicates 27 DTX/dendrimer. Actual molecular weight is approximately 123.7 kDa (18% DTX by weight).

Example 18

Preparation of BHALys[Lys]$_{32}$[α-PEG$_{1100}$]$_{32}$[ε-TDA-DTX]$_{32}$

Prepared using Procedure C above, using BHALys[Lys]$_{32}$[—NH$_2$.TFA]$_{32}$[α-PEG$_{1100}$]$_{32}$ (57.5 mg, 1.34 μmol) and TDA-DTX (52.3 mg, 56 μmol). Purification by SEC (sephadex, LH20, MeOH) provided 70 mg (92%) of desired material as a hygroscopic colourless solid. HPLC (C8, gradient 5-80% ACN/H$_2$O (1-7 min), 80% ACN (7-12 min), 80-5% ACN (12-13 min), 5% ACN (13-15 min), 0.1% TFA buffer) Rt (min)=9.89. $^1$H NMR (300 MHz, CD$_3$OD) δ (ppm): 1.06-1.95 (m, 784H), 2.36-2.55 (m, 168H), 3.04-3.23 (m, 48H), 3.33 (s, 84H), 3.35-3.89 (m, 2800H), 4.13-4.40 (m, 118H), 5.23-5.40 (m, 72H), 5.59-5.66 (m, 24H), 6.06-6.16 (m, 23H), 7.25-7.65 (m, 234H), 8.10-8.12 (m, 52H). Theoretical molecular weight of conjugate: 68.9 kDa. $^1$H NMR indicates 27 DTX/dendrimer. Actual molecular weight is approximately 64.4 kDa (34% DTX by weight).

Example 19

Preparation of BHALys[LYS]$_{32}$[α-TDA-DTX]$_{32}$[ε-PolyPEG$_{2000}$]$_{32}$

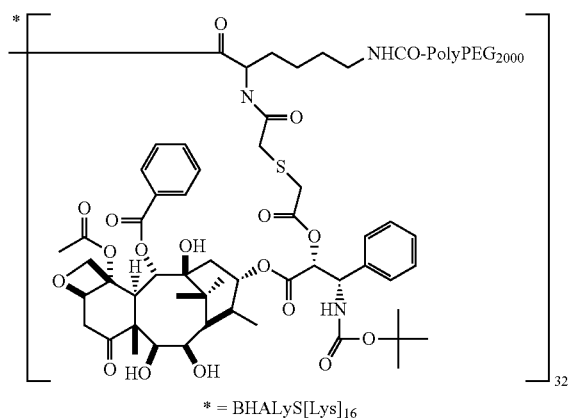

* = BHALyS[Lys]$_{16}$

Prepared using Procedure C above, using BHALys[Lys]$_{32}$[α-NH$_2$.TFA]$_{32}$[ε-PEG$_{2000}$]$_{32}$ (88.6 mg, 1.2 μmol) and TDA-DTX (49.3 mg, 52 μmol). Purification by SEC (sephadex, LH20, MeOH) provided 95 mg (80%) of desired material as a hygroscopic colourless solid. HPLC (C8, gradient: 45-85% ACN/H$_2$O (1-7 min), 85% ACN (7-12 min), 85-45% ACN (12-13 min), 45% ACN (13-15 min), 0.1% TFA buffer) Rf (min)=6.29 min. $^1$H NMR (300 MHz, CD$_3$OD) δ (ppm): 0.82-1.96 (m, 2076H), 2.36-2.54 (m, 314H), 3.10-3.24 (m, 125H), 3.35-3.89 (m, 6300H), 4.96-5.04 (m, 35H), 525-5.45 (m, 79H), 5.60-5.70 (m, 29H), 6.06-6.18 (m, 24H), 7.20-7.75 (m, 269H), 8.06-8.16 (m, 52H). Theoretical molecular weight of conjugate: 101.1 kDa. $^1$H NMR indicates 27 DTX/dendrimer. Actual molecular weight is approximately 95.5 kDa (23% DTX by weight). Particle sizing using Dynamic Light Scattering shows a range of concentration dependent averages of 10.9-15.5 nm.

Example 20

Preparation of BHALys[Lys]$_{32}$[α-DGA-testosterone]$_{32}$[ε-PEG$_{1100}$]$_{32}$ (a) Preparation of DGA-Testosterone

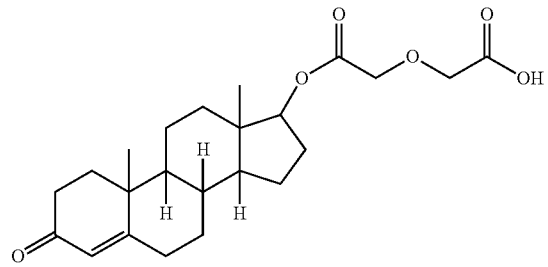

Prepared using Procedure B above, using testosterone (256 mg, 0.88 mmol), pyridine (10 mL) as the solvent and diglycolic anhydride (1.02 g, 8.8 mmol) as the linker. Purification by preparatory HPLC (BEH 300 Waters XBridge C18, 5 μM, 30×150 mm, 40-90% ACN/water, no buffer, RT=62 min) to give the desired compound 241 mg (67% yield) as an off white hygroscopic solid. LCMS (C8, gradient: 40-90% ACN/H$_2$O (1-7 min), 90% ACN (7-9 min), 90-40% ACN (9-11 min), 40% ACN (11-15 min), 0.1% TFA) Rt(min)=5.61. ESI (-ve) observed [M–H]$^-$=403.29. Calculated for C23H$_{31}$O$_6$=403.21 Da. $^1$H NMR (300 MHz, CD$_3$OD) δ (ppm) 0.88 (s, 3H, CH$_3$), 0.93-1.23 (m, 3H), 1.24 (s, 3H, CH$_3$), 1.25-2.58 (br m, 16H), 4.18 (s, 2H, CH$_2$), 4.23 (s, 2H, CH$_2$), 4.70 (m, 1H, CH), 5.71 (s, 1H, CH).

(b) Preparation of BHALys[Lys]$_{32}$[α-DGA-Testosterone]$_{32}$[α-PEG$_{1100}$]$_{32}$

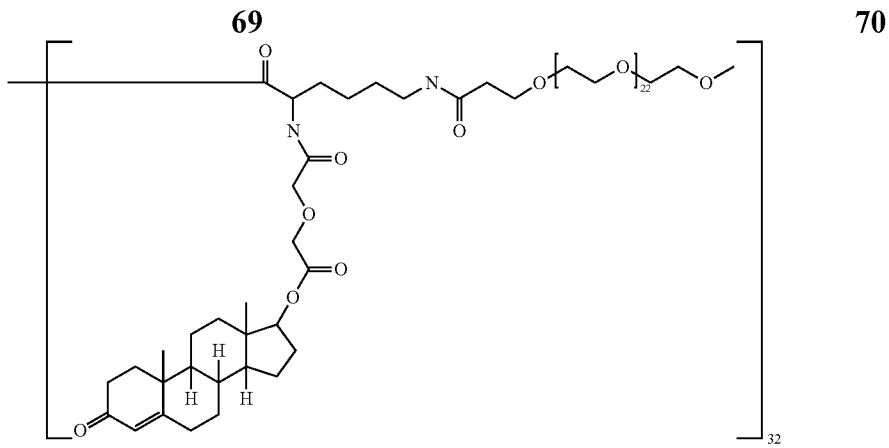

Prepared using Procedure C above, using BHALys[Lys]$_{32}$(α-NH$_2$.TFA)$_{32}$(ε-PEG$_{1100}$)$_{32}$ (30 mg, 0.75 μmol) and DGA-Testosterone (19 mg, 47 μmol). Purification by SEC (LH20, eluent: methanol) provided 15 mg (39%) as an off-white solid. HPLC (C8, gradient: 30-80% ACN/H$_2$O (1-7 min), 80% ACN (7-9 min), 80-30% ACN (9-11 min), 30% ACN (11-15 min), 10 mM ammonium formate) Rt(min)=9.41. $^1$H NMR (300 MHz, CD$_3$OD) δ (ppm) 0.79 (s, 80H, CH$_3$), 0.81-2.42 (br m, 1101H), 3.08 (m, 116H, CH$_2$), 3.26 (s, 98H, CH$_2$), 3.37-3.81 (m, 2800H, CH$_2$), 3.95-4.47 (m, 173H, CH), 4.61 (m, 29H, CH), 5.62 (s, 29H, CH), 6.08 (m, 1H, CH), 7.17 (m, 10H, ArH). Theoretical molecular weight of conjugate: 52.4 kDa. $^1$H NMR indicates 29 testosterone/dendrimer. Actual molecular weight is approximately 51.2 kDa (16% testosterone by weight).

Example 21

Preparation of BHALys[Lys]$_{32}$[α-DGA-Testosterone]$_{32}$[ε-PEG$_{570}$]$_{32}$

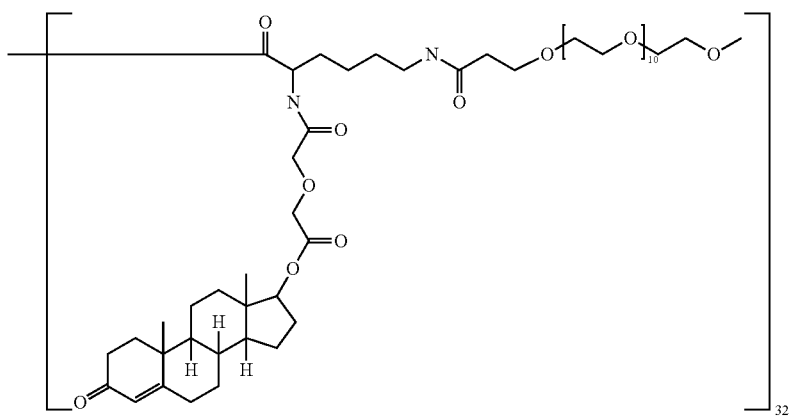

Prepared using Procedure C above, using BHALys[Lys]$_{32}$(α-NH$_2$.TFA)$_{32}$(ε-PEG$_{570}$)$_{32}$ (40 mg, 1.33 μmol) in DMF (2 mL) and DOA-Testosterone (43 mg, 106 μmol). Purification by SEC (LH20, eluent: methanol) provided 22.1 mg (40% yield) as a white hygroscopic solid. HPLC (C8, gradient: 30-80% ACN/H$_2$O (1-7 min), 80% ACN (7-9 min), 80-30% ACN (9-11 min), 30% ACN (11-15 min), 10 mM ammonium formate) Rt (min)=9.99. $^1$H NMR (300 MHz, CD$_3$OD) δ (ppm) 0.89 (s, 96H, CH$_3$), 0.90-2.63 (br m, 1214H), 3.36 (m, 125H, CH$_2$), 3.36 (s, 100H, CH$_3$), 3.45-3.97 (m, 1472H, CH$_2$), 4.05-4.62 (m, 218H), 4.71 (m, 37H, CH), 5.72 (s, 31H, CH), 6.18 (m, 1H, CH), 7.17 (m, 10H, ArH). Theoretical molecular weight of conjugate: 42.5 kDa. $^1$H NMR indicates 31 testosterone/dendrimer. Actual molecular weight is approximately 42.1 kDa (21% testosterone by weight).

Example 22

Preparation of BHALys[Lys]$_{32}$[α-Glu-testosterone]$_{32}$[ε-PEG$_{1100}$]$_{32}$ (a) Preparation of Glu-Testosterone

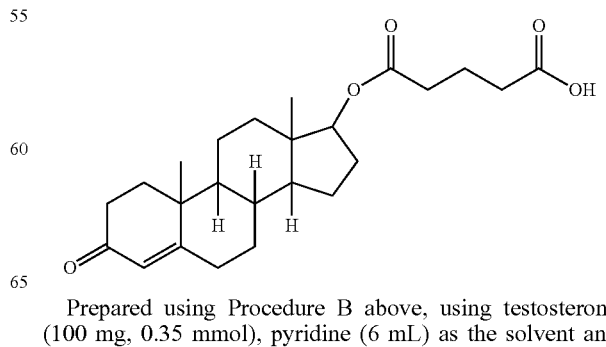

Prepared using Procedure B above, using testosterone (100 mg, 0.35 mmol), pyridine (6 mL) as the solvent and glutaric anhydride (396 mg, 3.5 mmol) as the linker. Purification by preparatory HPLC (BEH 300 Waters XBridge C18, 5 μM, 30×150 mm, 40-90% ACN/water, no buffer, RT 62 min) to give the desired compound 86 mg (86%) as an off white hygroscopic solid. LCMS (C8, gradient: 40-90% ACN/H$_2$O (1-7 min), 90% ACN (7-9 min), 90-40% ACN (9-11 min), 40% ACN (11-15 min), 0.1% TFA) Rt (min)=6.40. ESI (+ve) observed [M+H]$^+$=403.29. Calculated for C$_{24}$H$_{35}$O$_5$-403.25 Da. $^1$H NMR (300 MHz, CD$_3$OD) δ (ppm) 0.89 (s, 3H, CH$_3$), 0.93-1.23 (m, 3H), 1.24 (s, 3H, CH$_3$), 1.36-2.57 (br m, 22H), 4.62 (m, 1H, CH), 5.71 (s, 1H, CH).

(b) Preparation of BHALys[Lys]$_{32}$[α-Glu-Testosterone]$_{32}$ [ε-PEG$_{1100}$]$_{32}$ of the desired product as an off-white solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rt (min)=7.22. $^1$H NMR (300 MHz, CD$_3$OD) δ (ppm) 0.88 (s, 87H, CH$_3$), 0.89-2.61 (br m, 1225H), 3.17 (m, 110H, CH$_2$), 3.36 (s, 101H, CH$_3$), 3.46-3.98 (m, 2800H, CH$_2$), 4.34 (m, 59H, CH), 4.61 (m, 30H, CH), 5.72 (s, 29H, CH), 6.18 (m, 1H, CH), 7.28 (m, 12H, ArH). Theoretical molecular weight of conjugate: 52.3 kDa. $^1$H NMR indicates 29 testosterone/dendrimer. Actual molecular weight is approximately 51.1 kDa (16% testosterone by weight).

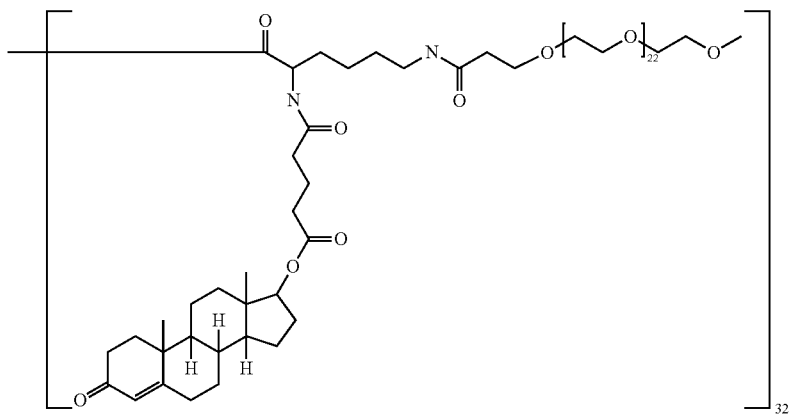

Prepared using Procedure C above, using BHALys[Lys]$_{32}$(α-NH$_2$.TFA)$_{32}$(ε-PEG$_{1100}$)$_{32}$ (30 mg, 0.75 μmol) in DMF (2 mL) and Glu-Testosterone (19 mg, 47 μmol). Purification by SEC (LH20, eluent: methanol) provided 18.1 mg (47%)

Example 23

Preparation of BHALys[Lys]$_{32}$[α-Glu-Testosterone]$_{32}$[ε-PEG$_{570}$]$_{32}$

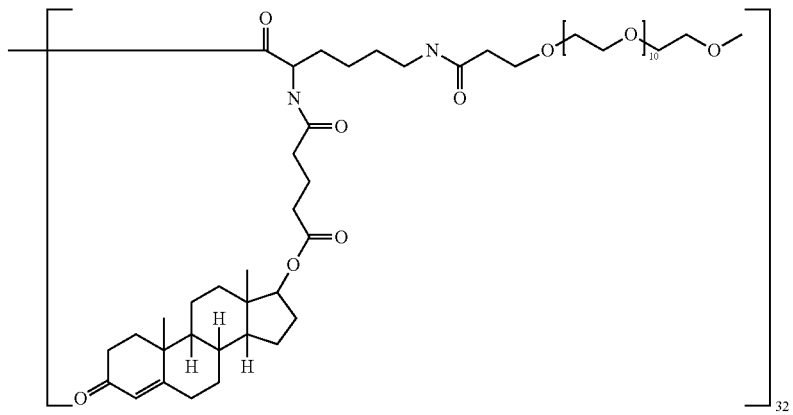

Prepared using Procedure C above, using BHALys[Lys]$_{32}$(α-NH$_2$.TFA)$_{32}$(ε-PEG$_{570}$)$_{32}$ (30 mg, 1 μmol) in DMF (2 mL) and Example 22(a), Glu-Testosterone (26 mg, 64 μmol). Purification by SEC (LH20, eluent: methanol) provided 19.8 mg (47% yield) of the desired product as a white solid product. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rt (min) =8.93. $^1$H NMR (300 MHz, CD$_3$OD) δ (ppm): 0.88 (s, 96H, CH$_3$), 0.89-2.59 (br m, 1423H), 3.16 (m, 127H, CH$_2$), 3.26 (m, 135H, CH$_3$), 3.65-3.92 (m, 1472H, CH$_2$), 4.24 (m, 66H, CH), 4.52 (m, 39H, CH), 5.62 (s, 32H, CH), 6.09 (m, 1H, CH), 7.19 (m, 10H, ArH). Theoretical molecular weight of ACN (45-50 min), 5% ACN (50-60 min), 0.1% TFA, Rt=27 min) provided 50 mg (34%) of the desired product as a white solid. HPLC (C18, gradient: 5-60% ACN/H$_2$O (1-10 min), 60% ACN (10-11 min), 60-5% ACN (11-13 min), 5% ACN (13-15 min), 10 mM ammonium formate) Rt (min)=6.67. ESI (+ve) observed [M+H]$^+$=354. Calculated for C$_{18}$H$_{27}$NO$_6$=353.18 Da. $^1$H NMR (300 MHz, CD$_3$OD) δ (ppm): 1.41 (s, 9H), 1.92 (t, J=7.2 Hz, 2H), 2.37 (t, J=7.5 Hz, 2H), 2.45 (t, J=7.2 Hz, 2H), 3.01-3.18 (m, 2H), 5.18 (s, 2H), 6.87 (d, J=8.4 Hz, 1H), 7.27 (dd, J=8.4 and 2.1 Hz, 1H), 736 (d, J=2.4 Hz, 1H).

(b) Preparation of BHALys[Lys]$_{32}$[α-Glu-SB]$_{32}$[ε-PEG$_{5700}$]$_{32}$

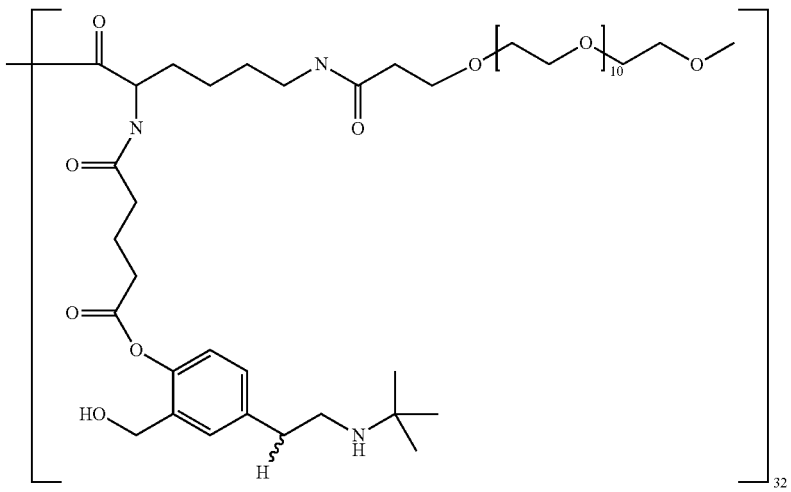

conjugate: 42.5 kDa. $^1$H NMR indicates 32 testosterone/dendrimer. Actual molecular weight is approximately 42.5 kDa (21% testosterone by weight).

Example 24

Preparation of BHALys[Lys]$_{32}$[α-Glu-SB]$_{32}$[ε-PEG$_{1100}$]$_{32}$ SB=Salbutamol
(a) Preparation of Glu-SB

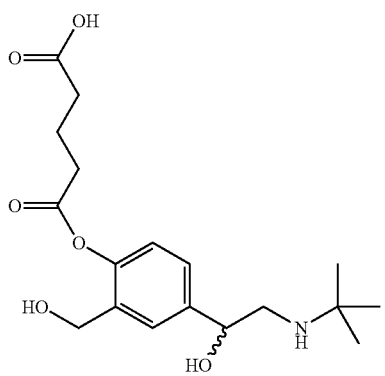 [SMILES: CC(C)(C)NCC(O)c1ccc(OC(=O)CCCC(=O)O)c(CO)c1]

Prepared using Procedure B above, using SB (100 mg, 0.42 mmol) and glutaric anhydride (62 mg, 0.54 mmol) as the linker. Preparative HPLC (BEH 300 Waters XBridge C18, 5 μM, 30×150 mm, gradient: 5% ACN/H$_2$O (1-5 min), 5-60% ACN (5-40 min), 60% ACN (40-45 min), 60-5%

Prepared using Procedure C above, using BHA[Lys]$_{32}$[α-NH$_2$.TFA]$_{32}$[ε-PEG$_{570}$]$_{32}$ (26 mg, 0.86 μmol) and Glu-SB (17 mg, 48.2 μmol). Purification by SEC (sephadex, LH20, MeOH) provided 25 mg (76%) of desired material as a white solid. HPLC (C8, gradient: 40-80% ACN/H$_2$O (1-7 min), 80% ACN (7-9 min), 80-40% ACN (9-11 min), 40% ACN (11-15 min), 10 mM ammonium formate) Rt (min)=5.81. $^1$H NMR (300 MHz, CD$_3$OD) δ (ppm): 1.03-2.02 (m, 738H), 2.25-2.58 (m, 180H), 2.97-3.29 (m, 167H), 3.40-3.94 (m, 1469H), 4.12-4.50 (m, 74H), 5.04 (s, 55H), 6.90 (d, J=8.1 Hz, 27H), 7.28 (d, J=8.1 Hz, 27H), 7.36 (m, 27H). Theoretical molecular weight of conjugate: 37.8 kDa. $^1$H NMR indicates 27 salbutamol/dendrimer. Actual molecular weight is approximately 36.1 kDa (18% salbutamol by weight).

Targeted Constructs

Example 25

Preparation of 4-azidobenzamide-PEG$_{12}$-NEOEOEN [SuN(PN)$_2$][Lys]$_{16}$ [Lys(α-PSSP-DTX)(ε-PEG$_{1100}$)]$_{32}$
(a) Preparation of 4-azidobenzamide-PEG$_{12}$-NEOEOEN [SuN(PN)$_2$][Lys]$_{16}$[Lys(α-NHBOC)(ε-PEG$_{1100}$)]$_{32}$ To a magnetically stirred solution of L-lysine-(α-NH-BOC)(ε-PEG$_{1100}$) (614 mg, 456 μmol) in anhydrous DMF (2.5 mL) was added PyBOP (246 mg, 473 μmol) followed by a solution of 4-azidobenzamide-PEG$_{12}$-NEOEOEN[SuN (PN)$_2$][Lys]$_{16}$[NH$_2$.TFA]$_{32}$ (91 mg, 10.6 μmol) and DIPEA (235 μL, 1.35 mmol) in anhydrous DMF (2.5 mL). After 16 hours at room temperature the reaction was concentrated in vacuo and the residue purified by ultrafiltration (PALL Minimate Cartridge 10 kDa membrane) to provide the target compound as an off-white sticky solid, 433 mg (86%). LCMS (C8 Waters X-Bridge, gradient: 40-90% ACN/H$_2$O (1-7 min), 90% ACN (7-9 min), 90-40% ACN (9-11 min), 40% ACN (11-15 min), 0.1% Formic Acid) Rt (min)=5.17.

(b) Preparation of 4-azidobenzamide-PEG$_{12}$-NEOEOEN [SuN(PN)$_2$][Lys]$_{16}$[Lys(α-NH$_2$.TFA)(ε-PEG$_{1100}$)]$_{32}$ A solution of 4-azidobenzamide-PEG$_{12}$-NEOEOEN[SuN(PN)$_2$][Lys]$_{16}$[Lys(α-NHBOC)(ε-PEG$_{1100}$)]$_{32}$ (431 mg, 9.10 µmol) in TFA/DCM (5 mL/7 mL) was left stirring for 4 h. After this time the reaction mixture concentrated and the resulting residue azeotroped with water (2×10 mL) to provide the target compound as a pale yellow oil, 435 mg (100%). LCMS (C18 Waters X-Bridge, gradient: 5-60% ACN/H$_2$O (1-10 min), 60% ACN/H$_2$O (10-14 min), 60-5% ACN/H$_2$O (14-16 min), 0.1% TFA) Rt=10.65. $^1$H NMR (300 MHz, D$_2$O) δ (ppm): 1.21-2.04 (m, 376H), 2.51-2.56 (m, 71H), 3.12-3.30 (m, 115H), 3.40 (s, 96H), 3.45-3.90 (m, 3077H), 3.91-4.42 (m, 62H), 7.25 (d, J 8.7 Hz, 2H), 7.88 (d, J 8.7 Hz, 2H).

(c) Preparation of 4-azidobenzamide-PEG$_{12}$-NEOEOEN [SuN(PN)$_2$][Lys]$_{16}$[Lys(α-PSSP-DTX)(ε-PEG$_{1100}$)]$_{32}$ The construct was prepared using Procedure C above, using 4-azidobenzamide-PEG$_2$-NEOEOEN[SuN(PN)$_2$][Lys]$_{16}$[Lys(α-NH$_2$.TFA)(δ-PEG$_{1100}$)]$_{32}$ (104 mg, 2.18 µmol) and DTX-PSSP (94 mg, 94.0 µmol). Purification by SEC provided 133 mg (97%) of the desired material as a pale yellow, viscous oil. LCMS (C18 Waters X-Bridge, gradient: 5-60% ACN/H$_2$O (1-10 min), 60% ACN/H$_2$O (10-11 min), 60-5% ACN/H$_2$O (11-13 min), 0.1% Formic acid) Rt (min)=7.59. $^1$H NMR (300 MHz, CD$_3$OD) δ (ppm): 0.88-2.05 (m, 1080H), 2.16-2.56 (m, 212H), 2.60-3.26 (m, 363H), 3.35-3.41 (m, 129H), 3.50-3.94 (m, 3110H), 4.00-4.60 (134H), 4.93-5.10 (m, 28H), 5.20-5.46 (m, 73H), 5.54-5.80 (m, 24H), 5.95-6.30 (m, 23H), 7.14-7.91 (m, 268H). Theoretical molecular weight of conjugate: 75.7 kDa. $^1$H NMR indicates 26 DTX/dendrimer, therefore actual molecular weight is approximately 69.8 kDa (37% DTX by weight).

Example 26

Preparation of biotin-triazolobenzamide-PEG$_{12}$-NEOEOEN[SuN(PN)$_2$][Lys]$_{16}$[Lys(α-PSSP-DTX)(ε-PEG$_{1100}$)]$_{32}$ The construct was prepared using Procedure D above, using 4-azidobenzamide-PEG$_{12}$-NEOEOEN[SuN(PN)$_2$][Lys]$_{16}$[Lys(α-PSSP-DTX)(ε-PEG$_{1100}$)]$_{32}$ (42.5 mg, 674 nmol) and biotin-alkyne (0.4 mg, 1.35 µmol). Purification by SEC provided the target compound as an off-white solid, 39 mg (91%). LCMS (C18 Waters X-Bridge, gradient: 5-60% ACN/H$_2$O (1-10 min), 60'/e ACN/H$_2$O (10-11 min), 60-5% ACN/H$_2$O (11-13 min), 0.1% Formic acid) Rt (min)=7.04. $^1$H NMR (300 MHz, CD$_3$OD) δ (ppm): 0.92-2.02 (m, 982H), 2.10-3.25 (m, 1027H), 3.35-3.42 (m, 128H), 3.49-3.98 (m, 3180H), 4.07-4.69 (m, 131H), 4.96-5.11 (m, 27H), 5.15-5.50 (m, 72H), 5.55-5.80 (m, 24H), 5.98-6.23 (m, 23H), 7.14-8.25 (m, 277H), 8.54-8.56 (m, 1H).

Example 27

Preparation of LyP-1-triazolobenzamide-PEG$_{12}$-NEOEOEN[SuN(PN)$_2$][Lys]$_{16}$[Lys(α-PSSP-DTX)(ε-PEG$_{1100}$)]$_{32}$ LyP-1 (Supplied by AusPep Pty Ltd).

The construct was prepared using Procedure D above, using 4-azidobenzamide-PEO$_{12}$-NEOEOEN[SuN(PN)$_2$][Lys]$_{16}$[Lys(α-PSSP-DTX)(ε-PEG$_{1100}$)]$_{32}$ (44.2 mg, 701 nmol) LyP-alkyne (185 µL of a 10 mg/mL solution in H$_2$O, 1.05 µmol). Purification by SEC provided a bright pink, sticky solid, 46 mg (102%), as a ca. mixture of 60:40 LyP-triazolobenzamide-PEG$_{12}$-NEOEOEN[SuN(PN)$_2$][Lys]$_{16}$[Lys(α-PSSP-DTX)(ε-PEG$_{1100}$)]$_{32}$/4-azidobenzamide-PEG$_{12}$-NEOEOEN[SuN(PN)$_2$][Lys]N$_{16}$[Lys(α-PSSP-DTX)(ε-PEG$_{1100}$)]$_{32}$. LCMS (C8 Waters X-Bridge, gradient: 40-90% ACN/H$_2$O (1-7 min), 90% ACN (7-9 min), 90-40% ACN (9-11 min), 40% ACN (11-15 min), 0.1% Formic Acid) Rt (min)=6.07 (LyP-Dendrimer conjugate); 7.10 (Azido-Dendrimer starting material).

Example 28

Preparation of deslorelin-triazolobenzamide-PEG$_{12}$NEOEOEN[SuN(PN)$_2$][Lys]$_{16}$[Lys(α-PSSP-DTX)(ε-PEG$_{1100}$)]$_{32}$ The construct was prepared using Procedure D above, using 4-azidobenzamide-PEG$_{12}$-NEOEOEN[SuN(PN)$_2$][Lys]$_{16}$[Lys(α-PSSP-DTX)(ε-PEG$_{1100}$)]$_{32}$ (41.7 mg, 662 nmol) and deslorelin-alkyne (130 µL of a 10 mg/mL solution in H$_2$O, 993 nmol). Purification by SEC provided a pale yellow, sticky solid, 43 mg (100%), as a ca. mixture of 70:30 deslorelin-triazolobenzamide-PEG$_{12}$-NEOEOEN[SuN(PN)$_2$][Lys]$_{16}$[Lys(α-PSSP-DTX)(ε-PEG$_{1100}$)]$_{32}$/4-azidobenzamide-PEO$_2$-NEOEOEN[SuN(PN)$_2$][Lys]$_{16}$[Lys(α-PSSP-DTX) (ε-PEG$_{1100}$)]$_{32}$. LCMS (C8 Waters X-Bridge, gradient: 40-90% ACN/H$_2$O (1-7 min), 90% ACN (7-9 min), 90-40% ACN (9-11 min), 40% ACN (11-15 min), 0.1% Formic Acid) Rt (min)=6.42 (Deslorelin-Dendrimer conjugate); 7.11 (Azido-Dendrimer starting material).

Example 29

Preparation Antibody-Dendrimer Conjugation Using Streptavidin as a Joining Unit

To a solution of Alexa Fluor® 750 Streptavidin (Av) (0.1 µg/mL) in phosphate-buffered saline (PBS, 2 mL) was added Abcam #ab24293 Anti-EGFR antibody biotin (Ab) (30 µL of 10 µg/mL stock solution). To this reaction solution was added a solution of biotin-triazolobenzamide-PEG$_{12}$-NEOEOEN[SuN(PN)$_2$][Lys]$_{16}$[Lys(α-PSSP-DTX)(ε-PEG$_{1100}$)]$_{32}$ (DTX-D) in PBS (5 µL of 1.0 µg/mL stock solution). The mixture was left stirring for 10 s and the above procedure of adding Ab and DTX-D to the Av solution was repeated in total of 8 times. Finally the reaction was quenched using 50 µg/mL of Biotin, (Sigma Aldrich, #B4501-1G), and after incubating for 5 min, 1 mL of the sample was precipitated with 50 µL of Protein G agarose. Confirmation of successful conjugation was demonstrated using SDS-PAGE with a new band assigned to the conjugate appearing at 260 kDa and HPLC (column: X Bridge C8, 3.5 µm 3.0×100 mm, detection wavelength=243 nm, 10 µL injections and run gradient: 5-80% ACN/H$_2$O, 0.1% TFA for 15 min Rt (min)=1.40 biotin, 5.83 (Target Ab-DTX-D conjugate); 7.24 (unreacted Ab), 9.84 (unreacted DTX-D).

Example 30

Preparation of an Antibody Activated with an Azide Joining Unit

A solution of coupling buffer (0.1 M sodium acetate+0.15 M NaCl, pH 5.5) was prepared and used to make up stock solutions for the following reaction. Solid sodium metaperiodate (2.1 mg) was dissolved in coupling buffer (0.5 mL) and then was added to a solution of Her2 mAb* (25 µg) also diluted in coupling buffer (0.5 mL). The reaction mixture was incubated at room temperature (RT) in the dark for 45 min. Unreacted material was removed by centrifugal filter units (MW cut off 50 kDa). To a portion of the oxidised mAb solution (0.3 mL) was added a stock solution of a azide containing joining unit (JU) ($NH_2$—O—$C_4H_8$—NH-(PEG)$_{12}$-$N_3$¥, 0.2 mL; 1 mg/mL in PBS), followed by aniline (5 µL). The reaction was mixed and left for 24 h at RT. After this time the mAb-JU conjugate was separated from unreacted material by centrifugal filter units.

¥In a similar manner other joining units could also be installed onto the antibody, e.g. $NH_2$—O—$C_4H_8$—NH-(PEG)$_{12}$-benzylazide, $NH_2$—O—$C_4H_8$—NH-(PEG)$_{12}$-DBCO and $NH_2$—O—$C_4H_8$—NH-(PEG)$_{12}$-maleimide.

*In this example Her2 mAb is utilised however, in a similar fashion other antibodies could also be utilised. In addition to utilising other activating chemistry's e.g. partial reduction of dithiane groups within the antibody followed by capture with maleimide containing joining units Example 31

Conjugation of the Activated Antibody with a Drug Loaded Dendrimer

To a solution of the azide activated mAb-JU from Example 30 above could be added a solution of a drug loaded dendrimer suitably functionalised with a reactive alkyne, such as DBCO. The reaction could be monitored for completion using HPLC and the desired product could be isolated by either SEC chromatography or prep HPLC using standard protocols.

¥In a similar manner other dendrimer activating units could also be installed onto the unique point of attachment in the dendrimer, e.g. azide and maleimide.

Example 32

Water Solubility Study on Drug Loaded Dendrimers:
Protocol:

To 30 mg of dendrimer (freeze-dried from water) was added 100 µL of deionised water. After mixing for 10 minutes, additional aliquots of water (10-30 µL per addition) were added with vortexing and incubation for 10 mins until full dissolution was obtained. This amount is represented in Table 1 as the water solubility of the dendrimer. The equivalent drug solubility is determined by multiplying the % drug loading/100 and is represented in Table 1 (column 3) as Equivalent drug solubility on dendrimer. Finally, the fold increase is obtained by dividing the Equivalent drug solubility on dendrimer by the solubility of the drug and is represented in Table 1 (column 4).

TABLE 1

| 1 Example | 2 Water solubility of dendrimer (mg/mL) | 3 Equivalent drug solubility on dendrimer (mg/mL) | 4 Fold increase in drug solubility |
|---|---|---|---|
| 1 (b)* | 186 | 24 | 4800 |
| 2 (b)* | 57 | 14 | 2800 |
| 3 (b)* | 89 | 23 | 5600 |
| 4 (c)* | 109 | 22 | 4400 |
| 5 (b)* | 214 | 75 | 4000 |
| 6 (b)* | 100 | 32 | 6400 |
| 7 (b)* | 91 | 25 | 5000 |
| 8 (c)* | 131 | 41 | 8200 |
| 9 (b)* | 63 | 20 | 4000 |

TABLE 1-continued

| 1 Example | 2 Water solubility of dendrimer (mg/mL) | 3 Equivalent drug solubility on dendrimer (mg/mL) | 4 Fold increase in drug solubility |
|---|---|---|---|
| 10 (b)* | 138 | 43 | 8600 |
| 12 (b)* | 15 | 3 | 10000 |
| 14 (c)* | 183 | 57 | 11400 |
| 15 (c)* | 180 | 45 | 9000 |
| 16* | 205 | 59 | 11800 |
| 17* | 373 | 67 | 13400 |
| 19* | 477 | 109 | 21900 |
| 20 (b)¥ | >75 | 11.5 | 482 |
| 21¥ | >81 | 14.8 | 618 |
| 22 (b)¥ | >89 | 14.7 | 610 |
| 23¥ | >125 | 26.6 | 1109 |

*drug = docetaxel. The solubility of docetaxel and in water is 5 µg/mL
¥drug = testosterone: The solubility of testosterone in water is 24 µg/mL.

Example 33

Plasma Stability Study on Dendrimers:
Protocol:

To 0.5 mL of mouse plasma was added 0.1 mL of dendrimer solution (2 mg/mL, drug equivalent in saline). The mixtures were vortexed (30 s) then incubated at 37° C. At various timepoints (0.5, 2.5, 4.5, 22 hours) 0.1 mL aliquots were removed and added to 0.2 mL ACN. The resulting mixtures were vortexed (30 s), centrifuged (10 min, 4° C.) filtered and analysed by HPLC (C8, 3.9×150 mm, 5 µm, wavelength=243 nm, 10 µL injections, gradient: 40-80% ACN/$H_2O$ (1-7 min), 80% ACN (7-9 min), 80-40% ACN (9-11 min), 40% ACN (11-15 min), 10 mM ammonium formate, pH 7.40) which when compared against a standard (2 mg//mL) provided the concentration of free docetaxel in the sample.

TABLE 2

Docetaxel release in plasma. Results are shown as a percentage of total docetaxel.

| Example Compound | Time | | | |
|---|---|---|---|---|
| | 0.5 | 2.5 | 4.5 | 22 |
| Exp 3(b) | 8.5 | 32.5 | 52.5 | 73 |
| Exp 10(b) | 10 | 21 | 28.5 | 75 |
| Exp 7(b) | 20.5 | 32 | 32.5 | 71.5 |
| Exp 14(c) | 4 | 9 | 16 | 70 |
| Exp 8(c) | 4.5 | 13.5 | 17.5 | 43 |
| Exp 6(b) | 7.5 | 9 | 13 | 23.5 |
| Exp 4(c) | 1.5 | 10 | 18.5 | 17.5 |
| Exp 2(b) | 5 | 8 | 11.5 | 15.5 |
| Exp 1(b) | 0 | 3 | 7.5 | 14.5 |
| Exp 15(c) | 0 | 5 | 8 | 45 |
| Exp 5(b) | 0 | 0 | 0 | 4 |
| Exp 9(b) | 0.5 | 1.5 | 1 | 1 |
| Exp 16 | 0 | 0 | 0 | 0 |
| Exp 17 | 0 | 0 | 0 | 1 |

Example 34

Cell Growth Inhibition Studies SRB Assay

Cell growth inhibition was determined using the Sulforhodamine B (SRB) assay [Voigt W. "Sulforhodamine B assay and chemosensitivity" *Methods Mol. Med.* 2005, 110, 39-48.] against various cancer cell lines after 72 hours with each experiment run in duplicate. $GI_{50}$ is the concentration required to inhibit total cell growth by 50%, as per NCI standard protocols.

All solutions were prepared in saline (except docetaxel which was made in ethanol). All solutions were stored at −20° C. All values were based on the equivalent drug loading. The results shown in Table 3 are the average of experiments run in duplicate in nanomolar range.

TABLE 3

Growth Inhibition Studies.

$GI_{50}$ Values (nM)

| Cell line | Docetaxel | Exp 1 (b) | Exp 3 (b) | Exp 4 (c) | Exp 5 (b) | Exp 13 (b) | Exp 2 (b) | Exp 6 (b) | Exp 7 (b) | Exp 8 (c) | Exp 9 (b) | Exp 10 (b) |
|---|---|---|---|---|---|---|---|---|---|---|---|---|
| PC-3 (Prostate) | 2.5 | 17 | 4.5 | 21.5 | 160 | 288 | 109.5 | 10.5 | 6.5 | 9.5 | 617.5 | 9.5 |
| DU145 (Prostate) | 2.5 | 11.5 | 4 | 12 | 148 | 99 | | | | | | |
| HCT116 (Colon) | 0.7 | 8.5 | 1 | 9 | 85.5 | 30.5 | | | | | | |
| ES2 (Ovarian) | 5 | 16.5 | 4 | 8.6 | 115.5 | 48 | 115.5 | 12.5 | 8 | 12 | 888 | 10.5 |
| HT29 (Colon) | 1.5 | 12.5 | 2 | 9.5 | 97.5 | 117 | | | | | | |
| H460 (Lung) | 1.5 | 13 | 8 | 11 | 106 | 127 | 73 | 11 | 4.5 | 7 | 365 | 6.5 |
| A549 (Lung) | 3.5 | 13 | 3.5 | 8.5 | 56.5 | 73 | | | | | | |
| MDA-MB-231 (Breast) | 3.5 | 11.5 | 0.5 | 6.5 | 50.5 | 50.5 | | | | | | |
| A2058 (Melanoma) | 2 | 9.5 | 2 | 8 | 71.5 | 100.5 | | | | | | |
| MCAS (Ovarian) | 7 | 29 | 7 | 20 | 252.5 | 117 | | | | | | |

Example 35

Half Maximal Inhibitory Concentration ($IC_{50}$) Using the MTT Assay

The $IC_{50}$ using the MTT assay [Wilson, Anne P. (2000). "Chapter 7: Cytotoxicity and viability". In Masters, John R. W. *Animal Cell Culture: A Practical Approach*. Vol. 1 (3rd ed.). Oxford: Oxford University Press] was determined against various cancer cell lines after 72 hours. The results are shown in Table 4.

TABLE 4

Half Maximal Inhibitory Concentration Studies ($IC_{50}$).

$IC_{50}$ Values (nM)

| Cell line | Exp 14 (c) | Exp 15 (c) | Exp 17 | Exp 18 | Exp 19 |
|---|---|---|---|---|---|
| A549 | 1.5 | 8.1 | 159.7 | 20.3 | 7.7 |
| H460 | 4.3 | 31.8 | 603.3 | 7.5 | 23.7 |
| HCT-116 | 2.6 | 7.2 | 215.7 | 2.9 | 6.5 |
| HT-29 | 0.5 | 5.7 | 85 | 1.8 | 5.9 |
| A2780 | 4.6 | 13.6 | 291 | 5.7 | 6.3 |
| MCF-7 | 0.5 | 8.3 | 93.7 | 3.3 | 6.3 |
| DU-145 | 7.3 | 29.5 | 290 | 11.6 | 15.5 |
| PC-3 | 3.8 | 11.8 | 358.7 | 5.9 | 7.4 |

Example 36

Maximum Tolerated Dose (MTD) Study

Groups of female Balb/c mice were administered an intravenous injection of dendrimer (0.1 ml/10 g body weight) or docetaxel (0.05 ml/10 g body weight) once weekly for 3 weeks (day 1, 8 and 15). Mice were weighed daily and watched for signs of toxicity. Animals were monitored for up to 10 days following the final drug dose. Any mice exceeding ethical endpoints (≥20% body weight loss, poor general health) were immediately sacrificed and observations were noted. The results shown in Table 5 demonstrate that drug conjugated to the dendrimer increases the tolerated dose. More than twice the dose of docetaxel could be safely administered using drug dendrimer construct compared to docetaxel alone.

TABLE 5

Drug doses tested and maximum tolerated dose identified

| Drug | Doses tested (mg/kg docetaxel equivalents) | Tolerated dose (mg/kg docetaxel equivalents) |
|---|---|---|
| Docetaxel | 15, 20, 25, 30 | 15 |
| Example 3 (b) | 15, 20, 23, 25, 30 | 20 |
| Example 8 (c) | 15, 20, 25, 30, 32, 35 | 32 |
| Example 4 (c) | 20, 25, 30 | 20 |

Example 37

Xenograft MDA-MB-231 Efficacy Study

Female Balb/c nude mice (Age 7 weeks) were inoculated subcutaneously on the flank with 3.5×106 MDA-MB-231 cells in PBS:Matrigel (1:1). Thirteen days later 50 mice with similar sized tumours (~110 mm$^3$) were randomised into 5 groups. Each treatment group was administered one of the following doses: saline; docetaxel (15 mg/kg); Exp. 3 (b) (20 mg/kg); Exp. 8 (c) (32 mg/kg). All treatments were administered intravenously once weekly for three weeks (day 1, 8 and 15) at 0.1 mL/10 g body weight except docetaxel which was given at 0.05 mL/10 g body weight. The experiment was ended on day 120 or earlier if an ethical endpoint was met. Results shown in Table 6 show that the dendrimer constructs were more effective in suppressing tumour growth for longer.

TABLE 6

Xenograft efficacy study showing mean tumour volume mm³ over time

| Day | Mean tumour Volumne mm³ (sd) | | | |
|---|---|---|---|---|
| | Vehicle | Docetaxel | Exp 3 (b) | Exp 8 (c) |
| 1 | 112.35 (6.31), n = 10 | 111.94 (6.41), n = 10 | 111.74 (6.65), n = 10 | 111.73 (6.41), n = 10 |
| 9 | 426.55 (24.11), n = 10 | 135.57 (18.85), n = 10 | 84.02 (6.33), n = 10 | 108.86 (9.31), n = 10 |
| 19 | 1337.61 (18.4), n = 4 | 49.92 (11.61), n = 10 | 28.26 (1.91), n = 10 | 30.59 (1.64), n = 10 |
| 29 | ** | 18.81 (2.09), n = 10 | 10.46 (0.5), n = 8 | 11.58 (1.2), n = 9 |
| 40 | | 10.75 (1.95), n = 10 | 5.92 (1.31), n = 5 | 5.75 (0.92), n = 8 |
| 61 | | 95.94 (33.08), n = 10 | 4 (0), n = 4 | 4 (0), n = 8 |
| 81 | | 478.67 (169.27), n = 7 | 0.5 (0), n = 4 | 0.5 (0), n = 8 |
| 100 | | 974.83 (302.59), n = 3 | 0.5 (0), n = 4 | 1.67 (0.74), n = 6 |
| 120 | | ** | 0.37 (0.12), n = 4 | 16.2 (10.24), n = 6 |

** No data due to ethical endpoint reached.
n = number of animals per dosing group

Example 38

Xenograft MDA-MB-231 Toxicity Study

A total of twenty Female Balb/c nude mice (Age 7 weeks) were prepared with subcutaneous tumours as outlined above. The 20 mice were randomised into 5 groups of four mice (mean tumour volume ~90 mm³). Animals were eye bled in the morning for baseline blood cell counts and then drug dosing commenced later that day (day 1). Drug dosing was performed on days 1, 8 and 15 at the previously determined MTD doses: docetaxel (15 mg/kg); Exp. 3 (b)(20 mg/kg); Exp. 8 (c) (32 mg/kg); Exp. 4 (b) (20 mg/kg). A second eye bleed was performed on day 11 (Table 7 A-C). Mice were killed one day following the final drug dose (day 16). Histology weights of tissues at day 16 are shown in Table 8.

TABLE 7 A

White Blood Cell analysis at days 1 and 11.
Mean WBC (sd) × 10⁹ cells/L

| | PBS | docetaxel | Exp. 3 (b) | Exp. 8 (c) | Exp.4 (b) |
|---|---|---|---|---|---|
| Day 1 | 5.76 (0.31) | 5.79 (1.01) | 5.79 (1.53) | 6.59 (0.62) | 4.95 (2.25) |
| Day 11 | 8.57 (1.94) | 3.99 (0.93) | 3.99 (0.29) | 4.27 (0.35) | 5.37 (1.72) |

TABLE 7 B

Results of Neutrophil Analysis at days 1 and 11.
Mean Neutrophils (sd) × 10⁹ cells/L

| | PBS | docetaxel | Exp. 3 (b) | Exp. 8 (c)) | Exp.4 (b) |
|---|---|---|---|---|---|
| Day 1 | 1.53 (1.12) | 0.86 (0.26) | 1.01 (0.53) | 0.93 (0.51) | 1.07 (0.57) |
| Day 11 | 2.84 (0.62) | 0.85 (0.12) | 1.84 (0.18) | 1.76 (0.15) | 1.27 (0.64) |

TABLE 7 C

Results of Lymphocyte analysis at days 1 and 11.
Mean Lymphocytes (sd) × 10⁹ cells/L

| | PBS | docetaxel | Exp. 3 (b) | Exp. 8 (c) | Exp.4 (b) |
|---|---|---|---|---|---|
| Day 1 | 5.76 (0.31) | 5.79 (1.01) | 5.79 (1.53) | 6.59 (0.62) | 4.95 (2.25) |
| Day 11 | 8.57 (1.94) | 3.99 (0.93) | 3.99 (0.29) | 4.27 (0.35) | 5.37 (1.72) |

TABLE 8

Organ Weights at Completion of Toxicity Experiment.

| | PBS | Docetaxel | Exp. 3 (b) | Exp. 8 (c) | Exp. 4 (b) |
|---|---|---|---|---|---|
| Mean Tumour Weights (g) (sd) | 0.832 (0.277) | 0.048 (0.010) | 0.020 (0.008) | 0.033 (0.011) | 0.079 (0.048) |
| Mean Spleen Weights (g) (sd) | 0.149 (0.022) | 0.068 (0.003) | 0.077 (0.011) | 0.092 (0.019) | 0.087 (0.027) |
| Mean Liver Weights (g) (sd) | 0.838 (0.058) | 0.793 (0.087) | 0.763 (0.090) | 0.780 (0.103) | 0.762 (0.096) |

Example 39

Pharmacokinetic Analysis

The plasma half-lives of tritium labelled docetaxel and the construct from Experiment 8 (c) (prepared using tritium labelled docetaxel) after IV administration into rats were determined (Kaminskas, L. M., Boyd, B. J., Karellas, P., Krippner, G. Y., Lessene, R., Kelly, B and Porter, C. J. H. "The Impact of Molecular Weight and PEG Chain Length on the Systemic Pharmacokinetics of PEGylated Poly-L-Lysine Dendrimers" Molecular Pharm. 2008, 5, 449-463). Results showed docetaxel was cleared from plasma with a half-life of <1 hour as expected whilst Exp 8 (c) construct displayed reduced plasma clearance with a half-life of approximately 30 hour.

What is claimed is:

1. A macromolecule comprising:
   i) a dendrimer comprising a core and at least one generation of lysine residue building units, the outermost generation of building units having surface amino groups;
   ii) a first terminal group covalently attached to a first surface amino group of a building unit, comprising a residue of docetaxel (DTX);
   iii) a second terminal group covalently attached to a second surface amino group of a building unit, comprising a pharmacokinetic modifying agent, wherein the pharmacokinetic modifying agent is a polyethylene glycol (PEG);
   wherein the first terminal group is covalently attached to the surface amino group of the dendrimer through a diacid linker, the diacid linker comprising a 2,2'-thiodiacetic acid residue; wherein the diacid linker forms an ester bond with a hydroxyl group of the DTX and an amide bond with the surface amino group; or a pharmaceutically acceptable salt thereof.

2. The macromolecule of claim 1, wherein the polyethylene glycol has a molecular weight in the range of 1000 to 2500 Da.

3. The macromolecule of claim 1, wherein the polyethylene glycol has an average molecular weight of 2200 Da.

4. The macromolecule of claim 1, wherein the first terminal group is covalently attached to an α-amino surface group of a lysine residue building unit, and the second terminal group is covalently attached to an ε-amino surface group of a lysine residue building unit.

5. The macromolecule of claim 1, wherein the first terminal group is covalently attached to an ε-amino surface group of a lysine residue building unit, and the second terminal group is covalently attached to an α-amino surface group of a lysine residue building unit.

6. The macromolecule of claim 1, wherein the dendrimer has 3 to 6 generations of building units.

7. The macromolecule of claim 1, wherein the dendrimer has 5 generations of building units.

8. The macromolecule of claim 1, wherein the first terminal group and the second terminal group are present in about a 1:1 ratio.

9. The macromolecule of claim 1, wherein the first terminal group is attached to greater than 44% of the surface amino groups.

10. The macromolecule of claim 1, wherein the second terminal group is attached to greater than 44% of the surface amino groups.

11. The macromolecule of claim 1, wherein the macromolecule comprises a third terminal group which is a blocking group, or a targeting group.

12. The macromolecule of claim 1, wherein the macromolecule has a particulate size of less than 1000 nm and/or has a molecular weight of at least 30 kDa.

13. The macromolecule of claim 1, wherein the macromolecule releases greater than 50% of the DTX in between 2 hours and 48 hours, as measured in vitro in plasma at 37° C.

14. A pharmaceutical composition comprising the macromolecule of claim 1 and a pharmaceutically acceptable carrier.

15. The pharmaceutical composition of claim 14, wherein one or more of the following apply:
   (a) the composition is free of polyethoxylated castor oil and polysorbate 80;
   (b) the plasma half-life of released DTX is at least two times the half-life of native DTX (taxotere).

16. A method of treating or suppressing the growth of a cancer in a subject comprising administering an effective amount of a macromolecule according to claim 1, wherein the dose is equivalent to 1 mg to 100 mg per kg of DTX.

17. A method of reducing the toxicity of, or reducing side effects associated with, docetaxel (DTX), or formulation of DTX, or of reducing hypersensitivity in a subject upon treatment with DTX or a formulation of DTX, comprising administering a macromolecule according to claim 1.

18. The method of claim 17, wherein:
   (a) the toxicity that is reduced is selected from the group consisting of hematologic toxicity, neurological toxicity, gastrointestinal toxicity, cardiotoxicity, hepatotoxicity, nephrotoxicity, and encephalotoxicity, or
   (b) the side effects which are reduced are selected from the group consisting of neutropenia, leukopenia, thrombocytopenia, myelotoxicity, myelosuppression, neuropathy, fatigue, vertigo, encephalopathy, anemia, dysgeusia, dyspnea, constipation, anorexia, nail disorders, fluid retention, asthenia, pain, nausea, vomiting mucositis, alopecia, skin reactions, myalgia, hypersensitivity and anaphylaxis.

19. A compound, or a salt thereof, comprising a 2,2'-thiodiacetic acid linker covalently attached to the hydroxy group of the propanoyl side chain of DTX.

20. The compound of claim 19, or a salt thereof, having the structure:

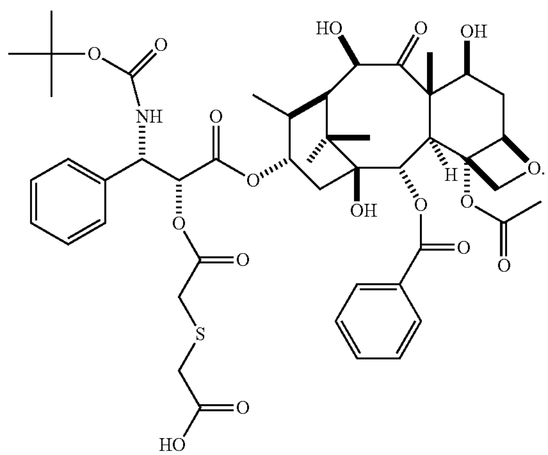

21. The compound of claim 19, further comprising a lysine residue covalently attached by its first amine to the distal carboxy group of the 2,2'-thiodiacetic acid linker; and by its second amine to a PEG.

* * * * *